United States Patent
Itoh et al.

(10) Patent No.: US 10,494,330 B2
(45) Date of Patent: Dec. 3, 2019

(54) METHYL MENTHOL DERIVATIVE AND COOLING AGENT COMPOSITION CONTAINING SAME

(71) Applicant: TAKASAGO INTERNATIONAL CORPORATION, Tokyo (JP)

(72) Inventors: Hisanori Itoh, Kanagawa (JP); Yoji Hori, Kanagawa (JP); Masashi Otsuka, Kanagawa (JP); Takaji Matsumoto, Kanagawa (JP); Tomoharu Sato, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 15/559,762

(22) PCT Filed: Mar. 24, 2016

(86) PCT No.: PCT/JP2016/059500
§ 371 (c)(1),
(2) Date: Sep. 19, 2017

(87) PCT Pub. No.: WO2016/153011
PCT Pub. Date: Sep. 29, 2016

(65) Prior Publication Data
US 2018/0057447 A1    Mar. 1, 2018

(30) Foreign Application Priority Data

Mar. 25, 2015 (JP) ................................. 2015-062301

(51) Int. Cl.
| | | |
|---|---|---|
| *C07C 233/58* | (2006.01) | |
| *C07C 69/75* | (2006.01) | |
| *C07C 255/44* | (2006.01) | |
| *C07C 233/63* | (2006.01) | |
| *C07C 233/60* | (2006.01) | |
| *C07C 69/68* | (2006.01) | |
| *A23L 2/52* | (2006.01) | |
| *A23L 27/00* | (2016.01) | |

(Continued)

(52) U.S. Cl.
CPC .............. *C07C 233/58* (2013.01); *A23L 2/52* (2013.01); *A23L 27/00* (2016.08); *A61K 8/37* (2013.01); *A61K 8/42* (2013.01); *A61K 8/4926* (2013.01); *A61K 8/4973* (2013.01); *A61Q 11/00* (2013.01); *A61Q 19/10* (2013.01); *C07C 69/68* (2013.01); *C07C 69/75* (2013.01); *C07C 233/60* (2013.01); *C07C 233/63* (2013.01); *C07C 255/44* (2013.01); *C07D 213/40* (2013.01); *C07D 317/72* (2013.01); *A23V 2002/00* (2013.01); *C07C 2601/14* (2017.05)

(58) Field of Classification Search
None
See application file for complete search history.

(56) References Cited

U.S. PATENT DOCUMENTS

| 3,111,127 A | 11/1963 | Jarboe et al. |
|---|---|---|
| 3,988,482 A | 10/1976 | Higashiyama et al. |

(Continued)

FOREIGN PATENT DOCUMENTS

| DE | 102012202885 A1 | 5/2012 |
|---|---|---|
| GB | 1392907 | 5/1975 |

(Continued)

OTHER PUBLICATIONS

Leffingwell and Associates. Menthol—a cool place. downloaded from https://web.archive.org/web/20110716201646/http://www.leffingwell.com/menthol1/menthol1.htm, dated Jul. 16, 2011. (Year: 2011).*

(Continued)

*Primary Examiner* — Michael P Cohen
(74) *Attorney, Agent, or Firm* — Sughrue Mion, PLLC

(57) ABSTRACT

The purpose of the present invention is to provide a cooling agent composition containing a novel methyl menthol derivative having no undesirable feeling of stimulation, malodor, bitterness, or the like, it being possible to use the cooling agent composition as a cooling agent or sensory stimulation agent having exceptional persistence of a sense of coolness and refreshing feeling. The present invention pertains to a cooling agent composition containing a methyl menthol derivative represented by general formula (1A) or general formula (1B).

[Chem. 1]

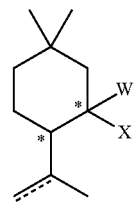

(1A)

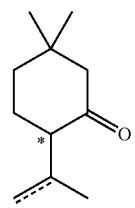

(1B)

14 Claims, No Drawings

(51) Int. Cl.

| | | |
|---|---|---|
| A61K 8/42 | (2006.01) | |
| A61K 8/37 | (2006.01) | |
| A61K 8/49 | (2006.01) | |
| A61Q 11/00 | (2006.01) | |
| A61Q 19/10 | (2006.01) | |
| C07D 213/40 | (2006.01) | |
| C07D 317/72 | (2006.01) | |

(56) References Cited

U.S. PATENT DOCUMENTS

| | | | |
|---|---|---|---|
| 4,038,270 | A | 7/1977 | Higashiyama et al. |
| 4,157,384 | A | 6/1979 | Watson et al. |
| 4,459,425 | A | 7/1984 | Amano et al. |
| 5,266,592 | A | 11/1993 | Grub et al. |
| 5,451,404 | A | 9/1995 | Furman |
| 5,608,119 | A | 3/1997 | Amano et al. |
| 2002/0198412 | A1 | 12/2002 | Green et al. |
| 2003/0215532 | A1 | 11/2003 | Nakatsu et al. |
| 2004/0052735 | A1 | 3/2004 | Nakatsu et al. |
| 2005/0222256 | A1 | 10/2005 | Erman et al. |
| 2006/0276667 | A1* | 12/2006 | Galopin .......... A61K 8/42 558/410 |
| 2007/0225378 | A1 | 9/2007 | Ishida et al. |
| 2008/0300314 | A1 | 12/2008 | Galopin et al. |
| 2009/0054520 | A1 | 2/2009 | Surburg et al. |
| 2010/0076080 | A1 | 3/2010 | Yelm et al. |
| 2011/0015227 | A1* | 1/2011 | Desierto .......... A61K 8/02 514/321 |
| 2013/0216486 | A1 | 8/2013 | Yelm et al. |
| 2014/0161846 | A1* | 6/2014 | Luciow .......... A61K 8/11 424/401 |
| 2014/0186272 | A1 | 7/2014 | Yelm et al. |
| 2015/0030744 | A1 | 1/2015 | Lombardo et al. |

FOREIGN PATENT DOCUMENTS

| | | |
|---|---|---|
| JP | 47-16647 A | 9/1972 |
| JP | 47-16648 A | 9/1972 |
| JP | 47-16649 A | 9/1972 |
| JP | 48-33069 | 5/1973 |
| JP | 52-105223 A | 9/1977 |
| JP | 58-88334 A | 5/1983 |
| JP | 61-194049 A | 8/1986 |
| JP | 2-290827 A | 11/1990 |
| JP | 5-125073 A | 5/1993 |
| JP | 5-255186 A | 10/1993 |
| JP | 5-255217 A | 10/1993 |
| JP | 6-65023 A | 3/1994 |
| JP | 7-82200 A | 3/1995 |
| JP | 7-118119 A | 5/1995 |
| JP | 7-506868 A | 7/1995 |
| JP | 11-158107 A | 6/1999 |
| JP | 2001-294546 A | 10/2001 |
| JP | 2005-343915 A | 12/2005 |
| JP | 2007-511546 A | 5/2007 |
| JP | 2007-530689 A | 11/2007 |
| JP | 2008-115181 A | 5/2008 |
| JP | 2009-173628 A | 8/2009 |
| JP | 2011-530608 A | 12/2011 |
| JP | 2013-189623 A | 9/2013 |
| WO | 2013/033501 A1 | 3/2013 |

OTHER PUBLICATIONS

Elisabetta Brenna,* Claudio Fuganti and Stefano Serra. Enantioselective perception of chiral odorants. Tetrahedron: Asymmetry 14 (2003) 1-42. (Year: 2003).*

Donald C. Wigfield and David J. Phelps. The Factors Influencing Stereochemistry in the Reduction of Conformationally Mobile 2-Alkylcyclohexanones by Sodium Borohydride. Journal of the American Chemical Society 96:2 1974 543-549. (Year: 1974).*

John C. Leffingwell. Cooling Ingredients and Their Mechanism of Action. Handbook of Cosmetic Science and Technology, 3rd ed., Andre O. Barel, Marc Paye, Howard I. Maibach, Eds., Informa Healthcare (Pub.), New York, 2009, pp. 661-675. (Year: 2009).*

Danny Gauvreau and Louis Barriault. Conservation of the Planar Chiral Information in the Tandem Oxy-Cope/Ene Reaction. J. Org. Chem. 2005, 70, 1382-1388. (Year: 2005).*

William G. Dauben, Milton Lorber, and Dwight S. Fullerton. Allylic Oxidation of Olefins with Chromium Trioxide-Pyridine Complex. J. Org. Chem. vol. 34, No. 11, Nov. 1969, pp. 3587-3592. (Year: 1969).*

Published collection of well-known prior arts (Flavor and Fragrance), Part 1, Jan. 29, 1999, Published by Japan Patent Office, 4 Pages total.

Soichi Sakane et al., "Asymmetric Cyclization of Unsaturated Aldehydes Catalyzed by a Chiral Lewis Acid", 1986 Pergamon Press Ltd., Tetrahedron vol. 42, No. 8 pp. 2203 to 2209, 1986.

Christopher Dean et al., "Reactions of Cyclohexane Derivatives in Superacids", J. Chem. Soc. Perkin Trans. 2 1991, pp. 1541-1543.

Ramaswamy Ravichandran et al., "β-Cyclodextrin and its derivatives directed axial attack of hydride ion in the reduction of ( R)-( +)-pulegone and (2S,5R)-( −)-menthone", Journal of Molecular Catalysis A: Chemical 109 (1996), pp. 201-208.

Claude Spino et al., "p-Menthane-3-carboxaldehyde: A Useful Chiral Auxiliary for the Synthesis of Chiral Quaternary Carbons of High Enantiomeric Purity", J. Am. Chem. Soc. 2004, 126, pp. 13312-13319.

Jialie Luo et al., "Cell-based Calcium Assay for Medium to High Throughput Screening of TRP Channel Functions using FlexStation 3", Journal of Visualized Experiments, Aug. 2011, 54, e3149, pp. 1-6, DOI: 10.3791/3149.

International Search Report, issued by International Searching Authority in corresponding International Application No. PCT/JP2016/059500, dated Jun. 28, 2016, (PCT/ISA/210).

Written Opinion, issued by International Searching Authority in corresponding International Application No. PCT/JP2016/059500, dated Jun. 28, 2016, ( PCT/ISA/237).

Takeaki Naito et al., "Photocyclisation of Enamides. Part 29.[1,2] A General Strategy for the Synthesis of Ipecac and Heteroyohimbine Alkaloids", J. Chem. Soc. Perkin Trans. 1 1990, pp. 1271-1280.

Communication dated Oct. 10, 2018, from the European Patent Office in counterpart European Application No. 16768914.0.

Peter Weyerstahl et al. "Von Menthon zu Shyobunon—Änderung des Geruchs mit der Struktur" Institut für Organische Chemie der Technischen Universität Berlin, Jan. 1, 1985, [retrieved from the Internet URL: https://onlinelibrary.wiley.com/doi/pdf/1 0.1 002/jiac. 198719870202 ] XP055511057 (pp. 89-101).

Maurice Chastrette et al. "Structure-Minty Odour Relationships: Suggestion of an Interaction Pattern" Flavour and Fragrance Journal, vol. 13, No. 1, Jan. 1, 1998 (pp. 5-18) XP009064482.

Communication dated May 28, 2019, issued by the Indian Patent Office in counterpart Indian Application No. 201747033143.

* cited by examiner

METHYL MENTHOL DERIVATIVE AND COOLING AGENT COMPOSITION CONTAINING SAME

TECHNICAL FIELD

The present invention relates to a novel methyl menthol derivative and a cooling agent composition containing the methyl menthol derivative. Further, the present invention relates to a sensory stimulant composition containing such a cooling agent composition, and a flavor composition and/or a fragrance composition and products, each containing such a sensory stimulant composition blended therein.

BACKGROUND ART

Conventionally, a cooling agent which gives a refreshing sensation (a refresh feeling) or a cool sensation (coolness and refreshing feeling), that is, a cool feeling effect to the human skin, mouth, nose, and throat has been used in tooth pastes, confections (for example, chewing gums, candies and the like), tobaccos, poultices, cosmetics, etc. As a flavor substance and/or a fragrance substance which gives such a refresh feeling or coolness and refreshing feeling, 1-menthol has been widely used currently. However, it has disadvantages that the cool feeling effect thereof lacks persistence, and when the using amount thereof is increased, the cool feeling effect is enhanced, but bitterness sometimes accompanies.

As a compound having a cool feeling effect, other than 1-menthol, many compounds have been proposed and used. Examples of the compounds which have a cool feeling effect and have been proposed conventionally other than 1-menthol include 3-substituted-p-menthane (see, for example, PTL 1), N-substituted-p-menthane-3-carboxamide (see, for example, PTL 2 and PTL 3), 1-menthyl glucoside (see, for example, PTL 4), 3-(1-menthoxy)propan-1,2-diol (see, for example, PTL 5), 1-menthyl-3-hydroxybutyrate (see, for example, PTL 6), 1-alkoxy-3-(1-menthoxy)propan-2-ol (see, for example, PTL 7), 3-hydroxymethyl-p-menthane esters (see, for example, PTL 8), N-acetylglycine menthane methyl ester (see, for example, PTL 9), l-isopulegol (see, for example, PTL 10), (2S)-3-{(1R,2S,5R)-[5-methyl-2-(1-methylethyl)cyclohexyl]oxy}-1,2-propanediol (see, for example, PTL 11), 2-hydroxymethyl menthol (see, for example, PTL 12), menthoxyalkane-1-ol (see, for example, PTL 13), (1-menthyloxyalkoxy)alkanol (see, for example, PTL 14), N-substituted-p-menthanecarboxamides (see, for example, PTL 15 and PTL 16), N-α-(menthanecarbonyl) amino acid amide (see, for example, PTL 17), and isopulegol derivatives (see, for example, PTL 18)

CITATION LIST

Patent Literature

PTL 1: JP-A-47-16647
PTL 2: JP-A-47-16648
PTL 3: JP-A-2007-530689
PTL 4: JP-A-48-33069
PTL 5: JP-A-58-88334
PTL 6: JP-A-61-194049
PTL 7: JP-A-2-290827
PTL 8: JP-A-5-255186
PTL 9: JP-A-5-255217
PTL 10: JP-A-6-65023
PTL 11: JP-A-7-82200
PTL 12: JP-A-7-118119
PTL 13: JP-A-2001-294546
PTL 14: JP-A-2005-343915
PTL 15: JP-A-2007-511546
PTL 16: JP-T-2011-530608
PTL 17: JP-A-2008-115181
PTL 18: WO 2013/033501
PTL 19: GB-A-1392907
PTL 20: DE-A1-102012202885
PTL 21: U.S. Pat. No. 4,157,384
PTL 22: U.S. Pat. No. 3,111,127
PTL 23: JP-A-11-158107
PTL 24: JP-A-52-105223
PTL 25: JP-A-2013-189623

Non Patent Literature

NPL 1: "Published collection of well-known prior arts (Flavor and Fragrance), Part 1, Jan. 29, 1999, Published by Japan Patent Office
NPL 2: Tetrahedron 1986, Vol. 42, No. 8, p. 2203-2209
NPL 3: J. Chem. Soc. Perkin Trans. 2, (1991): 1541-1543
NPL 4: J. Mol. Cat. A (1996), No. 109, 201-208
NPL 5: J. Am. Chem. Soc. (2004), Vol. 126, No. 41, 13312-13319
NPL 6: J. Vis. Exp. (2011), No. 54, 3149

SUMMARY OF INVENTION

Technical Problem

However, the above-mentioned conventionally proposed cooling agents have a certain level of cool feeling effect, but are not yet sufficiently satisfactory for persistence of the cool feeling effect or the like. In addition, also the sensory stimulating effect is needed to be further improved.

Therefore, an object of the present invention is to provide a novel methyl menthol derivative which does not have unfavorable stimulation, a peculiar smell, bitterness, etc., and can be used as a cooling agent or a sensory stimulant having excellent persistence of a refresh feeling or coolness and refreshing feeling.

Further, another object of the present invention is to provide a cooling agent composition containing the novel methyl menthol derivative and a sensory stimulant composition containing the cooling agent composition.

Further, still another object of the present invention is to provide a flavor composition and/or a fragrance composition containing the sensory stimulant composition blended therein and products containing the sensory stimulant composition or the flavor composition and/or the fragrance composition blended therein.

Solution to Problem

The present inventors conducted intensive studies to achieve the above objects, and as a result, they found that a 5,5-dimethyl-2-isopropylcyclohexane derivative or a 5,5-dimethyl-2-isopropenylcyclohexane derivative, which is a methyl menthol derivative represented by the general formula (1A) or the general formula (1B), has a strong cool feeling effect, and also has excellent persistence thereof, and is useful as a cool feeling substance and further as a sensory stimulating substance. In addition, they found that, for example, in the case where 1-menthol is used as a cooling agent, the methyl menthol derivative can reduce the irritating smell of 1-menthol. Moreover, they found that in a flavor composition and/or a fragrance composition containing a sensory stimulant composition containing a cooling agent composition containing a methyl menthol derivative represented by the general formula (1A) or the general formula (1B), the top note and lingering scent of the flavor composition and/or the fragrance composition are enhanced, and also a high scent quality improving effect is imparted to products scented with the flavor composition and/or the fragrance composition, and completed the present invention based on these findings.

That is, the present invention relates to the following [1] to [17].

[1]

A cooling agent composition, containing a methyl menthol derivative represented by the following general formula (1A) or the following general formula (1B).

[Chem. 1]

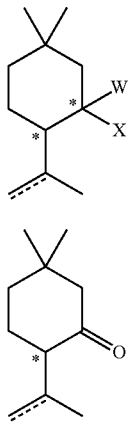

[In the formulae, a double line composed of a solid line and a dotted line is a double bond or a single bond, and a symbol * is an asymmetric carbon atom, W is a hydrogen atom, or forms a ring with X via a single bond or an oxygen atom, X represents —CHO, —CO—Y or —O—Z, Y is a group represented by the following formula (i) or formula (ii):

(i) $NR^1R^2$ or (ii) $OR^3$ (in the formula (i) and the formula (ii), $R^1$ to $R^3$ are each independently a hydrogen atom, a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent), and Z is a group represented by the following formula (iii) or formula (vi):

(iii) $R^4$ or (vi) $COR^5$ (in the formula (iii), $R^4$ is a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent, and in the formula (vi), $R^5$ is a hydrogen atom, a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent).]

[2]

The cooling agent composition according to [1] above, in which the methyl menthol derivative is a (2S)-form.

[3]

The cooling agent composition according to [1] or [2] above, further containing at least one kind of cool feeling substance other than the methyl menthol derivative.

[4]

The cooling agent composition according to [3] above, in which the cool feeling substance other than the methyl menthol derivative is at least one cool feeling substance selected from the group consisting of:

one or more kinds of compounds selected from menthol, menthone, camphor, pulegol, isopulegol, cineole, cubenol, menthyl acetate, pulegyl acetate, isopulegyl acetate, menthyl salicylate, pulegyl salicylate, isopulegyl salicylate, 3-(1-menthoxy)propan-1,2-diol, 2-methyl-3-(1-menthoxy)propan-1,2-diol, 2-(1-menthoxy)ethan-1-ol, 3-(1-menthoxy)propan-1-ol, 4-(1-menthoxy)butan-1-ol, menthyl 3-hydroxybutanoate, menthyl glyoxylate, p-menthane-3,8-diol, 1-(2-hydroxy-4-methylcyclohexyl)ethanone, menthyl lactate, menthone glycerin ketal, menthyl-2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkaline earth metal salts of monomenthyl glutarate, N-[[5-methyl-2-(1-methylethyl)cyclohexyl]carbonyl]glycine, p-menthane-3-carboxylic acid glycerol ester, menthol propylene glycol carbonate, menthol ethylene glycol carbonate, p-menthane-2,3-diol, 2-isopropyl-N,2,3-trimethylbutanamide, N-ethyl-p-menthane-3-carboxamide, ethyl 3-(p-menthane-3-carboxamide)acetate, N-(4-methoxyphenyl)-p-menthanecarboxamide, N-ethyl-2,2-diisopropylbutanamide, N-cyclopropyl-p-menthanecarboxamide, N-(4-cyanomethylphenyl)-p-menthanecarboxamide, N-(2-pyridin-2-yl)-3-p-menthanecarboxamide. N-(2-hydroxyethyl)-2-isopropyl-2,3-dimethylbutanamide, N-(1,1-dimethyl-2-hydroxyethyl)-2,2-diethylbutanamide, cyclopropanecarboxylic acid (2-isopropyl-5-methylcyclohexyl)amide, N-ethyl-2,2-diisopropylbutanamide, N-[4-(2-amino-2-oxoethyl)phenyl]-p-menthanecarboxamide, 2-[(2-p-menthoxy)ethoxy]ethanol, 2,6-diethyl-5-isopropyl-2-methyltetrahydropyran, and trans-4-tert-butylcyclohexanol;

one or more kinds of sugar alcohols selected from xylitol, erythritol, dextrose, and sorbitol; and one or more kinds of natural products selected from Japanese mint oil, peppermint oil, spearmint oil, and *eucalyptus* oil.

[5]

A sensory stimulant composition, containing the cooling agent composition described in any one of [1] to [4] above.

[6]
The sensory stimulant composition according to [5] above, further containing at least one kind of warm feeling substance.

[7]
The sensory stimulant composition according to [6] above, in which the warm feeling substance is at least one warm feeling substance selected from the group consisting of:

one or more kinds of compounds selected from vanillyl methyl ether, vanillyl ethyl ether, vanillyl propyl ether, vanillyl isopropyl ether, vanillyl butyl ether, vanillyl amyl ether, vanillyl isoamyl ether, vanillyl hexyl ether, isovanillyl methyl ether, isovanillyl ethyl ether, isovanillyl propyl ether, isovanillyl isopropyl ether, isovanillyl butyl ether, isovanillyl amyl ether, isovanillyl isoamyl ether, isovanillyl hexyl ether, ethyl vanillyl methyl ether, ethyl vanillyl ethyl ether, ethyl vanillyl propyl ether, ethyl vanillyl isopropyl ether, ethyl vanillyl butyl ether, ethyl vanillyl amyl ether, ethyl vanillyl isoamyl ether, ethyl vanillyl hexyl ether, vanillin propylene glycol acetal, isovanillin propylene glycol acetal, ethyl vanillin propylene glycol acetal, vanillyl butyl ether acetic acid ester, isovanillyl butyl ether acetic acid ester, ethyl vanillyl butyl ether acetic acid ester, 4-(1-menthoxymethyl)-2-(3'-methoxy-4'-hydroxyphenyl)-1,3-dioxolane, 4-(1-menthoxymethyl)-2-(3'-hydroxy-4'-methoxyphenyl)-1,3-dioxolane, 4-(1-menthoxymethyl)-2-(3'-ethoxy-4'-hydroxyphenyl)-1,3-dioxolane, capsaicin, dihydrocapsaicin, nordihydrocapsaicin, homodihydrocapsaicin, homocapsaicin, biscapsanthin, trishomocapsanthin, nomorcapsanthin, norcapsanthin, capsaicinol, vanillyl caprylamide (octylic acid vanillylamide), vanillyl pelargonamide (nonylic acid vanillylamide), vanillyl caproamide (decylic acid vanillylamide), vanillyl undecamide (undecylic acid vanillylamide), N-trans-feruloyltyramine, N-5-(4-hydroxy-3-methoxyphenyl)-2E,4E-pentadienoylpiperidine, N-trans-feruloylpiperidine, N-5-(4-hydroxy-3-methoxyphenyl)-2E-pentenoylpiperidine, N-5-(4-hydroxyphenyl)-2E,4E-pentadienoylpiperidine, piperine, isopiperine, chavicine, isochavicine, piperamine, piperettine, piperolein B, retrofractamide A, pipercide, guineenside, piperiline, piperamide C5:1 (2E), piperamide C7:1 (6E), piperamide C7:2 (2E,6E), piperamide C9:1 (8E), piperamide C9:2 (2E,8E), piperamide C9:3 (2E,4E,8E), fagaramide, sanshool-I, sanshool-II, hydroxysanshool, sanshoamide, gingerol, shogaol, zingerone, methylgingerol, paradol, spilanthol, chavicine, polygodial (tadeonal), isopolygodial, dihydropolygodial, and tadeon; and one or more kinds of natural products selected from *capsicum* oil, *capsicum* oleoresin, ginger oleoresin, jambu oleoresin (*Spilanthes oleracea* extract), sansho (*Zanthoxylum piperitum*) extract, sanshoamide, black pepper extract, white pepper extract, and *polygonum* extract.

[8]
A flavor composition and/or a fragrance composition, containing the sensory stimulant composition described in any one of [5] to [7] above.

[9]
A flavor composition and/or a fragrance composition, containing the sensory stimulant composition described in any one of [5] to [7] above in an amount of 0.00001 to 90 mass %.

[10]
A product, which is any product selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, and contains the sensory stimulant composition described in any one of [5] to [7] above.

[11]
A product, which is any product selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, and contains the sensory stimulant composition described in any one of [5] to [7] above in an amount of 0.00001 to 50 mass %.

[12]
A product, which is any product selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, and contains the flavor composition and/or the fragrance composition described in [8] or [9] above.

[13]
A product, which is any product selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, and contains the flavor composition and/or the fragrance composition described in [8] or [9] above in an amount of 0.00001 to 50 mass %.

[14]
A method for producing a product, which is any product selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, in which the method includes blending the sensory stimulant composition described in any one of [5] to [7] above.

[15]
A method for producing a product, which is any product selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, in which the method includes blending the flavor composition and/or the fragrance composition described in [8] or [9] above.

[16]
A methyl menthol derivative represented by the following general formula (1A').

[Chem. 2]

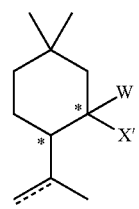

(1A')

[In the formula, a double line composed of a solid line and a dotted line is a double bond or a single bond, and a symbol * is an asymmetric carbon atom, W is a hydrogen atom, or forms a ring with X' via a single bond or an oxygen atom, X' represents —CHO, —CO—Y' or —O—Z, Y' is a group represented by the following formula (i) or formula (ii'):

(i) $NR^1R^2$ or
(ii') $OR^{3'}$ (in the formula (i), $R^1$ and $R^2$ are each independently a hydrogen atom, a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent, and in the formula (ii'), $R^{3'}$ is a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent), and Z is a group represented by the following formula (iii) or formula (vi):

(iii) $R^4$ or
(vi) $COR^5$ (in the formula (iii), $R^4$ is a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent, and in the formula (vi), $R^5$ is a hydrogen atom, a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent).]

[17]

The methyl menthol derivative according to [16] above, in which the methyl menthol derivative is a (2S)-form.

Advantageous Effects of Invention

The methyl menthol derivative of the present invention does not have unfavorable stimulation, a peculiar smell, bitterness, etc., and can impart a highly persistent refresh feeling or coolness and refreshing feeling to a variety of products by being blended in the products. In addition, the methyl menthol derivative exhibits an excellent property that it hardly causes unfavorable skin irritation to the human body. Further, it is not colored also during storage, and therefore is a compound having excellent storage stability.

DESCRIPTION OF EMBODIMENTS

Hereinafter, the present invention will be described in detail, however, the present invention is not limited to the following embodiments, and may be modified and implemented as appropriate without departing from the gist of the present invention. Further, in this description, the "compound represented by the formula (X)" is sometimes simply referred to as "compound (X)".

In this description, "wt %" and "mass %" have the same meaning. Further, when a unit "ppm" is described, it denotes "wt. ppm". Further, the expression "to" showing a numerical range is used to include the numerical values described therebefore and thereafter as the lower limit value and the upper limit value.

The cooling agent composition according to the present invention is characterized by containing a 5,5-dimethyl-2-isopropylcyclohexane derivative or a 5,5-dimethyl-2-isopropenylcyclohexane derivative, which is a novel methyl menthol derivative represented by the following general formula (1A) (hereinafter also referred to as "methyl menthol derivative (1A)") or a novel methyl menthol derivative represented by the following general formula (1B) (hereinafter also referred to as "methyl menthol derivative (1B)") as a cool feeling substance.

[Chem. 3]

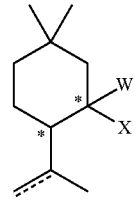

(1A)

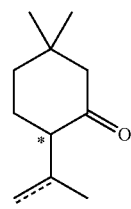

(1B)

[In the formulae, a double line composed of a solid line and a dotted line is a double bond or a single bond, and a symbol * is an asymmetric carbon atom, W is a hydrogen atom, or forms a ring with X via a single bond or an oxygen atom, X represents —CHO, —CO—Y or —O—Z, Y is a group represented by the following formula (i) or formula (ii):

(i) $NR^1R^2$ or
(ii) $OR^3$ (in the formula (i) and the formula (ii), $R^1$ to $R^3$ are each independently a hydrogen atom, a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent), and Z is a group represented by the following formula (iii) or formula (vi):

(iii) $R^4$ or (vi) $COR^5$ (in the formula (iii), $R^4$ is a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent, and in the formula (vi), $R^5$ is a hydrogen atom, a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent).]

The methyl menthol derivative represented by the general formula (1A) has a cyclohexane ring structure and has asymmetric carbon at positions 1 and 2 as shown in the following formula.

[Chem. 4]

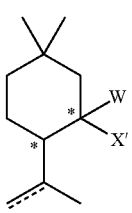

(1A)

(In the formula, a double line composed of a solid line and a dotted line, a symbol *, W, and X have the same definitions as described above.)

Specifically, as the methyl menthol derivative represented by the general formula (1A), there are four kinds of diastereomers represented by the following formula (1-1) to formula (1-4).

[Chem. 5]

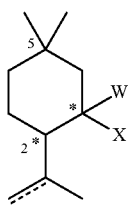

(1-1)

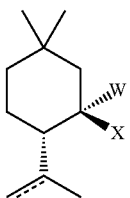

(1-2)

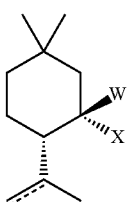

(1-3)

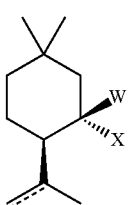

(1-4)

(In the formulae, a double line composed of a solid line and a dotted line, W, and X have the same definitions as described above.)

The methyl menthol derivative represented by the general formula (1A) is preferably an optically active substance, more preferably a (2S)-form, and particularly preferably a (1R,2S)-form. Further, also the methyl menthol derivative represented by the general formula (1B) is preferably a (2S)-form.

Among the methyl menthol derivatives represented by the general formula (1A), a methyl menthol derivative represented by the following general formula (1A') (hereinafter also referred to as "methyl menthol derivative (1A')") is a previously unknown novel 5,5-dimethyl-2-isopropylcyclohexane derivative compound or 5,5-dimethyl-2-isopropenylcyclohexane derivative compound.

[Chem. 6]

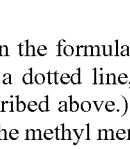

(1A')

[In the formula, a double line composed of a solid line and a dotted line is a double bond or a single bond, and a symbol * is an asymmetric carbon atom, W is a hydrogen atom, or forms a ring with X' via a single bond or an oxygen atom, X' represents —CHO, —CO—Y' or —O—Z, Y' is a group represented by the following formula (i) or formula (ii'):

(i) $NR^1R^2$ or (ii') $OR^{3'}$ (in the formula (i), $R^1$ and $R^2$ are each independently a hydrogen atom, a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent, and in the formula (ii'), $R^{3'}$ is a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent), and Z is a group represented by the following formula (iii) or formula (vi):

(iii) $R^4$ or (vi) $COR^5$ (in the formula (iii), $R^4$ is a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent, and in the formula (vi), $R^5$ is a hydrogen atom, a linear or branched alkyl group having a carbon number of 1 to 10 which may have a substituent, a linear or branched alkenyl group having a carbon number of 2 to 10 which may have a substituent, a cycloalkyl group having a carbon number of 3 to 10 which may have a substituent, an aryl group having a carbon number of 6 to 20 which may have a substituent, or a heterocyclic group having a carbon number of 2 to 15 which may have a substituent).]

The methyl menthol derivative represented by the general formula (1A') has a cyclohexane ring structure and has asymmetric carbon at positions 1 and 2 in the same manner as the methyl menthol derivative represented by the general formula (1A), and therefore, there are four kinds of diastereomers.

The methyl menthol derivative represented by the general formula (1A') is preferably an optically active substance, more preferably a (2S)-form, and particularly preferably a (1R,2S)-form.

The functional groups of the methyl menthol derivative represented by the general formula (1A), the general formula (1A') or the general formula (1B) will be described below.

Examples of the linear or branched alkyl group having a carbon number of 1 to 10 which may have a substituent include a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, and a decyl group.

Examples of the linear or branched alkenyl group having a carbon number of 2 to 10 which may have a substituent include a vinyl group, an allyl group, a 1-propenyl group, an isopropenyl group, a 1-butenyl group, a 2-butenyl group, a 3-butenyl group, a 2-methylallyl group, a pentenyl group, a hexenyl group, a heptenyl group, an octenyl group, a nonenyl group, and a decenyl group.

Examples of the cycloalkyl group having a carbon number of 3 to 10 which may have a substituent include a cyclopropyl group, a cyclobutyl group, a cyclopentyl group, a cyclohexyl group, a cycloheptyl group, a cyclooctyl group, a cyclononyl group, a cyclodecyl group, a cyclohexylcyclohexyl group, a decahydronaphtyl group, a norbornyl group, an adamantyl group, and an isobornyl group.

Examples of the aryl group having a carbon number of 6 to 20 which may have a substituent include an aromatic monocyclic group, an aromatic polycyclic group and an aromatic fused ring group having a carbon number of 6 to 20. Specific examples thereof include a phenyl group, a naphthyl group, an anthryl group, a phenanthryl group, and an indenyl group.

Examples of the heterocyclic group having a carbon number of 2 to 15 which may have a substituent include an aliphatic heterocyclic group and an aromatic heterocyclic group.

Examples of the aliphatic heterocyclic group include 3- to 8-membered cyclic, preferably 5- or 6-membered, monocyclic, polycyclic or fused ring aliphatic heterocyclic groups having a carbon number of 2 to 14 and containing at least one, preferably 1 to 3, heteroatoms. Examples of the heteroatom include hetero elements such as a nitrogen atom, an oxygen atom and a sulfur atom.

Specific examples of the aliphatic heterocyclic group include an oxiranyl group, an aziridinyl group, a 2-oxopyrrolidyl group, a piperidyl group, a piperadinyl group, a morpholino group, a tetrahydrofuryl group, a tetrahydropyranyl group, and a tetrahydrothienyl group.

On the other hand, examples of the aromatic heterocyclic group include 5- to 8-membered cyclic, preferably 5- or 6-membered, monocyclic, polycyclic or fused ring aromatic heterocyclic (heteroaryl) groups having a carbon number of 2 to 15 and containing at least one, preferably 1 to 3, heteroatoms. Examples of the heteroatom include hetero elements such as a nitrogen atom, an oxygen atom and a sulfur atom.

Specific examples of the aromatic heterocyclic group include a tetrazinyl group, a furyl group, a thienyl group, a pyridyl group, a pyridinyl group, a pyrazinyl group, a pyradazinyl group, an imidazoyl group, an oxazoyl group, a thiazoyl group, a benzofuryl group, a benzothienyl group, a quinolyl group, an isoquinolyl group, a quinoxanoyl group, a phthalazinyl group, a quinazolinyl group, a naphthylidinyl group, a cinnolinyl group, a benzimidazoline group, a benzoxazolyl group, and a benzothiazolyl group.

Examples of the substituent which may be included include alkyl groups having a carbon number of 1 to 6 such as a methyl group, an ethyl group, an n-propyl group, an isopropyl group, an n-butyl group, an isobutyl group, a sec-butyl group, a tert-butyl group, a pentyl group, and a hexyl group; cycloalkyl groups having a carbon number of 5 to 8 such as a cyclopentyl group, a cyclohexyl group and a cycloheptyl group; a hydroxy group; alkoxy groups having a carbon number of 1 to 4 such as a methoxy group, an ethoxy group, an n-propoxy group, an isopropoxy group, an n-butoxy group, an isobutoxy group, a sec-butoxy group, a methylenedioxy group, and a tert-butoxy group; halogen atoms such as a fluorine atom, a chlorine atom, a bromine atom, and an iodine atom; aralkyl groups having a carbon number of 7 to 12 such as a benzyl group, a phenylethyl group and a naphthylmethyl group; a carboxy group; alkoxycarbonyl groups having a carbon number of 2 to 8 such as a methoxycarbonyl group, an ethoxycarbonyl group and a benzyloxycarbonyl group; a carboxamide group; dialkylamino groups having a carbon number of 2 to 8 such as a dimethylamino group, a diethylamino group and a dibutylamino group; a nitrile group; cyanoalkyl groups (in which the alkyl group has a carbon number of 1 to 4) such as a cyanomethyl group, a cyanoethyl group, a cyanopropyl group, and a cyanobutyl group; aliphatic heterocyclic groups such as an oxiranyl group, an aziridinyl group, a 2-oxopyrropidyl group, a piperidyl group, a piperadinyl group, a morpholino group, a tetrahydrofuryl group, a tetrahydropyranyl group, and a tetrahydrothienyl group; and aromatic heterocyclic groups such as a tetrazinyl group, a furyl group, a thienyl group, a pyridyl group, a pyridinyl group, a pyrazinyl group, a pyradazinyl group, an imidazoyl group, an oxazoyl group, a thiazoyl group, a benzofuryl group, a benzothienyl group, a quinolyl group, an isoquinolyl group, a quinoxanoyl group, a phthalazinyl group, a quinazolinyl group, a naphthylidinyl group, a cinnolinyl group, a benzimidazoline group, a benzoxazolyl group, and a benzothiazolyl group.

In the case where W and X or X' are combined via a single bond or an oxygen atom to form a ring, a 5- to 6-membered ring which may have an oxygen atom can be formed.

Examples of the 5- to 6-membered ring which may have an oxygen atom include a furan ring, a tetrahydrofuran ring, a dioxolane ring, a dioxane ring, a trioxocyclohexane ring, a γ-butyrolactone ring, and a δ-pentalactone ring.

The methyl menthol derivative (1A), the methyl menthol derivative (1A') and the methyl menthol derivative (1B) of the present invention are synthesized, for example, by methods represented by the following Scheme 1 to Scheme 9. However, the synthesis method thereof is not limited to the methods of Scheme 1 to Scheme 9. In Scheme 1 to Scheme 9, an explanation will be given by taking the methyl menthol derivative (1A) as an example, however, the same applies to the synthesis methods of the methyl menthol derivative (1A') and the methyl menthol derivative (1B).

5,5-Dimethyl-2-(1-propen-2-yl)cyclohexanol represented by the following formula (4) and 2-isopropyl-5,5-dimethyl- cyclohexanol represented by the following formula (5), each of which is a basic structure of the methyl menthol derivative (1A) of the present invention are synthesized, for example, according to a method represented by the following Scheme 1 from citral, geranial, neral, piperitone, or isopiperitenone.

[Scheme 1]

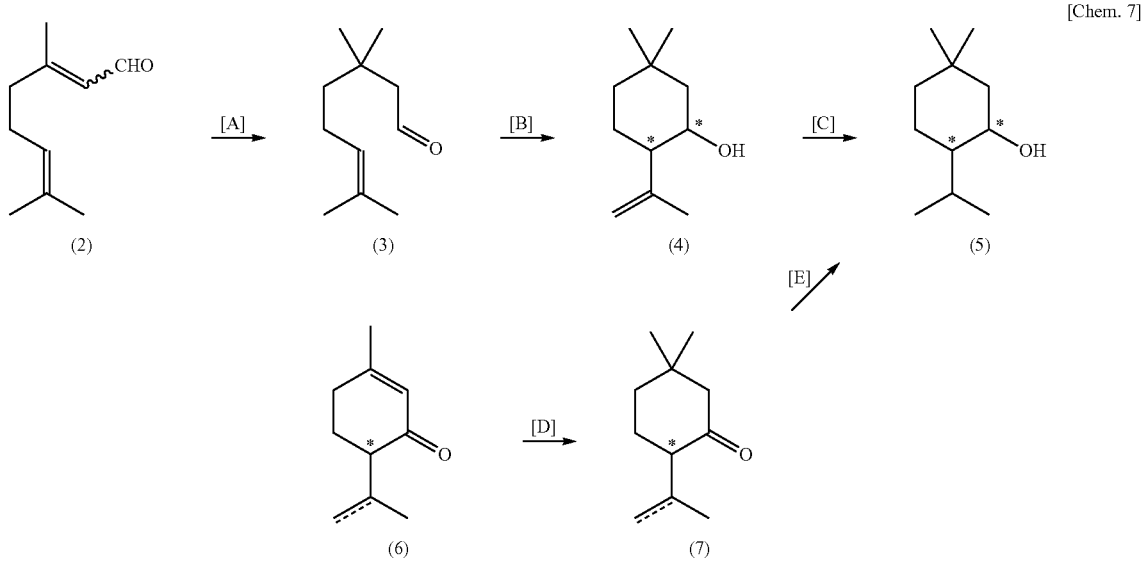

[Chem. 7]

(In the formulae, a double line composed of a solid line and a dotted line and a symbol * have the same definitions as described above.)

Step [A], Step [B] and Step [D] can be performed in the same manner as in NPL 2 (Tetrahedron 1986, Vol. 42, No. 8, p. 2230). That is, Step [A] can be performed by a conjugate addition (1,4-addition) reaction, Step [B] can be performed by an intramolecular Prins reaction, and Step [D] can be performed by a conjugate addition (1,4-addition) reaction. Further, Step [C] can be performed by hydrogenation using a commonly used metal catalyst such as nickel or palladium. Step [E] can be performed in the same manner as in NPL 4, that is, by a hydrogenation reaction.

Hereinafter, a compound (7a) and a compound (7b) are collectively referred to as "ketone compound represented by the general formula (7)" (hereinafter also referred to as "ketone compound (7)").

[Chem. 8]

(7a)

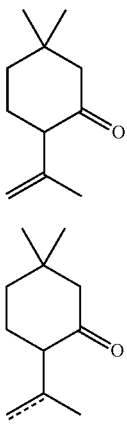

(7b)

(7)

(In the formulae, a double line composed of a solid line and a dotted line and a symbol * have the same definitions as described above.)

Further, hereinafter, a compound (4) and a compound (5) are collectively referred to as "alcohol compound represented by the general formula (8)" (hereinafter also referred to as "alcohol compound (8)").

[Chem. 9]

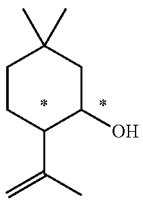

(4)

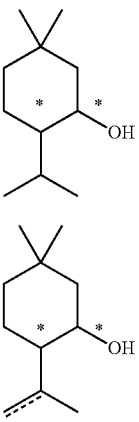

(5)

(8)

(In the formulae, a double line composed of a solid line and a dotted line and a symbol * have the same definitions as described above.)

Carboxylic acid compounds represented by the general formula (11) [5,5-dimethyl-2-isopropylcyclohexane carboxylic acid (11a) and 5,5-dimethyl-2-isopropenylcyclohexane carboxylic acid (11b)] (hereinafter also referred to as "carboxylic acid compound (11)") of the present invention are synthesized, for example, according to a method represented by the following Scheme 2 from the alcohol compound (8) and the ketone compound (7).

On the other hand, aldehyde compounds represented by the general formula (13) [5,5-dimethyl-2-isopropylcyclohexane carbaldehyde (13a) and 5,5-dimethyl-2-isopropenyl-cyclohexane carbaldehyde (13b)] (hereinafter also referred to as "aldehyde compound (13)") are synthesized, for example, according to a method represented by the following Scheme 2 from the ketone compound (7).

[Scheme 2]

[Chem. 10]

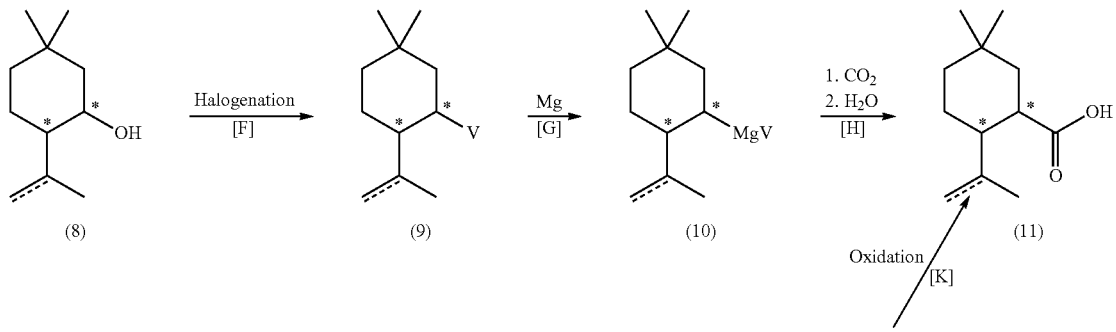

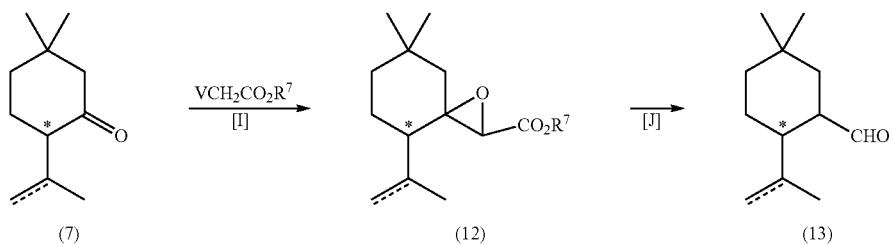

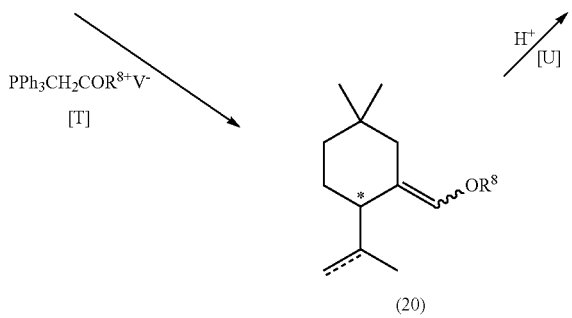

(20)

(In the formulae, a symbol * and a double line composed of a solid line and a dotted line have the same definitions as described above, $R^7$ and $R^8$ are each a linear or branched alkyl group having a carbon number of 1 to 10 which may have a substituent, and V is a halogen atom.)

A halogenation reaction of Step [F] can synthesize, for example, a halide (9) (V=Cl) by performing a reaction with phosphorus pentachloride. Further, it can be performed in the same manner as in NPL 3 (J. Chem. Soc. Perkin Trans., (1990): 1275-1277). Step [G] and Step [H] can be performed in the same manner as in PTL 19. Step [I], Step [J] and Step [K] can be performed in the same manner as in PTL 20. Step [T] and Step [U] can be performed in the same manner as in NPL 5 (J. Am. Chem. Soc. (2004), Vol. 126, No. 41, 13312-13319).

Among the compounds represented by the general formula (1A) of the present invention, an amide compound represented by the general formula (14) in which W=H and X=CONR$^1$R$^2$ (hereinafter also referred to as "amide compound (14)") is synthesized, for example, according to a method represented by the following Scheme 3 from the carboxylic acid compound (11).

Step [L] can be performed in the same manner as in PTL 18.

Further, the amide compound (14) of the present invention can also be synthesized, for example, according to a method represented by the following Scheme 4 from the carboxylic acid compound (11).

[Scheme 4]

[Chem. 12]

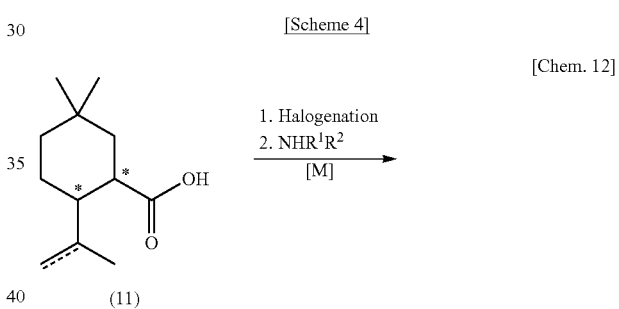

[Scheme 3]

[Chem. 11]

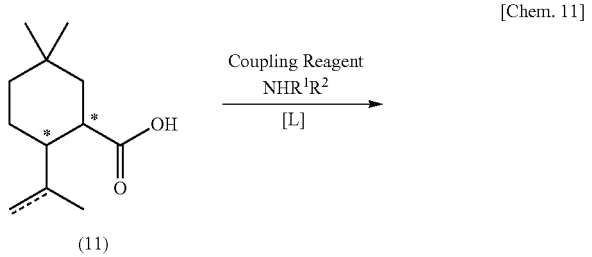

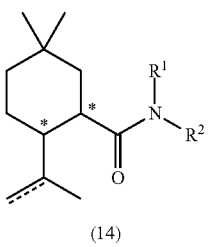

(14)

(In the formulae, a double line composed of a solid line and a dotted line, a symbol *, $R^1$ and $R^2$ have the same definitions as described above.)

(In the formulae, a double line composed of a solid line and a dotted line, a symbol *, $R^1$ and $R^2$ have the same definitions as described above.)

Step [M] can be performed in the same manner as in PTL 2 or PTL 18.

Among the compounds represented by the general formula (1A) of the present invention, a carboxylic acid ester compound represented by the general formula (15) in which W=H and X=COOR$^3$ (hereinafter also referred to as "carboxylic acid ester compound (15)") is synthesized, for example, according to a method represented by the following Scheme 5 from the carboxylic acid compound (11).

[Scheme 5]

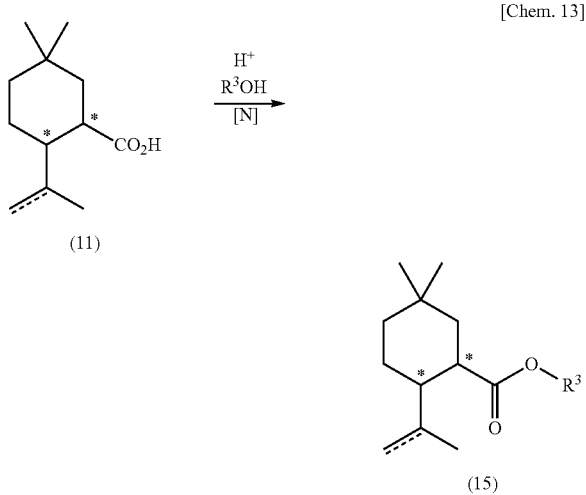

(In the formulae, a double line composed of a solid line and a dotted line, a symbol *, and $R^3$ have the same definitions as described above.)

Step [N] can be performed in the same manner as in PTL 21.

Among the compounds represented by the general formula (1A) of the present invention, a dicarboxylic acid monoester compound represented by the general formula (16) in which W=H and X=OCO(CH$_2$)$_n$COOH (hereinafter also referred to as "dicarboxylic acid monoester compound (16)") is synthesized, for example, according to a method represented by the following Scheme 6 from the alcohol compound (8).

[Scheme 6]

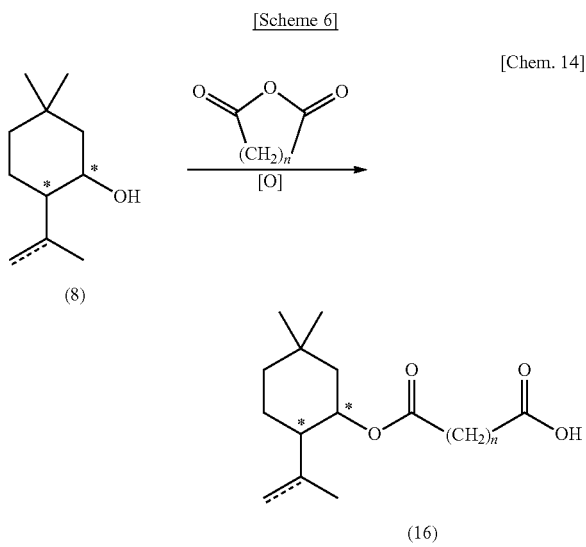

(In the formulae, a double line composed of a solid line and a dotted line and a symbol * have the same definitions as described above, and n is a natural number of 0 to 6.)

Step [O] can be performed in the same manner as in PTL 22.

Among the compounds represented by the general formula (1A) of the present invention, an ester compound represented by the general formula (17) in which W=H and X=OCOR$^5$ (hereinafter also referred to as "ester compound (17)") is synthesized, for example, according to a method represented by the following Scheme 7 from the alcohol compound (8).

[Scheme 7]

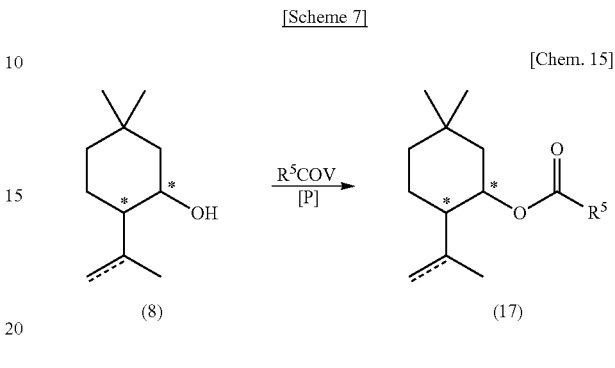

(In the formulae, a double line composed of a solid line and a dotted line, a symbol *, R$^5$, and V have the same definitions as described above.)

Step [P] can be performed in the same manner as in PTL 6.

Among the compounds represented by the general formula (1A) of the present invention, an ether compound represented by the general formula (18) in which W=H and X=OR$^4$ (hereinafter also referred to as "ether compound (18)") is synthesized, for example, according to a method represented by the following Scheme 8 from the alcohol compound (8).

[Scheme 8]

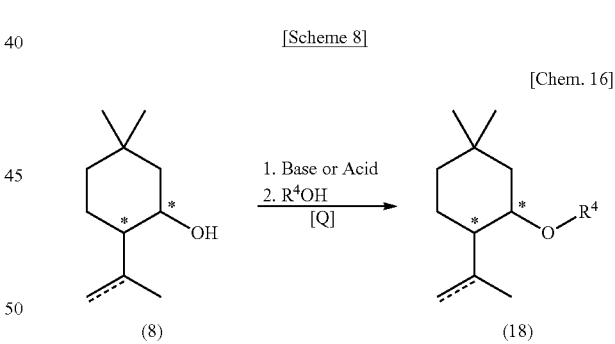

(In the formulae, a double line composed of a solid line and a dotted line, a symbol *, and R$^4$ have the same definitions as described above.)

Step [Q] can be performed in the same manner as in PTL 13.

Among the compounds represented by the general formula (1A) of the present invention, a ketal compound represented by the general formula (19) in which W and X are combined to form a ring represented by —OCH$_2$CHR$^6$(CH$_2$)$_m$O— (hereinafter also referred to as "ketal compound (19)") is synthesized, for example, according to a method represented by the following Scheme 9 from the alcohol compound (8).

[Scheme 9]

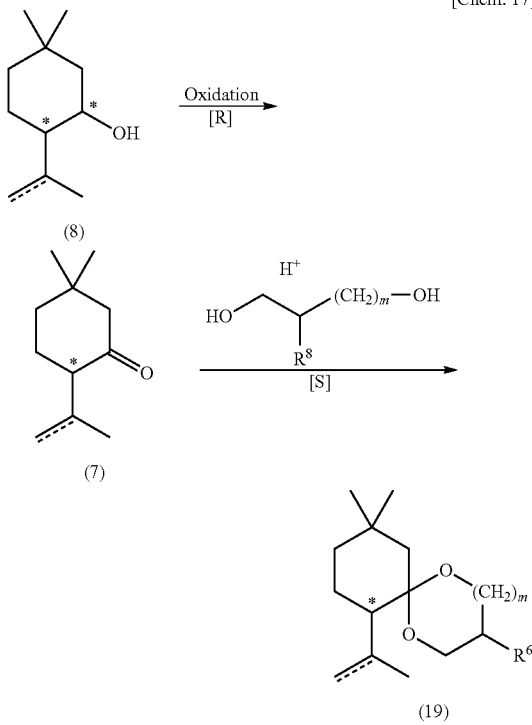

(In the formulae, a double line composed of a solid line and a dotted line and a symbol * have the same definitions as described above, m is a natural number of 0 to 6, and $R^6$ is a hydroxy group or a hydroxymethyl group.)

Step [R] can be performed in the same manner as in PTL 23. Step [S] can be performed in the same manner as in PTL 24.

Preferred specific examples of the methyl menthol derivative (1A) of the present invention include the carboxylic acid compound (11), the amide compound (14), the carboxylic acid ester compound (15), the dicarboxylic acid monoester compound (16), the ester compound (17), the ether compound (18), and the ketal compound (19), but are not limited thereto.

In the methyl menthol derivative (1A) of the present invention, preferred specific examples of the carboxylic acid compound (11) and the aldehyde compound (13) include the following compounds, but are not limited thereto.

In the following compounds, a symbol * represents asymmetric carbon.

[Chem. 18]

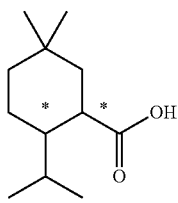

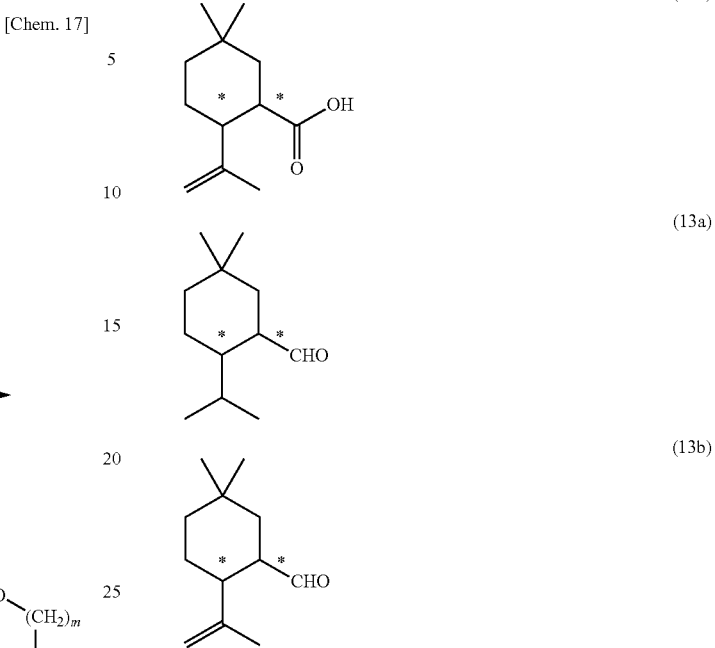

In the methyl menthol derivative (1A) of the present invention, preferred specific examples of the amide compound (14) include the following compounds, but are not limited thereto.

In the following compounds, Me represents a methyl group, Et represents an ethyl group, iPr represents an isopropyl group, and a symbol * represents asymmetric carbon.

[Chem. 19]

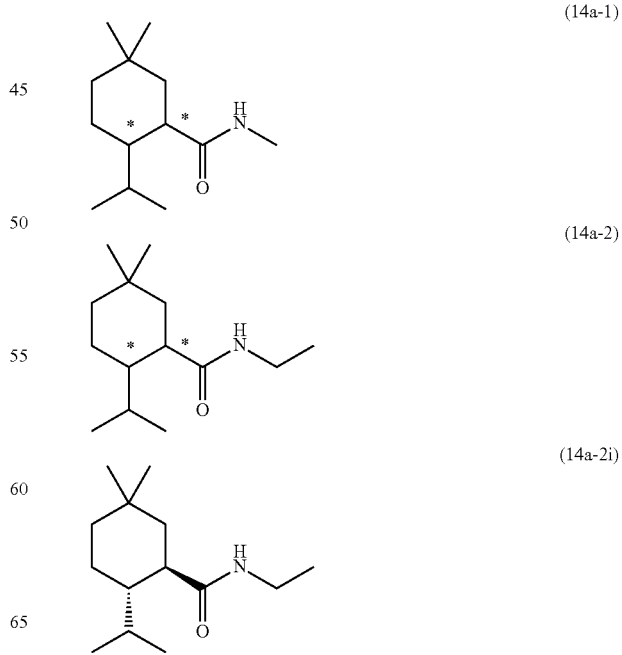

(14a-2ii)
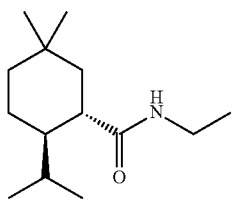
(14a-3)
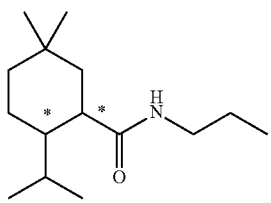
(14a-4)
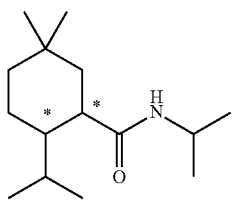
(14a-5)
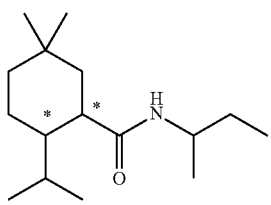
(14a-6)
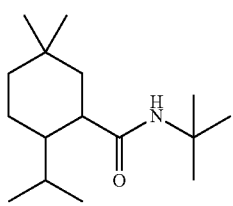
(14a-7)
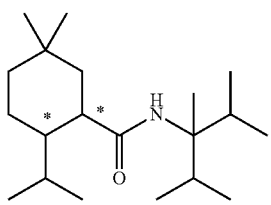
(14a-8)
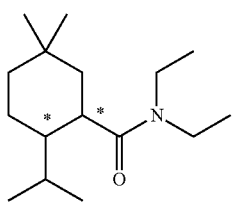
(14a-9)
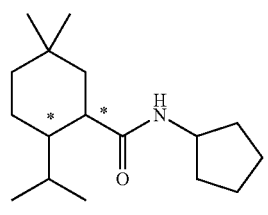
(14a-10)
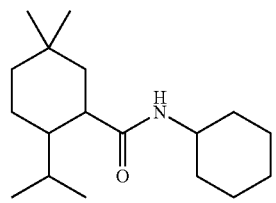
[Chem. 20]
(14a-11)
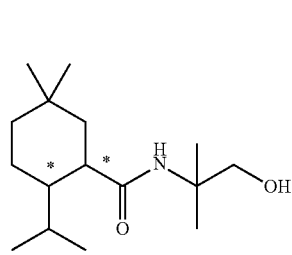
(14a-12)
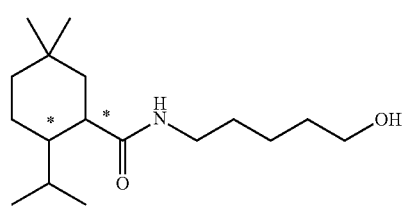
(14a-13)
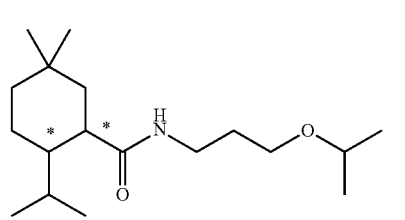
(14a-14)
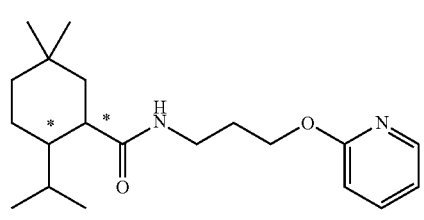
(14a-15)
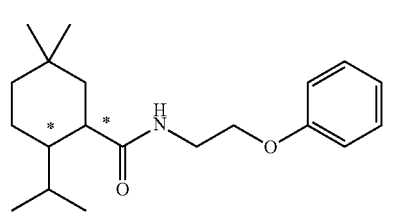

(14a-16)
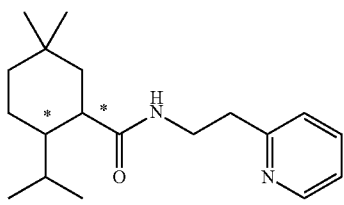
(14a-17)
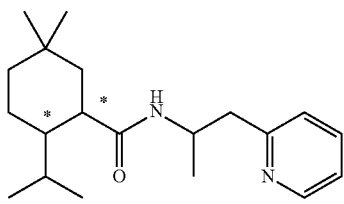
(14a-18)
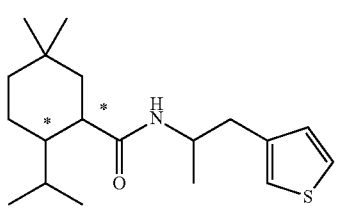
(14a-19)
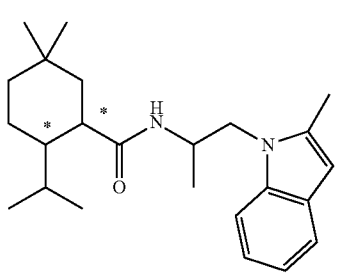
[Chem. 21]
(14a-20)
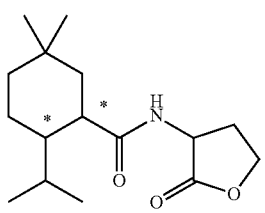
(14a-21)
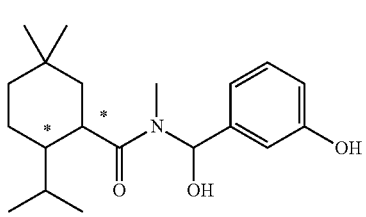
(14a-22)
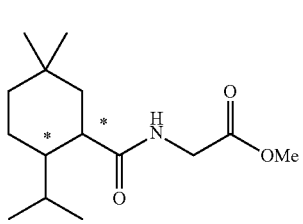
(14a-23)
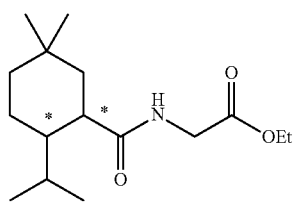
(14a-24)
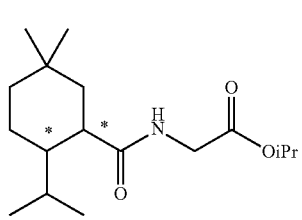
(14a-25i)
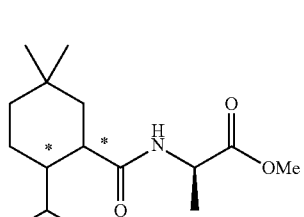
(14a-26i)
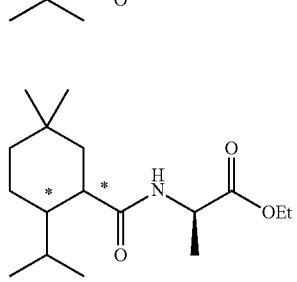
(14a-27ii)
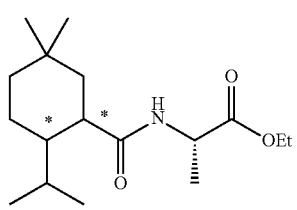
(14a-28)
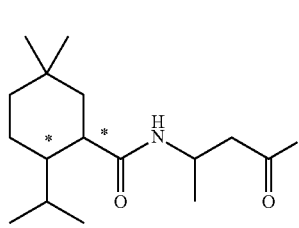
(14a-29)
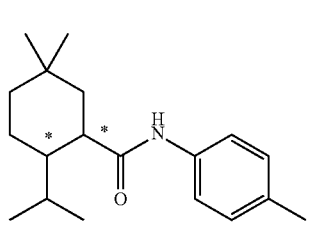

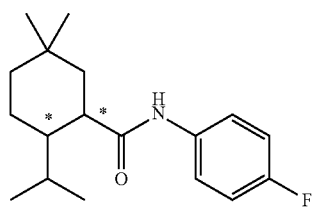
(14a-30)
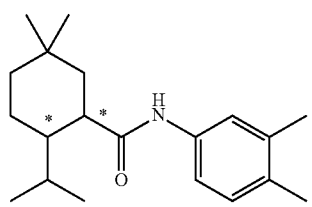
(14a-31)
[Chem. 22]
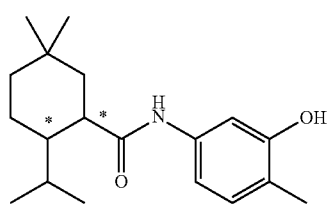
(14a-32)
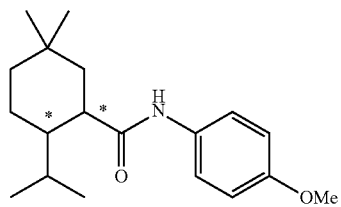
(14a-33)
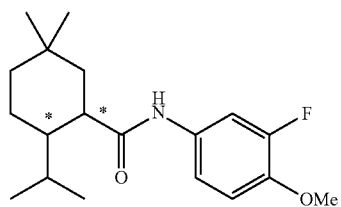
(14a-34)
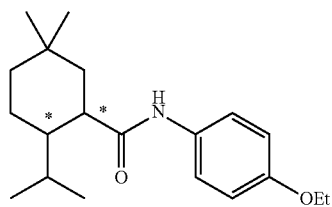
(14a-35)
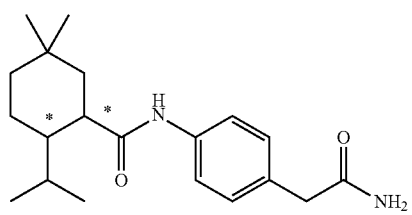
(14a-36)
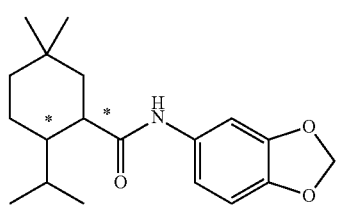
(14a-37)
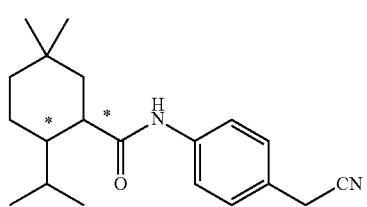
(14a-38)
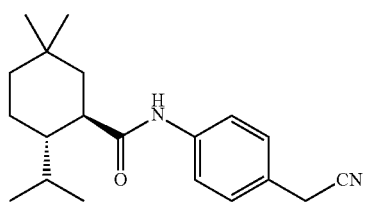
(14a-38i)
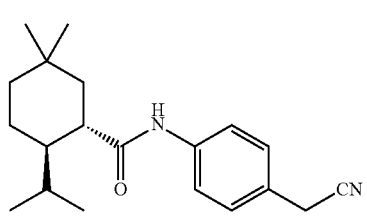
(14a-38ii)
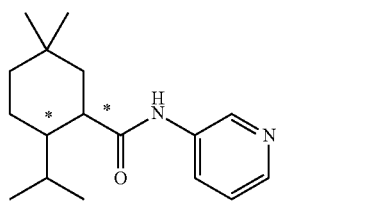
(14a-39)
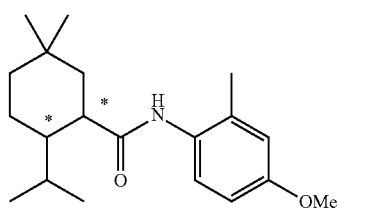
(14a-40)
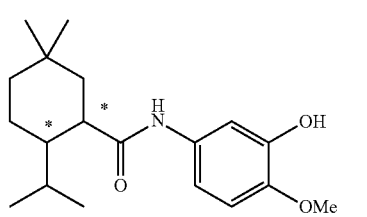
(14a-41)

(14a-42) 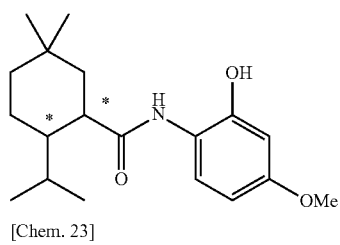
[Chem. 23]
(14a-43) 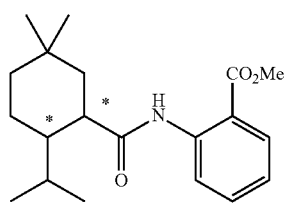
(14a-44) 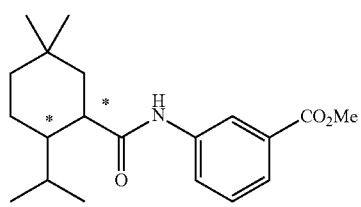
(14a-45) 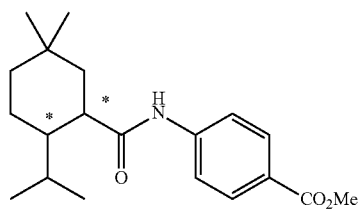
(14a-46) 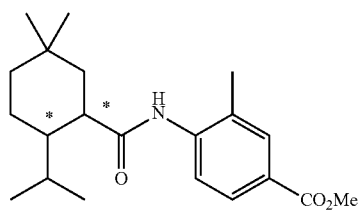
(14a-47) 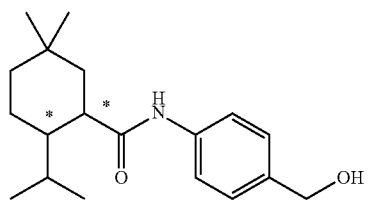
(14a-48) 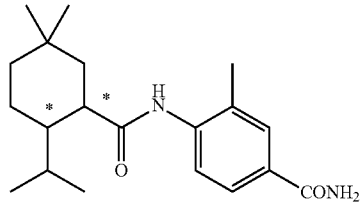
(14a-49) 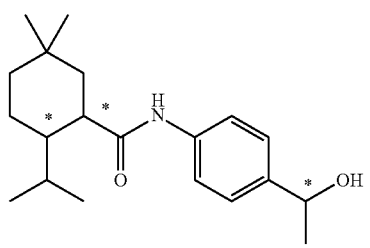
(14a-50) 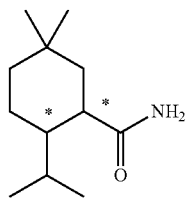
(14a-51) 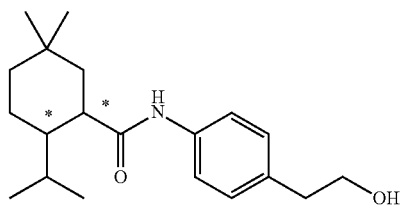
(14a-52) 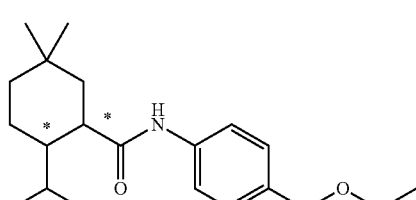
(14a-53) 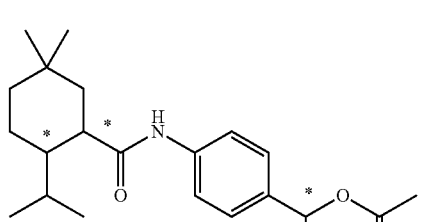
(14a-54) 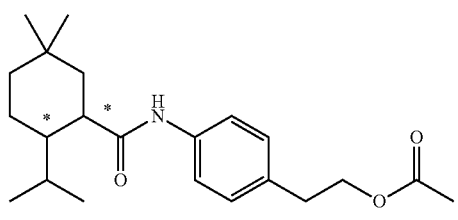

[Chem. 24]
(14b-1) 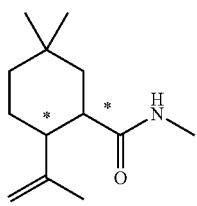
(14b-2) 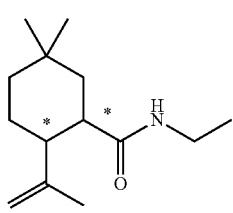
(14b-2i) 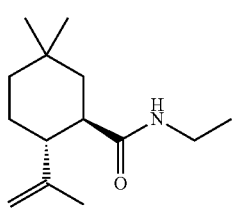
(14b-2ii) 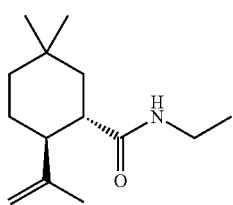
(14b-3) 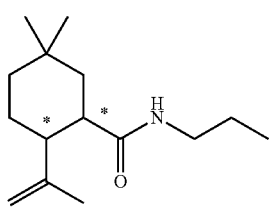
(14b-4) 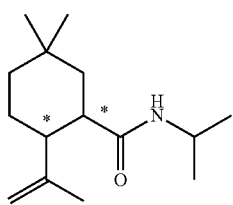
(14b-5) 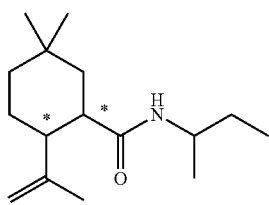
(14b-6) 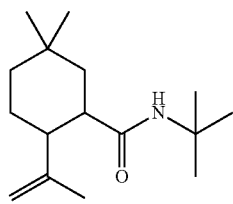
(14b-7) 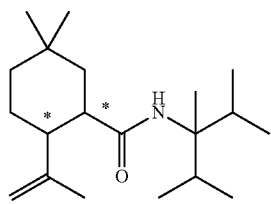
(14b-8) 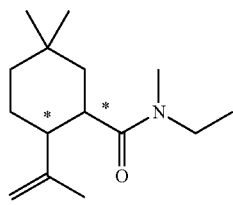
(14b-9) 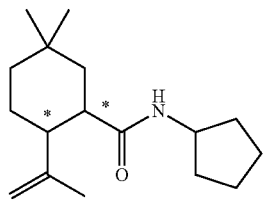
(14b-10) 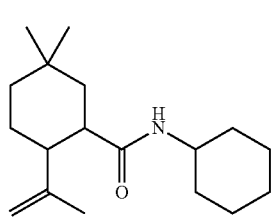
[Chem. 25]
(14b-11) 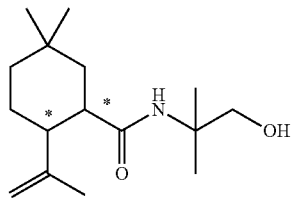
(14b-12) 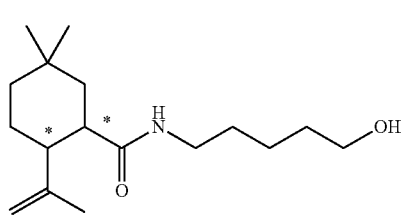

(14b-13) 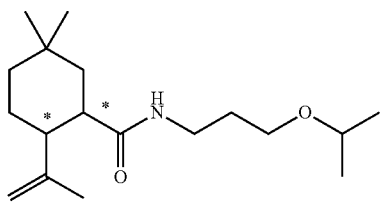
(14b-20) 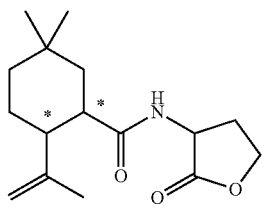
[Chem. 26]
(14b-14) 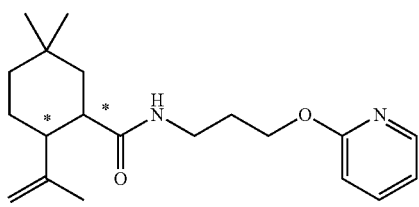
(14b-21) 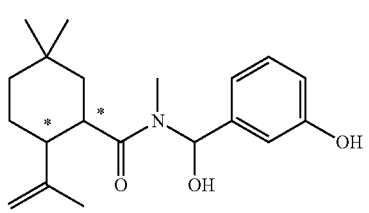
(14b-15) 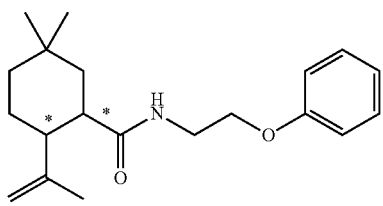
(14b-22) 
(14b-16) 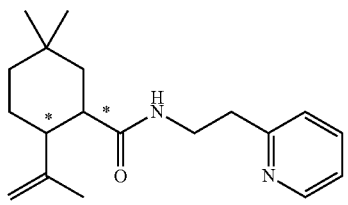
(14b-23) 
(14b-17) 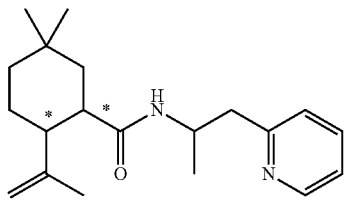
(14b-24) 
(14b-18) 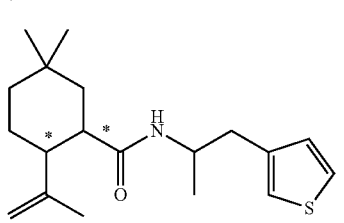
(14b-25i) 
(14b-19) 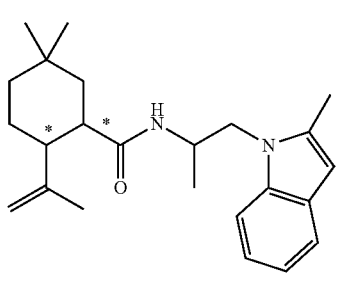
(14b-26i) 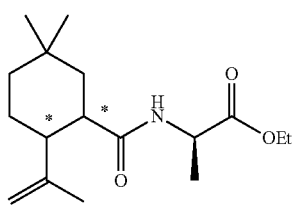

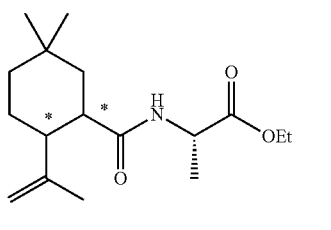 (14b-27ii)
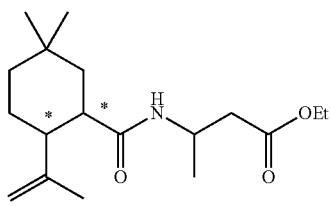 (14b-28)
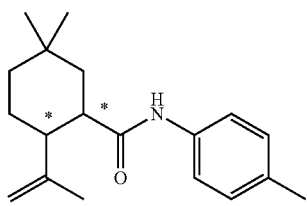 (14b-29)
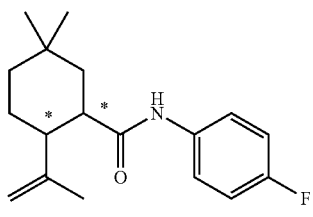 (14b-30)
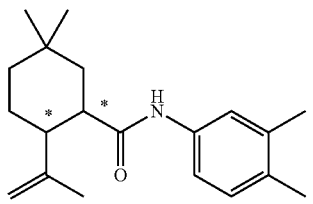 (14b-31)
[Chem. 27]
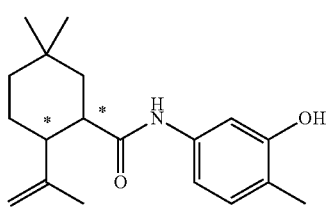 (14b-32)
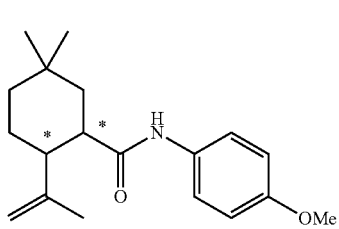 (14b-33)
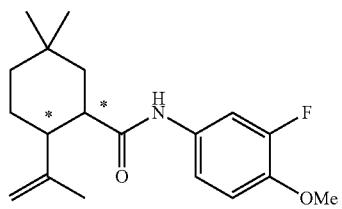 (14b-34)
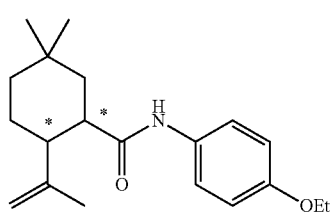 (14b-35)
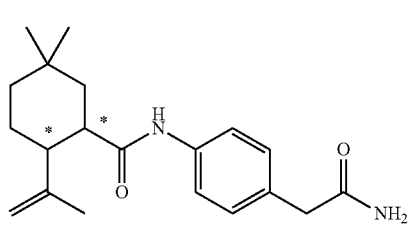 (14b-36)
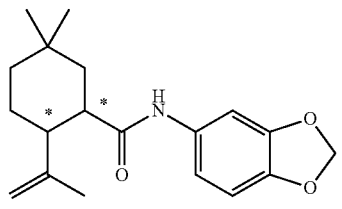 (14b-37)
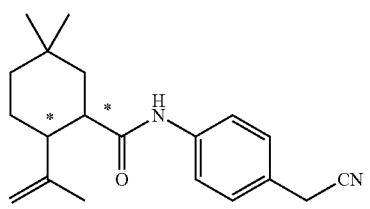 (14b-38)
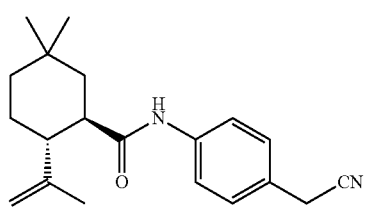 (14b-38i)
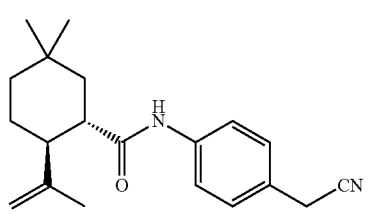 (14b-38i)

(14b-39) 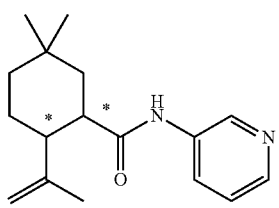
[Chem. 28]
(14b-40) 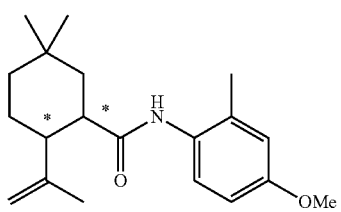
(14b-41) 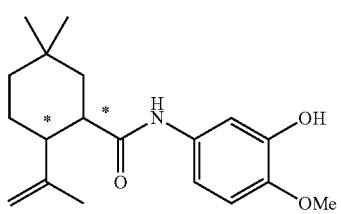
(14b-42) 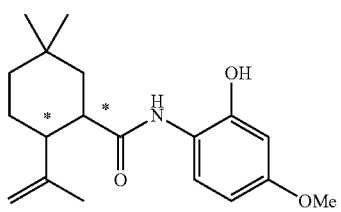
(14b-43) 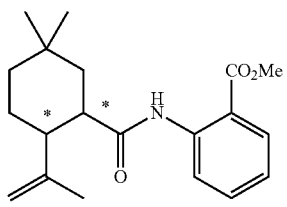
(14b-44) 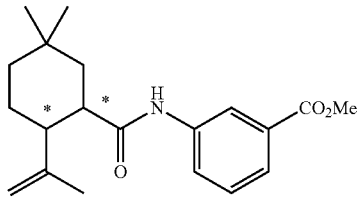
(14b-45) 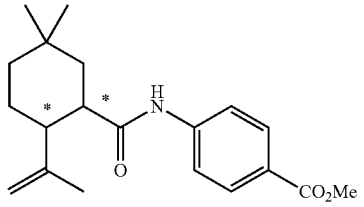
(14b-46) 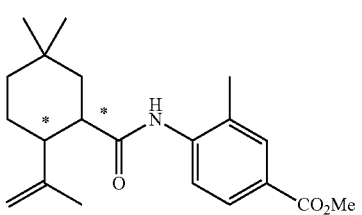
(14b-47) 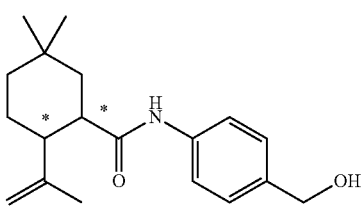
(14b-48) 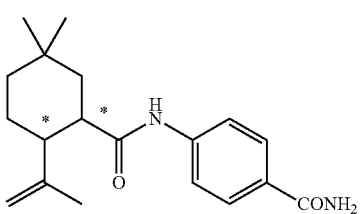
In the methyl menthol derivative (1A) of the present invention, preferred specific examples of the carboxylic acid ester compound (15) include the following compounds, but are not limited thereto.
In the following compounds, a symbol * represents asymmetric carbon.
[Chem. 29]
(11a) 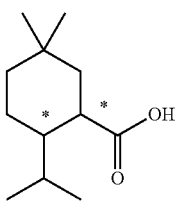
(15a-1) 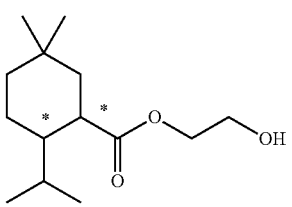
(15a-2) 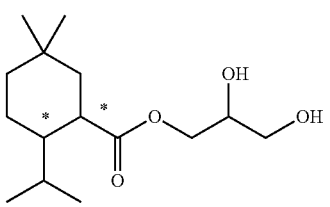

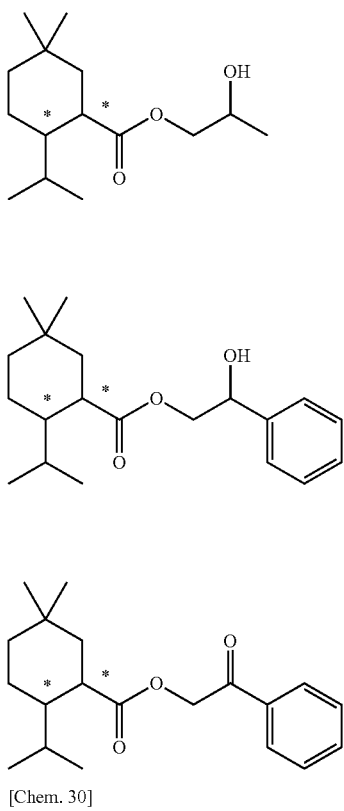
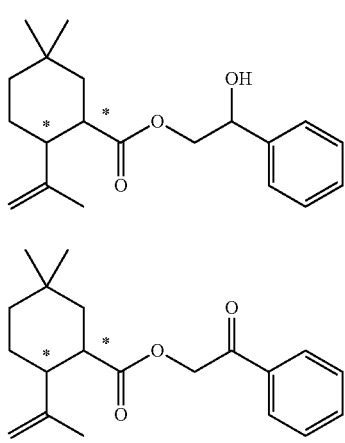
In the methyl menthol derivative (1A) of the present invention, preferred specific examples of the dicarboxylic acid monoester compound (16) include the following compounds, but are not limited thereto.
In the following compounds, a symbol * represents asymmetric carbon.
[Chem. 31]
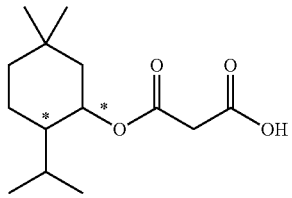
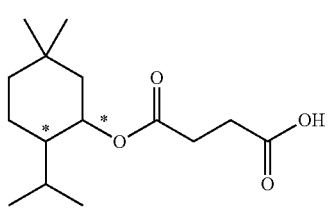
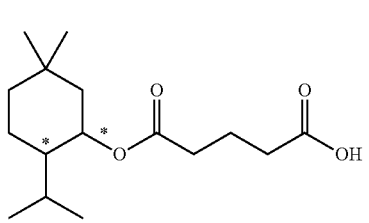
[Chem. 32]
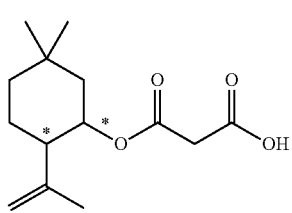

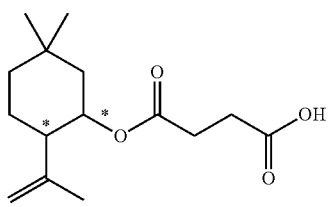
(16b-2)
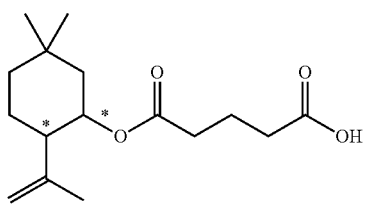
(16b-3)
In the methyl menthol derivative (1A) of the present invention, preferred specific examples of the ester compound (17) include the following compounds, but are not limited thereto.
In the following compounds, a symbol * represents asymmetric carbon.
[Chem. 33]
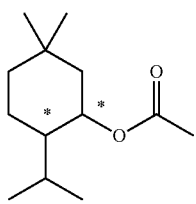
(17a-1)
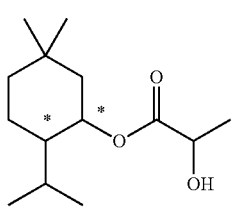
(17a-2)
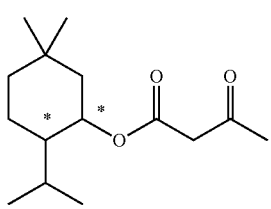
(17a-3)
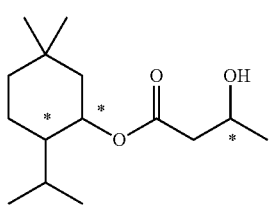
(17a-4)
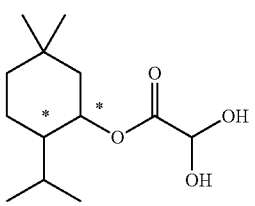
(17a-5)
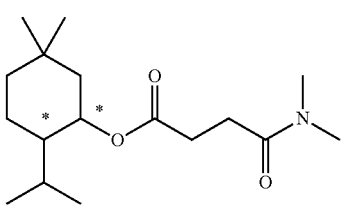
(17a-6)
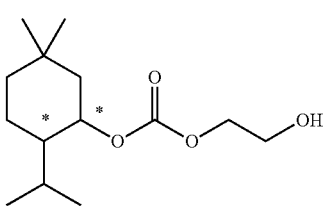
(17a-7)
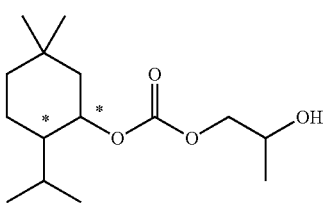
(17a-8)
[Chem. 34]
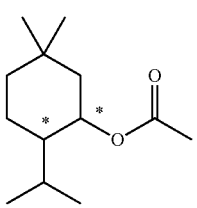
(17b-1)
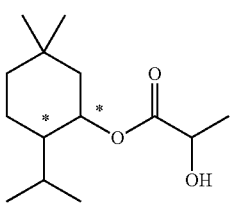
(17b-2)
(17b-3)

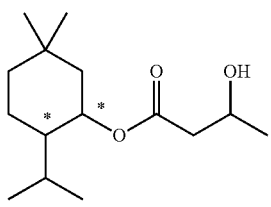 (17b-4)
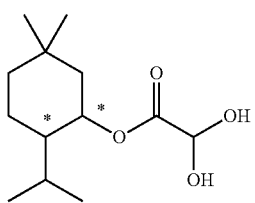 (17b-5)
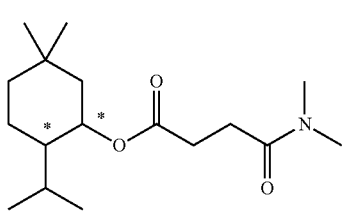 (17b-6)
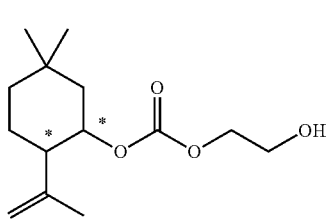 (17b-7)
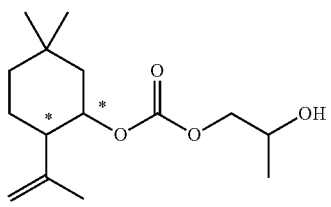 (17b-8)
In the methyl menthol derivative (1A) of the present invention, preferred specific examples of the ether compound (18) include the following compounds, but are not limited thereto.
In the following compounds, a symbol * represents asymmetric carbon.
[Chem. 35]
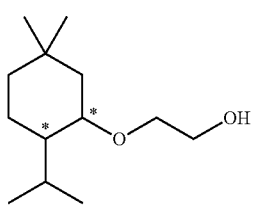 (18a-1)
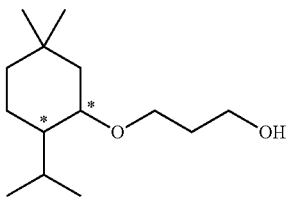 (18a-2)
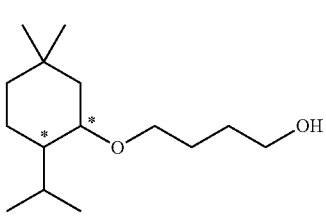 (18a-3)
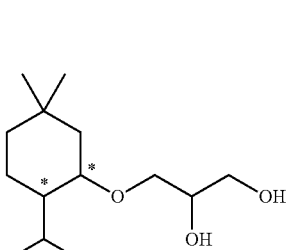 (18a-4)
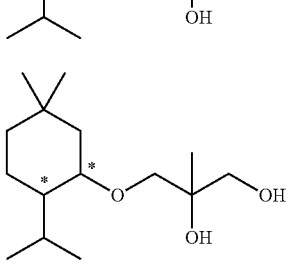 (18a-5)
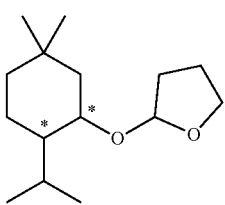 (18a-6)
[Chem. 36]
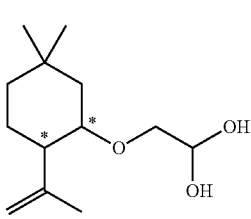 (18b-1)
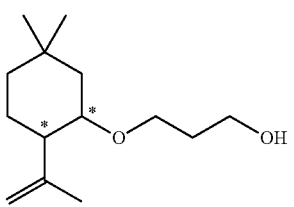 (18b-2)

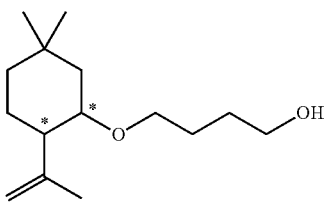 (18b-3)

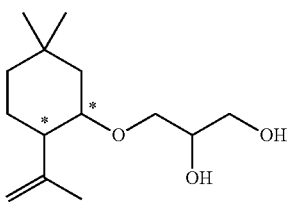 (18b-4)

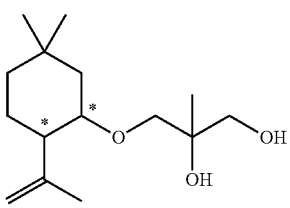 (18b-5)

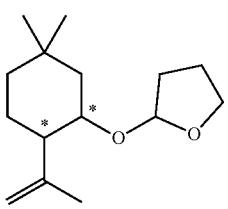 (18b-6)

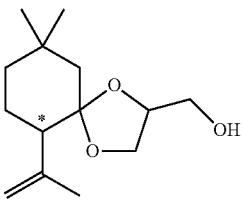 (19b-1)

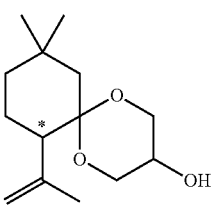 (19b-2)

In the methyl menthol derivative (1A) of the present invention, preferred specific examples of the ketal compound (19) include the following compounds, but are not limited thereto.

In the following compounds, a symbol * represents asymmetric carbon.

[Chem. 37]

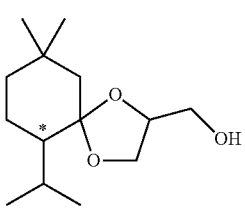 (19a-1)

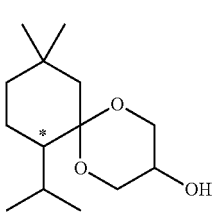 (19a-2)

The thus obtained methyl menthol derivative represented by the general formula (1A) or the general formula (1B) of the present invention has a strong and persistent cool feeling effect and can be used directly alone as a cooling agent or a sensory stimulant.

The methyl menthol derivative of the present invention requires to appropriately change its application range or application method in accordance with the type of product, intended use, etc., but in general, it is preferably used at a concentration of 0.00001 to 50 mass %, preferably 0.0001 to 20 mass %, and particularly preferably 0.001 to 5 mass % with respect to the total composition of the product.

In the cooling agent composition containing the methyl menthol derivative according to the present invention, by using at least one kind selected from cool feeling substances other than the methyl menthol derivative of the present invention in combination with the methyl menthol derivative of the present invention, a cooling agent composition with an increased cool feeling intensity can be formed. In addition, a sensory stimulant composition containing the cooling agent composition with an increased cool feeling intensity can be prepared.

Examples of the cool feeling substance which is not included in the methyl menthol derivative of the present invention include:

compounds (α) such as menthol, menthone, camphor, pulegol, isopulegol, cineole, cubenol, menthyl acetate, pulegyl acetate, isopulegyl acetate, menthyl salicylate, pulegyl salicylate, isopulegyl salicylate, 3-(1-menthoxy)propan-1,2-diol, 2-methyl-3-(1-menthoxy)propan-1,2-diol, 2-(1-menthoxy)ethan-1-ol, 3-(1-menthoxy)propan-1-ol, 4-(1-menthoxy)butan-1-ol, menthyl 3-hydroxybutanoate, menthyl glyoxylate, p-menthane-3,8-diol, 1-(2-hydroxy-4-methylcyclohexyl)ethanone, menthyl lactate, menthone glycerin ketal, menthyl-2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkaline earth metal salts of monomenthyl glutarate, N-[[5-methyl-2-(1-methylethyl)cyclohexyl]carbonyl]glycine, p-menthane-3-carboxylic acid glycerol ester, menthol propylene glycol carbonate, menthol ethylene glycol carbonate, p-menthane-2,3-diol, 2-isopropyl-N,2,3-trimethylbutanamide, N-ethyl-p-menthane-3-carboxamide, ethyl 3-(p-menthane-3-carboxamide)acetate, N-(4-methoxyphenyl)-p-menthanecarboxamide, N-ethyl-2,2-diisopropylbutanamide, N-cyclopropyl-p-menthanecarboxamide, N-(4-cyanomethylphenyl)-p-menthanecarboxamide, N-(2- pyridin-2-yl)-3-p-menthanecarboxamide, N-(2-hydroxyethyl)-2-isopropyl-2,3-dimethylbutanamide, N-(1,1-dimethyl-2-hydroxyethyl)-2,2-diethylbutanamide, cyclopropanecarboxylic acid (2-isopropyl-5-methylcyclohexyl)amide, N-ethyl-2,2-diisopropylbutanamide, N-[4-(2-amino-2-oxoethyl)phenyl]-p-menthanecarboxamide, 2-[(2-p-menthoxy)ethoxy]ethanol, 2,6-diethyl-5-isopropyl-2-methyltetrahydropyran, and trans-4-tert-butylcyclohexanol, and racemates and optically active forms of these;

sugar alcohols (β) such as xylitol, erythritol, dextrose, and sorbitol;

natural products (γ) such as Japanese mint oil, peppermint oil, spearmint oil, and *eucalyptus* oil; and compounds (δ) described in JP-A-2001-294546, JP-A-2005-343915, JP-A-2007-002005, JP-A-2009-263664, JP-A-2010-254621, JP-A-2010-254622, JP-A-2011-079953, U.S. Pat. Nos. 4,136,163, 4,150,052, 4,178,459, 4,190,643, 4,193,936, 4,226,988, 4,230,688, 4,032,661, 4,153,679, 4,296,255, 4,459,425, 5,009,893, 5,266,592, 5,698,181, 5,725,865, 5,843,466, 6,231,900 B1, 6,277,385 B1, 6,280,762 B1, 6,306,429 B1, 6,432,441 B1, 6,455,080 B1, 6,627,233 B1, 7,078,066 B2, 6,783,783 B2, 6,884,906 B2, 7,030,273 B1, 7,090,832 B2, US-A1-2004/0175489, US-A1-2004/0191402, US-A1-2005/0019445, US-A1-2005/0222256, US-A1-2005/0265930, US-A1-2006/015819, US-A1-2006/0249167, EP-A1-1689256, WO 2005/082154, WO 2005/099473, WO 2006/058600, WO 2006/092076, and WO 2006/125334.

These can be used as one kind or by appropriately blending two kinds or more of them. Above all, it is preferred to contain at least one cool feeling substance selected from the group consisting of the compounds (α), the sugar alcohols (β) and the natural products (γ).

The methyl menthol derivative of the present invention and the cool feeling substance which is not included therein can be used at an arbitrary ratio as long as the effect of the present invention is not impaired, however, a preferred use ratio of the methyl menthol derivative to the cool feeling substance which is not included therein is preferably in the range of 1:99 to 90:10 in terms of mass ratio.

The cooling agent composition of the present invention can be blended to a flavor composition and/or a fragrance composition or products such as beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs.

The cooling agent composition containing the methyl menthol derivative of the present invention has a strong and persistent cool feeling effect, and therefore, by including this cooling agent composition, a sensory stimulant composition having a cool feeling effect can be prepared. In the case where the sensory stimulant composition is prepared, the blending amount of the cooling agent composition requires to appropriately change its application range or application method in accordance with the type of product, intended use, etc., but in general, it is preferably used at a concentration of 0.00001 to 50 mass %, preferably 0.0001 to 20 mass %, and particularly preferably 0.001 to 4 mass % with respect to the total composition of the sensory stimulant composition. The sensory stimulant composition of the present invention is a composition which imparts an effect of stimulating the sensation. The effect of stimulating the sensation includes a cool feeling effect and/or a warm feeling effect, and therefore, in the present invention, the sensory stimulant composition is used as a concept also including a cooling agent composition and/or a warming agent composition.

In the cooling agent composition of the present invention, by using a warm feeling substance in combination, the stimulating effect of the sensory stimulant composition can be adjusted. Examples of the warm feeling stimulating component include:

compounds (ε) such as vanillyl methyl ether, vanillyl ethyl ether, vanillyl propyl ether, vanillyl isopropyl ether, vanillyl butyl ether, vanillyl amyl ether, vanillyl isoamyl ether, vanillyl hexyl ether, isovanillyl methyl ether, isovanillyl ethyl ether, isovanillyl propyl ether, isovanillyl isopropyl ether, isovanillyl butyl ether, isovanillyl amyl ether, isovanillyl isoamyl ether, isovanillyl hexyl ether, ethyl vanillyl methyl ether, ethyl vanillyl ethyl ether, ethyl vanillyl propyl ether, ethyl vanillyl isopropyl ether, ethyl vanillyl butyl ether, ethyl vanillyl amyl ether, ethyl vanillyl isoamyl ether, ethyl vanillyl hexyl ether, vanillin propylene glycol acetal, isovanillin propylene glycol acetal, ethyl vanillin propylene glycol acetal, vanillyl butyl ether acetic acid ester, isovanillyl butyl ether acetic acid ester, ethyl vanillyl butyl ether acetic acid ester, 4-(1-menthoxymethyl)-2-(3'-methoxy-4'-hydroxyphenyl)-1,3-dioxolane, 4-(1-menthoxymethyl)-2-(3'-hydroxy-4'-methoxyphenyl)-1,3-dioxolane, 4-(1-menthoxymethyl)-2-(3'-ethoxy-4'-hydroxyphenyl)-1,3-dioxolane, capsaicin, dihydrocapsaicin, nordihydrocapsaicin, homodihydrocapsaicin, homocapsaicin, biscapsanthin, trishomocapsanthin, nornorcapsanthin, norcapsanthin, capsaicinol, vanillyl caprylamide (octylic acid vanillylamide), vanillyl pelargonamide (nonylic acid vanillylamide), vanillyl caproamide (decylic acid vanillylamide), vanillyl undecamide (undecylic acid vanillylamide), N-trans-feruloyltyramine, N-5-(4-hydroxy-3-methoxyphenyl)-2E,4E-pentadienoylpiperidine, N-trans-feruloylpiperidine, N-5-(4-hydroxy-3-methoxyphenyl)-2E-pentenoylpiperidine, N-5-(4-hydroxyphenyl)-2E,4E-pentadienoylpiperidine, piperine, isopiperine, chavicine, isochavicine, piperamine, piperettine, piperolein B, retrofractamide A, pipercide, guineenside, piperiline, piperamide C5:1 (2E), piperamide C7:1 (6E), piperamide C7:2 (2E,6E), piperamide C9:1 (8E), piperamide C9:2 (2E,8E), piperamide C9:3 (2E,4E,8E), fagaramide, sanshool-I, sanshool-II, hydroxysanshool, sanshoamide, gingerol, shogaol, zingerone, methylgingerol, paradol, spilanthol, chavicine, polygodial (tadeonal), isopolygodial, dihydropolygodial, and tadeon, and racemates and optically active forms of these;

natural products (ζ) such as *capsicum* oil, *capsicum* oleoresin, ginger oleoresin, jambu oleoresin (*Spilanthes oleracea* extract), sansho (*Zanthoxylum piperitum*) extract, sanshoamide, black pepper extract, white pepper extract, and *polygonum* extract; and compounds (η) described in JP-A-8-225564, JP-A-2007-015953, JP-A-2007-510634, JP-A-2008-505868, WO 2007/013811, WO 2003/106404, EP-A2-1323356, DE-A1-10351422, US-A1-2005/0181022, and US-A1-2008/0038386.

These can be used as one kind or by appropriately blending two kinds or more of them. Above all, it is preferred to contain at least one warm feeling substance selected from the group consisting of the compounds (ε) and the natural products (ζ).

In the case where a cool feeling effect is aimed, the blending ratio of the warm feeling substance to the cool feeling substance may be any value as long as the warm feeling effect is not imparted by blending the warm feeling substance, and in general, the blending amount of the warm feeling substance is set to 0.001 to 0.95 times, preferably 0.01 to 0.5 times the total mass of the cooling agent composition. In the sensory stimulant composition including the cooling agent composition containing the methyl menthol derivative of the present invention, by adding the warm feeling substance to the cooling agent composition at the above-mentioned ratio, further improvement of the cool feeling effect is observed, and thus, the cool feeling effect is increased.

Further, in the case where a warm feeling effect is aimed, the blending ratio may be any value as long as the cool feeling effect is not imparted by mixing the cooling agent composition, and in general, the blending amount of the cooling agent composition is set to 0.001 to 0.95 times, preferably 0.01 to 0.5 times the total mass of the warm feeling substance.

Examples of the flavor component and/or the fragrance component which can be included along with the cooling agent composition or the sensory stimulant composition of the present invention include various synthetic flavors and/or fragrances, natural essential oils, synthetic essential oils, citrus fruit oils, and animal flavors and/or fragrances, and a wide variety of flavor components and/or fragrance components as described in, for example, NPL 1 can be used.

Among these, representative examples thereof include α-pinene, limonene, cis-3-hexenol, phenylethyl alcohol, styrallyl acetate, eugenol, rose oxide, linalool, benzaldehyde, muscone, MUSK T (Takasago International Corporation), and THESARON (Takasago International Corporation).

The contents of the cooling agent composition or the sensory stimulant composition in the flavor composition or the fragrance composition containing the cooling agent composition or the sensory stimulant composition of the present invention and the above-mentioned flavor component and/or fragrance component can be adjusted in accordance with the type of flavor and/or fragrance or another component to be mixed together, the intended use of the flavor composition and/or the fragrance composition, etc. For example, in the fragrance composition for fragrance or cosmetic, in general, the content of the cooling agent composition or the sensory stimulant composition is 0.00001 to 50 mass %, preferably 0.001 to 50 mass %, and particularly preferably 0.01 to 20 mass % with respect to the total mass of the fragrance composition.

Further, in the flavor composition for beverages or foods, in general, the content of the cooling agent composition or the sensory stimulant composition is preferably 0.0001 to 50 mass %, more preferably 0.001 to 30 mass % with respect to the total mass of the flavor composition.

In the cooling agent composition-containing flavor composition and/or fragrance composition containing the cooling agent composition or the sensory stimulant composition-containing flavor composition and/or fragrance composition containing the sensory stimulant composition may include one type or two or more types of other flavor retention agent and/or fragrance retention agent conventionally used in the flavor composition and/or the fragrance composition as needed. In such a case, examples of the other flavor retention agent and/or fragrance retention agent include ethylene glycol, propylene glycol, dipropylene glycol, glycerin, hexyl glycol, benzyl benzoate, triethyl citrate, diethyl phthalate, hercolyn, middle chain fatty acid triglyceride, and middle chain fatty acid diglyceride, and one type or two or more types among these can be included.

The cooling agent composition or the sensory stimulant composition of the present invention can be used for imparting cool feeling or sensory stimulation to various products as described above as the cooling agent composition or the sensory stimulant composition alone or by forming into the cooling agent composition-containing flavor composition and/or fragrance composition or the sensory stimulant composition-containing flavor composition and/or fragrance composition containing the cooling agent composition or the sensory stimulant composition.

The product to which cool feeling or sensory stimulation is imparted by the cooling agent composition or the sensory stimulant composition of the present invention by itself or by the cooling agent composition-containing flavor composition and/or fragrance composition or the sensory stimulant composition-containing flavor composition and/or fragrance composition is not particularly limited, however, examples thereof include beverages; foods; toiletry products such as cleaning agents, detergents for kitchen, and bleaching agents; air care products such as deodorants and air fresheners; compositions for oral use; fragrance or cosmetic such as fragrance products, basic cosmetics, finishing cosmetics, hair cosmetics, sunburn cosmetics, and medicinal cosmetics; hair care products; skin care products such as soaps; body care products such as body washers; bathing agents; cleaning agents for clothes; soft finishing agents for clothes; aerosol agents; daily necessities and household goods; and quasi-drugs and drugs.

Various forms can be exemplified as follows:

examples of the beverages include beverages such as fruit juice beverages, fruit wines, milk-based beverages, carbonated beverages, refreshing beverages, and health drinks; tea beverages or favorite beverages such as green tea, oolong tea, black tea, persimmon leaf tea, chamomile tea, low striped bamboo tea, mulberry tea, dokudami tea, pu-erh tea, mate tea, rooibos tea, gymnema tea, guava tea, coffee, and cocoa; soups such as Japanese style soups, Western style soups, and Chinese soups; and various instant beverages;

examples of the foods include frozen sweets such as ice creams, sherbets, and ice candies; desserts such as jelly and puddings; Western style confections such as cakes, cookies, chocolates, and chewing gums; Japanese style confections such as steamed bean-jam buns, sweet bean jelly, and sweet rice jelly; jams; candies; breads; flavor seasonings; various instant foods; and various snack foods;

examples of the compositions for oral use include toothpastes, oral cleaning agents, mouthwashes, troches, and chewing gums;

examples of the fragrance products include perfumes, eau de perfumes, eau de toilettes, and eau de colognes;

examples of the basic cosmetics include facial wash creams, vanishing creams, cleansing creams, cold creams, massage creams, milky lotions, skin lotions, beauty lotions, facial packs, and makeup removers;

examples of the finishing cosmetics include foundations, face powders, solid face powders, talcum powders, lipsticks, lip balms, cheek rouges, eye liners, mascaras, eye shadows, eyebrow pencils, eye packs, nail enamels, and enamel removers;

examples of the hair cosmetics include pomade, brilliantine, hair set lotions, hair sticks, hair solids, hair oils, hair treatments, hair creams, hair tonics, hair liquids, hair sprays, bandolines, revitalizing hair tonics, and hair dyes;

examples of the sunburn cosmetics include suntan products and sunscreen products;

examples of the medicinal cosmetics include antiperspirants, after shaving lotions and gels, permanent wave agents, medicinal soaps, medicinal shampoos, and medicinal skin cosmetics;

examples of the hair care products include shampoos, rinses, rinse-in-shampoos, conditioners, treatments, and hair packs;

examples of the soaps include toilet soaps, bath soaps, perfume soaps, transparent soaps, and synthetic soaps;

examples of the body washers include body soaps, body shampoos, hand soaps, and face creams;

examples of the bathing agents include bath additives (such as bath salts, bath tablets, and bath liquids), bath foams (such as bubble baths), bath oils (such as bath perfumes and bath capsules), milk baths, bath jelly, and bath cubes:

examples of the detergents include heavy-duty detergents for clothes, light-duty detergents for clothes, liquid detergents, laundry soaps, compact detergents, and powder soaps;

examples of the soft finishing agents include softeners and furniture cares;

examples of the cleaning agents include cleansers, house cleaners, toilet cleaning agents, bathroom cleaning agents, glass cleaners, mold removers, and drain cleaning agents:

examples of the detergents for kitchen include kitchen soaps, kitchen synthetic soaps, and dish detergents;

examples of the bleaching agents include oxidation type bleaching agents (such as chlorine-based bleaching agents and oxygen-based bleaching agents), reductive bleaching agents (such as sulfur-based bleaching agents), and optical bleaching agents;

examples of the aerosol agents include spray type ones and powder sprays;

examples of the deodorants and air fresheners include solid type, gel type, and liquid type (aqueous and oily) ones;

examples of the daily necessities and household goods include tissue papers and toilet papers;

examples of the quasi-drugs include liquid bath additives, mouthwashes, and repellents, and examples of the repellents include mist spray type and aqueous liquid type ones; and examples of the drugs include medicinal cosmetics and medicinal lotions.

As the dosage form of the methyl menthol derivative of the present invention, the form of a mixture itself can be adopted. As another dosage form, an arbitrary form, for example, a liquid form in which dissolution is performed in an alcohol, a polyhydric alcohol such as propylene glycol, glycerin or dipropylene glycol, or an ester such as triethyl citrate, benzyl benzoate or diethyl phthalate;

a natural gum substance such as gum Arabic or gum tragacanth;

an emulsified form in which emulsification is performed with an emulsifier such as a glycerol fatty acid ester or a sucrose fatty acid ester;

a powder form in which coating with a film is performed by using a natural gum substance such as gum Arabic or an excipient such as gelatin or dextrin;

a solubilized form or a dispersed form in which solubilization or dispersion is performed by using a surfactant, for example, a nonionic surfactant, an anionic surfactant, a cationic surfactant, an amphoteric surfactant, or the like; or a microcapsule obtained by a treatment with an encapsulating agent, or the like; is selected and used in accordance with the intended use.

As a method for imparting cool feeling or sensory stimulation to various products as described above with the cooling agent composition or the sensory stimulant composition of the present invention, or the cooling agent composition-containing flavor composition and/or fragrance composition or the sensory stimulant composition-containing flavor composition and/or fragrance composition containing the same, for example, in accordance with the type of the product to which cool feeling or sensory stimulation is imparted or the final form of the product (for example, the form of the product such as a liquid form, a solid form, a powder form, a gel form, a mist form, or an aerosol form), the cooling agent composition or the sensory stimulant composition, or the cooling agent composition-containing flavor composition and/or fragrance composition or the sensory stimulant composition-containing flavor composition and/or fragrance composition containing the same may be added or applied directly to the product;

the cooling agent composition or the sensory stimulant composition, or the cooling agent composition-containing flavor composition and/or fragrance composition or the sensory stimulant composition-containing flavor composition and/or fragrance composition containing the same may be dissolved in, for example, an alcohol or a polyhydric alcohol such as propylene glycol or glycerin to be turned into a liquid form and added or applied;

it may be turned into a solubilized form or a dispersed form by being solubilized or emulsification-dispersed by using a natural gum substance such as gum Arabic or gum tragacanth or a surfactant (for example, a nonionic surfactant such as a glycerol fatty acid ester or a sucrose fatty acid ester, an anionic surfactant, a cationic surfactant, an amphoteric surfactant, or the like) and added or applied;

it may be turned into a powder form with a coating film formed by using a natural gum substance such as gum Arabic or an excipient such as gelatin or dextrin and added or applied; or it may be formed into a microcapsule by a treatment with an encapsulating agent and added or applied.

Further, the cooling agent composition or the sensory stimulant composition, or the cooling agent composition-containing flavor composition and/or fragrance composition or the sensory stimulant composition-containing flavor composition and/or fragrance composition containing the same may be included in an inclusion agent such as cyclodextrin so as to stabilize the composition and also make it sustained-releasable, and used.

The addition amount or application amount of the cooling agent composition or the sensory stimulant composition to the product when cool feeling or sensory stimulation is imparted can be adjusted in accordance with the type or form of the product, an effect or action of imparting cool feeling or sensory stimulation required for the product, or the like. In general, the addition amount or application amount of the cooling agent composition or the sensory stimulant composition is preferably about $1\times10^{-7}$ to 0.1 mass % or so, more preferably $1\times10^{-6}$ to 0.01 mass % with respect to the mass of the product.

EXAMPLES

Hereinafter, the measurement of products in Synthesis Examples and Examples was performed by using the following apparatuses and devices.

NMR spectrum: $^1$H-NMR: AM-500 (500 MHz) (manufactured by Bruker Co., Ltd.)

External standard substance: tetramethylsilane

Gas chromatograph (GC): GC-2010AF (manufactured by Shimadzu Corporation)

Column: DB-WAX (30 m×0.32 nm×0.5 μm) (manufactured by Hewlett Packard Co.), IC-1 (30 m×0.25 mm×0.25 μm), (manufactured by Hewlett Packard Co.), Rtx-1 (30 m×0.25 mm×0.25 μm) (manufactured by Restek, Inc.)

Chiral column (optical purity measurement): Beta DEX™ 225 (30 m×0.25 mm×0.25 μm), Beta DEX™ 325 (30 m×0.25 mm×0.25 μm) (manufactured by Supelco, Inc.)

High-resolution mass spectrum (HRMS): JMS-T100GCV (manufactured by JEOL Ltd.), LCMS-IT-TOF (manufactured by Shimadzu Corporation)

Optical rotation: JASCO P-1020 (manufactured by JASCO Corporation)

Melting point: melting point measurement device (serial No.: 2678) (manufactured by Yanagimoto Seisakusyo Co., Ltd.)

[Synthesis Example 1] Synthesis of 3-methylcitronellal (3,3,7-trimethyl-6-octenal) (Exemplary Compound 3)

[Chem. 38]

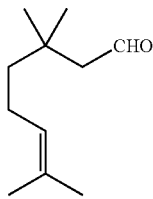

This reaction was performed under a nitrogen atmosphere. A 2-L four-necked flask equipped with a dropping funnel was prepared, and copper iodide (100 g, 1.05 eq.) and diethyl ether (200 mL) were added to the flask, and the inside of the system was cooled to 0 to 5° C. while stirring. A methyllithium-ether solution (1.08 mol/L, 992 mL, 2.05 eq. vs. CuI) was added to the dropping funnel, and then dropped slowly over 2 hours. After completion of the dropping, stirring was performed for 30 minutes while maintaining the temperature, and then, the inside of the system was cooled to −60° C. or lower. Citral (76.1 g, 500 mmol) and diethyl ether (50 mL) were added to the dropping funnel, and then dropped slowly over 20 minutes. After completion, stirring was performed for 1 hour while maintaining the temperature, and the temperature in the system was gradually increased to 0 to 5° C. After 1 hour, completion of the reaction was confirmed by GC, and as a posttreatment, a saturated aqueous ammonium chloride solution was dropped slowly while cooling. The mixed solution was filtered through celite, and the oil layer was washed three times with a saturated aqueous ammonium chloride solution and once with a saturated saline solution, and dried over anhydrous magnesium sulfate, followed by concentration under reduced pressure (78.4 g). This reaction was performed three times in total, and the obtained oil was subjected to simple distillation using a Claisen distillation apparatus (0.1 mmHg, overhead: 60 to 65° C., bath temperature: 85 to 95° C.), whereby an objective substance (180 g, yield: 72%) was obtained.

$^1$H-NMR (500 MHz, CDCl$_3$): δ (s, 3H), 1.33-1.39 (m, 2H), 1.60 (s, 3H), 1.68 (d, 3H, J=0.85 Hz), 1.94-2.01 (m, 2H), 2.27 (d, 2H, J=3.2 Hz), 5.06-5.11 (m, 1H), 9.85 (t, J=3.1 Hz)

[Synthesis Example 2] Synthesis of 5-methylisopulegol (5,5-dimethyl-2-(prop-1-en-2-yl)cyclohexanol) (Exemplary Compound rac-4)

[Chem. 39]

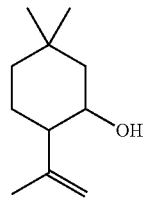

To a 200-mL four-necked flask equipped with a condenser were added active silica-alumina (771 mg, 2 mass %), 3-methylcitronellal (3) (25.8 g, 153 mmol) and toluene (77 mL). A reaction was performed by stirring at 80° C., and after 2 hours, the reaction was completed (conv.>99%). After the catalyst was filtered off, simple distillation was performed using a Claisen distillation apparatus (<0.1 Pa, overhead: 55 to 56° C., bath temperature: 88° C.), whereby a colorless oil (24.6 g, yield: 66%) which is an objective substance was obtained. A cis/trans ratio was 13/87.

HRMS: mass: 168.1514, actual measurement value: 168.1535

$^1$H-NMR (500 MHz, CDCl$_3$): δ0.90-0.95 (m, 3H), 0.96 (s, 3H), 1.09-1.16 (m, 1H), 1.18-1.27 (m, 1H), 1.26-1.41 (m, 2H), 1.44-1.58 (m, 2H), 1.74 (br, 3H), 1.75-1.88 (m, 2H), 3.62-3.66 (m, 1H), 4.85-4.86 (m, 1H), 4.83-4.98 (m, 1H) (trans/cis mix)

[Synthesis Example 3] Synthesis of trans-5-methyl menthol (trans-2-isopropyl-5,5-dimethylcyclohexanol) (rac-trans-5)

[Chem. 40]

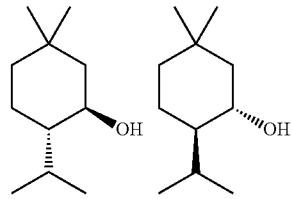

5-Methylisopulegol (rac-4) (10.0 g, 59.4 mmol) obtained in Synthesis Example 2, and palladium on carbon (N.E.

Chemcat. Wet, STD 5%, 100 mg, 1 mass %) and methanol (20 mL) were added. A reaction was performed for 15 hours at 50° C. under a hydrogen pressure of 1 MPa to 2 MPa. Completion of the reaction was confirmed by GC, and a post-treatment was performed. The catalyst was filtered off through celite, followed by concentration, whereby trans-5-methyl menthol (9.80 g, yield: 97%) was obtained as a white solid.

Melting point: 60 to 64° C.
HRMS: mass: 170.1671, actual measurement value: 170.1680
$^1$H-NMR (500 MHz, CDCl$_3$): δ0.84 (d, 3H, J=7.0 Hz), 0.89 (s, 3H, >C—CH$_3$), 0.93-0.95 (m, 6H), 1.04-1.21 (m, 5H), 1.37 (dt, 1H, J=9.6, 2.6 Hz), 1.46-1.50 (m, 1H), 1.68-1.73 (m, 1H), 2.12-2.21 (m, 1H), 3.53-3.62 (m, 1H)

[Synthesis Example 4] Synthesis of (+)-5-methylmenthone ((+)-2-isopropyl-5,5-dimethylcyclohexanone) (Exemplary Compound (+)-7)

[Chem. 41]

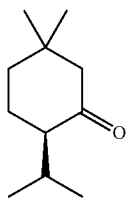

Under a nitrogen atmosphere, a 1-L four-necked flask equipped with two dropping funnels was prepared, and a methyl magnesium bromide-tetrahydrofuran (THF) solution (0.92 mol/L, 500 mL, 460 mmol, 1.25 eq.) was added to the flask, and the inside of the system was cooled to −10° C. while stirring. A THF suspension (25 mL) of copper iodide (13.4 g, 20 mol %) was prepared in the dropping funnel and added slowly to the inside of the system. After completion of the addition, aging was performed for 30 minutes, and a THF solution (50 mL) of (−)-piperitone (53.9 g, 354 mmol) was added to the dropping funnel, and then dropped slowly over 1.5 hours while maintaining the temperature in the system at −5° C. or lower. Complete consumption of (−)-piperitone was confirmed in 1 hour after completion of the dropping, and a post-treatment was performed. While maintaining the temperature in the system at −10° C., a saturated aqueous ammonium chloride solution (200 mL) was added slowly to the inside of the system with stirring. After completion of the addition, stirring was performed for 30 minutes and the temperature was gradually increased to room temperature. The reaction solution was transferred to a separating funnel, and toluene was added thereto, followed by washing three times with a saturated aqueous ammonium chloride solution. After the oil layer was concentrated by filtration, Claisen distillation was performed (bath temperature: 100° C., overhead: 56° C., 0.1 Pa), whereby objective (+)-5-methylmenthone was obtained as a yellowish oil (54.2 g, yield: 88%, 85% ee.).

$[α]^D_{20}$=+25.4 (c=0.2, EtOH)
HRMS: mass: 168.1514, actual measurement value: 168.1512
$^1$H-NMR (500 MHz, CDCl$_3$): δ0.88 (d, 3H, J=1.5 Hz), 0.90 (br, 9H), 1.01 (s, 3H), 1.52-1.67 (m, 4H), 1.89-2.02 (m, 2H), 2.07-2.16 (m, 2H)

[Synthesis Example 5] Synthesis of 5-methylmenthone (2-isopropyl-5,5-dimethylcyclohexanone) (Exemplary Compound rac-7)

[Chem. 42]

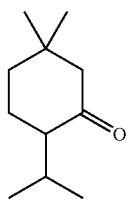

(+)-5-Methylmenthone ((+)-7) (10.0 g) obtained in Synthesis Example 4 was heated and stirred at 90° C. for 3 hours, whereby objective 5-methylmenthone was obtained quantitatively as a colorless oil.

HRMS: mass: 168.1514, actual measurement value: 168.1521
$^1$H-NMR (500 MHz, CDCl$_3$): δ0.88 (d, 3H, J=1.6 Hz), 0.90 (br, 9H), 1.01 (s, 3H), 1.52-1.67 (m, 4H), 1.89-2.02 (m, 2H), 2.07-2.15 (m, 2H)

[Example 1] Synthesis of 5-methylmenthylamide (2-isopropyl-5,5-dimethylcyclohexanecarboxamide) (Exemplary Compound 14a-50)

[Chem. 43]

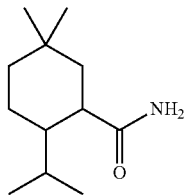

This reaction was performed under a nitrogen atmosphere. Potassium t-butoxide (396 mg, 1.2 eq.) and THF (5 ml) were added to a flask, and p-toluenesulfonylmethyl isocyanide (590 mg, 1.1 eq.) and THF (10 ml) were added to a dropping funnel, and the solution in the funnel was dropped while cooling and stirring at 0 to 5° C. After 2 hours, temperature of the inside of the system was cooled to −10° C., and a THF solution (5 ml) of 5-methylmenthone (rac-7) (500 mg, 2.94 mmol) obtained in Synthesis Example 5 was dropped while stirring. After completion of the dropping, the temperature was gradually increased, and a reaction was performed for 8 hours at an internal temperature of 45° C. As a post-treatment, cooling was performed to room temperature, followed by concentration under reduced pressure to distill off THF. To the resulting residue, toluene and tap water were added, and the oil layer was washed twice with tap water and once with a saturated saline solution. Drying was performed with anhydrous magnesium sulfate, and then filtration and concentration under reduced pressure were performed. Thereafter, to a four-necked flask equipped with a condenser were added the obtained oil, potassium hydroxide (500 mg, 3.2 eq.), tap water, and t-butanol (6 ml), followed by refluxing and stirring for 9 hours. As a post-treatment, extraction was performed with toluene and tap water, and the oil layer was washed and dried by a conventional method, and a residue obtained by concentration was isolated and purified by column chromatography (ethyl acetate), followed by further recrystallization by using heptane/ethyl acetate, whereby objective 5-methylmenthyl amide was obtained as a white solid (121 mg, yield: 25%).

Melting point: 141 to 145° C.

HRMS: mass: 198.1852, actual measurement value: 198.1841 ([M+H]$^+$)

$^1$H-NMR (500 MHz, CDCl$_3$): δ0.83 (d, 1H, J=6.9 Hz), 0.87-0.94 (m, 9H), 1.12-1.28 (m, 2H), 1.40-1.55 (m, 5H), 1.80 (quid, 1H, J=13.9, 2.5 Hz), 2.23 (td, 1H, J=11.9, 3.7 Hz), 5.53-5.56 (br, 2H)

[Synthesis Example 6] Synthesis of 5-methylmenthyl chloride (3-chloro-4-isopropyl-1,1-dimethylcyclohexane)

[Chem. 44]

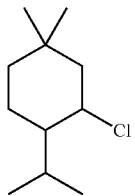

To a 200-mL flask were added trans-5-methyl menthol (rac-trans-5) (11.0 g, 64.6 mmol) obtained in Synthesis Example 3, toluene (5.5 mL), zinc chloride (28.2 g, 3.2 eq.), and concentrated hydrochloric acid (16.2 mL), and a reaction was performed at room temperature for 6 hours. Completion of the reaction was confirmed by GC-MS, and a post-treatment was performed. The aqueous layer was removed by using a separating funnel, and the oil layer was washed five times with tap water. Drying was performed with anhydrous magnesium sulfate, followed by concentration by filtration. The resulting residue was isolated and purified by silica gel column chromatography (heptane), whereby an isomer mixture of 5-methylmenthyl chloride (10.4 g, yield: 70%) was obtained as a light yellow oil.

HRMS: mass: 233.1312, actual measurement value: 233.1314 ([M+Cl]$^-$)

$^1$H-NMR (500 MHz, CDCl$_3$): δ0.81 (d, 3H, J=7.0 Hz), 0.90 (s, 3H), 0.92 (d, 3H, J=7.0 Hz), 0.94 (s, 3H), 0.97-1.12 (m, 1H), 1.19-1.38 (m, 2H), 1.41 (dt, 1H, J=9.5, 1.5 Hz), 1.52-1.60 (m, 2H), 1.94-2.00 (m, 1H), 2.34 (quid, 1H, J=7.0, 1.5 Hz), 3.95 (td, 1H. J=12.0, 1.6 Hz)

[Example 2] Synthesis of 5-methylmenthyl carboxylic acid methyl ester (methyl 2-isopropyl-5,5-dimethylcyclohexane carboxylate) (Exemplary Compound 15a-6)

[Chem. 45]

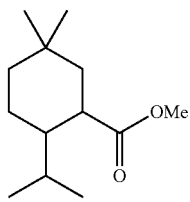

Under a nitrogen atmosphere, magnesium (1.51 g, 1.30 eq.) was added to a 200-mL four-necked flask equipped with a condenser and a dropping funnel, and 5-methylmenthyl chloride (9.00 g, 47.7 mmol) obtained in Synthesis Example 6 and THF (40 mL) were added to the dropping funnel. The flask internal temperature was heated to 45° C., and the solution in the funnel was dropped over 1 hour while stirring. Dimethyl carbonate (8.03 mL, 2.00 eq.) and THF (5 mL) were added to the funnel, and then dropped over about 40 minutes. After completion, the temperature in the system was increased to 55° C., and followed by heating and stirring for 8 hours in total. As a post-treatment, the inside of the system was cooled, and the reaction was completed with an aqueous ammonium chloride solution, and a crude product obtained by a conventional method was isolated and purified by silica gel column chromatography (heptane/ethyl acetate=6/1), whereby an objective substance was obtained as a colorless oil (9.13 g, 43.0 mmol, yield: 90%).

HRMS: mass: 213.1837, actual measurement value: 213.1849 ([M+H]$^+$)

$^1$H-NMR (500 MHz, CDCl$_3$): δ0.81 (d, 3H, J=7.0 Hz), 0.88 (s, 3H), 0.90 (d, 3H, J=6.9 Hz), 0.92 (s, 3H), 1.14-1.35 (m, 4H), 1.36-1.68 (m, 4H), 2.42-2.50 (m, 1H), 3.65 (s, 3H)

[Synthesis Example 7] Synthesis of 5-methylmenthyl carboxylic acid (2-isopropyl-5,5-dimethylcyclohexane carboxylic acid) (Exemplary Compound rac-11a)

[Chem. 46]

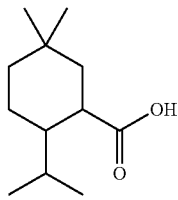

To a 200-mL flask equipped with a condenser were added 5-methylmenthyl carboxylic acid methyl ester (15a-6) (8.16 g, 38.4 mmol) obtained in Example 2, ethanol (10 mL), and a 25 mass % aqueous sodium hydroxide solution (23 mL), followed by heating and stirring at 95° C. for 6 hours. The solution was cooled to room temperature and then concentrated under reduced pressure, and toluene and tap water were added thereto, followed by transferring to a separating funnel. The oil layer was removed, and the aqueous layer was made acidic as for the liquid property thereof with dilute hydrochloric acid, and extraction was performed with chloroform. The oil layer was dried with anhydrous magnesium sulfate, and then purified by silica gel column chromatography, whereby an objective white solid was obtained (5.07 g, yield: 65.6%).

Melting point: 91 to 94° C.

HRMS: mass: 198.1620, actual measurement value: 198.1619

$^1$H-NMR (500 MHz, CDCl$_3$): δ0.84 (d, 3H, J=7.0 Hz), 0.89 (s, 3H), 0.91 (d, 3H, J=14.0 Hz), 0.93 (s, 3H), 1.15-1.26 (m, 2H), 1.38-1.51 (m, 4H), 1.61 (dt, 2H, J=13.0, 3.0 Hz), 1.70-1.78 (m, 1H), 2.42-2.50 (m, 1H), 8.0-13.0 (br, 1H)

[Synthesis Example 8] Synthesis of 5-methylmenthyl carboxylic acid (2-isopropyl-5,5-dimethylcyclohexane carboxylic acid) (Exemplary Compound rac-11a)

[Chem. 47]

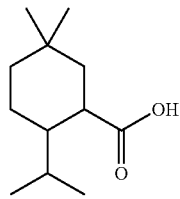

5-Methylmenthyl amide (15a-60) obtained in Example 1 was refluxed and stirred using a 25 mass % aqueous sodium hydroxide solution and ethylene glycol, and hydrolyzed in the same manner, whereby the same compound was obtained (yield: 32%).

[Synthesis Example 9] Synthesis of 5-methylmenthyl carboxylic acid (2-isopropyl-5,5-dimethylcyclohexane carboxylic acid) (Exemplary Compound rac-11a)

[Chem. 48]

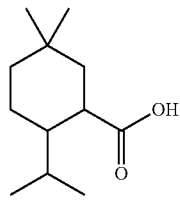

Under a nitrogen atmosphere, magnesium (2.68 mg, 1.30 eq.) was added to a 200-mL four-necked flask equipped with a condenser and a dropping funnel, and 5-methylmenthyl chloride (16.0 g, 84.8 mmol) obtained in Synthesis Example 6 and THF (80 mL) were added to the dropping funnel. The flask internal temperature was heated to 45° C., and the solution in the funnel was dropped over 2 hours while stirring. Thereafter, the system was heated and stirred for 9 hours in total while blowing carbon dioxide gas thereinto. As a post-treatment, after the solvent was collected, the inside of the system was cooled, and toluene and tap water were added thereto. Dilute hydrochloric acid was added to the aqueous layer, followed by extraction with chloroform, and the oil layer was dried with anhydrous magnesium sulfate and then concentrated under reduced pressure, whereby an objective white crystal was obtained (5.76 g, yield: 34%).

[Synthesis Example 10] Synthesis of optically active (−)-trans-5-methylisopulegol ((1R,2S)-trans-5,5-dimethyl-2-(prop-1-en-2-yl)cyclohexanol) (Exemplary Compound (1R,2S)-trans-4)

[Chem. 49]

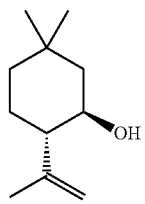

This reaction was performed under a nitrogen atmosphere. To a 200-mL flask equipped with a condenser were added (R)-1,1'-bi-2-naphthol ((R)-BINOL) (1.22 mg, 1.6 eq. vs. Al) and toluene (27 mL), followed by slowly adding triethylaluminium-toluene solution (2.7 mL, 5 mol %) thereto while stirring. After stirring was performed at room temperature for 1 hour, the inside of the system was cooled to 0 to 5° C., and 3-methylcitronellal (9.00 g, 53.5 mmol) obtained in Synthesis Example 1 was dropped slowly. After 3 hours, completion of the reaction was confirmed by GC, and as a post-treatment, quenching with toluene/hydrochloric acid was performed, and then, the oil layer was washed once with each of tap water and a saturated saline solution. Drying was performed with anhydrous magnesium sulfate, followed by passing through a silica gel column chromatograph and concentration under reduced pressure, whereby objective optically active (−)-trans-5-methylisopulegol was obtained as a colorless oil (7.42 g, yield: 83%, 80% ee.).

$[\alpha]^D{}_{25}$=−6.6 (c=0.6, CHCl$_3$)

HRMS: mass: 168.1519, actual measurement value: 168.1514

$^1$H-NMR (500 MHz, CDCl$_3$): δ0.94 (s, 3H, CH$_3$), 0.96 (s, 3H, CH$_3$), 1.14 (t, 1H, J=11.7 Hz), 1.22 (td, 1H, J=13.0, 4.6 Hz), 1.26-1.41 (m, 2H), 1.45-1.57 (m, 2H), 1.74 (dd, 3H, J=1.5, 0.9 Hz), 1.75-1.87 (m, 2H), 3.61-3.66 (m, 1H), 4.85-4.86 (m, 1H), 4.89-4.91 (m, 1H)

[Synthesis Example 11] Synthesis of optically active trans-5-methylisopulegol ((1S,2R)-trans-5,5-dimethyl-2-(prop-1-en-2-yl)cyclohexanol) ((1S,2R)-trans-4)

[Chem. 50]

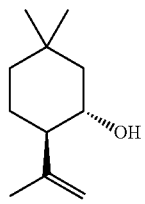

By using the method of Synthesis Example 5, (+)-trans-5-methylisopulegol was obtained as a colorless oil (3.90 g, yield: 78%, 78% ee.) from 3-methylcitronellal (5.00 g, 29.7 mmol) using (S)-BINOL as a ligand.

$[\alpha]^D_{25}$=+5.8 (c=0.3, CHCl$_3$).

$^1$H-NMR (500 MHz, CDCl$_3$): δ0.93 (s, 3H, CH$_3$), 0.96 (s, 3H, CH$_3$), 1.14 (t, 1H, J=11.7 Hz), 1.22 (td, 1H, J=13.2, 4.7 Hz), 1.25-1.42 (m, 2H), 1.45-1.59 (m, 2H), 1.74 (br, 3H), 1.76-1.88 (m, 2H), 3.64 (td, 1H, J=10.7, 4.4 Hz), 4.85-4.87 (m, 1H), 4.89-4.92 (m, 1H)

[Synthesis Example 12] Synthesis of optically active (−)-trans-5-methyl menthol ((1R,2S)-trans-2-isopropyl-5,5-dimethylcyclohexanol) (Exemplary Compound (1R,2S)-trans-5)

[Chem. 51]

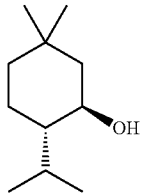

To a 100-mL autoclave were added (−)-trans-5-methylisopulegol ((1R,2S)-trans-4) (9.00 g, 54.0 mmol) obtained in Synthesis Example 10, and palladium on carbon (N.E. Chemcat. Wet, STD 5%, 90 mg, 1 mass %), and methanol (9 mL). The hydrogen pressure was charged to 1 MPa, and a reaction was performed at 50° C. for 26 hours. Completion of the reaction was confirmed by GC, and the catalyst was filtered through celite, followed by concentration and recrystallization by using methanol/heptane, whereby (−)-trans-5-methyl menthol was obtained as a white solid (7.80 g, yield: 86%, 80% ee.).

Melting point: 79 to 82° C.

$[\alpha]^D_{20}$=−36.7 (c=0.1, CHCl$_3$)

HRMS: mass: 170.1671, actual measurement value: 170.1671

$^1$H-NMR (500 MHz, CDCl$_3$): δ0.84 (d, 3H, J=7.0 Hz), 0.89 (s, 3H), 0.93-0.95 (m, 6H), 1.04-1.21 (m, 5H), 1.37 (dt, 1H, J=9.6, 2.6 Hz), 1.46-1.50 (m, 1H), 1.68-1.73 (m, 1H), 2.12-2.21 (m, 1H), 3.57 (sep, 1H, J=4.7 Hz)

[Synthesis Example 13] Synthesis of optically active (+)-trans-5-methyl menthol ((1S,2R)-trans-2-isopropyl-5,5-dimethylcyclohexanol) (Exemplary Compound (1S,2R)-trans-5)

[Chem. 52]

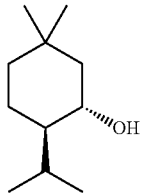

By using the method of Synthesis Example 12, (+)-5-methyl menthol was obtained as a white solid (0.91 g, yield: 90%, 78% ee.) from (+)-trans-5-methylisopulegol ((1S,2R)-trans-4) (1.00 g, 5.94 mmol) obtained in Synthesis Example 11.

Melting point: 78 to 81° C.

$[\alpha]^D_{20}$=+37.0 (c=0.1, CHCl$_3$)

$^1$H-NMR (500 MHz, CDCl$_3$): δ0.84 (d, 3H, J=7.0 Hz), 0.89 (s, 3H), 0.93-0.96 (m, 6H), 1.04-1.20 (m, 5H), 1.37 (dt, 1H, J=9.6, 2.5 Hz), 1.46-1.51 (m, 1H), 1.70 (dq, 1H, J=12.3, 2.5 Hz), 2.12-2.23 (m, 1H), 3.58 (sep, 1H, J=4.7 Hz)

[Synthesis Example 14] Synthesis of (+)-(1R,2S)-5-methylmenthyl chloride ((+)-(1R,2S)-3-chloro-4-isopropyl-1,1-dimethylcyclohexane)

[Chem. 53]

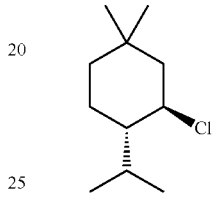

To a 100-mL flask equipped with a dropping funnel and a condenser were added (−)-5-methyl menthol ((1R,2S)-trans-5) (9.09 g, 53.4 mmol) obtained in Synthesis Example 12, toluene (4.5 mL), zinc chloride (23.28 g, 3.2 eq.), and concentrated hydrochloric acid (13.3 mL, 3.0 eq.), followed by reaction at room temperature for 8 hours. Completion of the reaction was confirmed by GC, and a post-treatment was performed. The aqueous layer was removed by using a separating funnel, and the oil layer was washed three times with tap water, and further washed with a 1 mass % aqueous NaOH solution and with a saturated saline solution. Drying was performed with anhydrous magnesium sulfate and concentration by filtration was performed, and the resulting residue was isolated and purified by silica gel column chromatography (heptane). The obtained optically active-5-methylmenthyl chloride was in the form of a colorless oil (4.89 g, yield: 57.2%, 80% ee.).

$[\alpha]^D_{20}$=+27.5 (c=0.3, EtOH)

HRMS: mass: 233.1312, actual measurement value: 233.1301 ([M+Cl]$^−$)

$^1$H-NMR (500 MHz, CDCl$_3$): δ0.80 (d, 3H, J=7.0 Hz), 0.90 (s, 3H), 0.92 (d, 3H, J=7.0 Hz), 0.94 (s, 3H), 0.97-1.12 (m, 1H), 1.19-1.38 (m, 2H), 1.41 (dt, 1H, J=9.5, 1.5 Hz), 1.52-1.60 (m, 2H), 1.94-1.99 (m, 1H), 2.29-2.40 (m, 1H), 3.95 (td, 1H, J=12.0, 1.6 Hz)

[Synthesis Example 15] Synthesis of (−)-5-methylmenthyl carboxylic acid ((−)-2-isopropyl-5,5-dimethylcyclohexane carboxylic acid) (Exemplary Compound (1R,2S)-11a)

[Chem. 54]

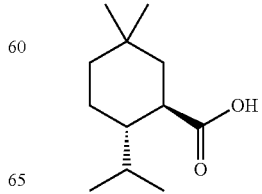

Under a nitrogen atmosphere, magnesium (718 mg, 1.30 eq.) was added to a 200-mL four-necked flask equipped with a condenser and a dropping funnel, and (−)-5-methylmenthyl chloride (4.29 g, 22.7 mmol) obtained in Synthesis Example 14 and THF (22 mL) were added to the dropping funnel. The flask internal temperature was heated to 45° C., and the solution in the funnel was dropped over 2 hours while stirring. Then, heating and stirring for 9 hours in total while blowing carbon dioxide gas into the system. As a post-treatment, after the solvent was collected, the inside of the system was cooled, and toluene and tap water were added thereto. Dilute hydrochloric acid was added to the aqueous layer, followed by extraction with chloroform, and the oil layer was dried with anhydrous magnesium sulfate and concentrated under reduced pressure, and then, purified by column chromatography (chloroform/ethyl acetate), whereby an objective white solid was obtained (1.17 g, yield: 26%, 80% ee.).

Melting point: 73 to 76° C.

$[\alpha]^D_{20}$=−30.0 (c=0.1, EtOH)

HRMS: mass: 198.1620, actual measurement value: 198.1608

$^1$H-NMR (500 MHz, CDCl$_3$): δ0.84 (d, 3H, J=7.0 Hz), 0.89 (s, 3H), 0.91 (d, 3H, J=13.8 Hz), 0.93 (s, 3H), 1.15-1.26 (m, 2H), 1.38-1.51 (m, 4H), 1.61 (dt, 2H, J=13.0, 3.0 Hz), 1.70-1.78 (m, 1H), 2.42-2.50 (n, 1H), 7.5-13.0 (br, 1H)

[Synthesis Example 16] Synthesis of (−)-cis-5-methyl menthol ((−)-cis-2-isopropyl-5,5-dimethylcyclohexanol) (Exemplary Compound (1R,2R)-5)

[Chem. 55]

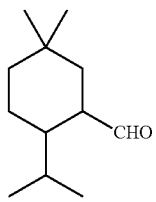

To a 200-mL four-necked flask was added (+)-5-methylmenthone ((+)-7) (19.7 g, 117 mmol) obtained in Synthesis Example 4 and methanol (80 mL), followed by cooling to 10° C. or lower while stirring. Sodium borohydride (5.32 g, 1.2 eq.) was slowly added thereto, followed by aging as such for 1 hour. Completion of the reaction was confirmed, and as a post-treatment, 1 N hydrochloric acid was slowly added thereto. Then, extraction was performed with toluene and heptane, and the oil layer was dried with anhydrous magnesium sulfate, and then concentrated by filtration. Purification was performed by Claisen distillation (bath temperature: 100° C., overhead: 58 to 67° C., 0.1 to 0.2 Pa), whereby an objective colorless oil was obtained (19.7 g, yield: 99%).

$[\alpha]^D_{20}$=−9.6 (c=0.2, EtOH)

HRMS: mass: 170.1664, actual measurement value: 170.1671

$^1$H-NMR (500 MHz, CDCl$_3$): δ0.83-0.90 (m, 4H), 0.95 (t, 6H, J=6.2 Hz), 1.06-1.08 (m, 4H), 1.13-1.21 (m, 1H), 1.33 (dd, 1H, J=14.5, 3.3 Hz), 1.40-1.60 (m, 4H), 1.64 (tt, 1H, J=14.4, 2.9 Hz), 4.11 (qui, 1H, J=3.2 Hz)

[Synthesis Example 17] Synthesis of cis-5-methyl menthol (cis-2-isopropyl-5,5-dimethylcyclohexanol) (Exemplary Compound rac-cis-5)

[Chem. 56]

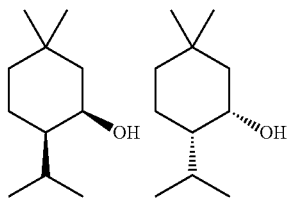

By using the method of Synthesis Example 16, cis-5-methyl menthol was obtained as a colorless oil (28.5 g, yield: 94%) from 5-methylmenthone (rac-7) (30.0 g, 17.8 mmol) obtained in Synthesis Example 5.

HRMS: mass: 170.1656, actual measurement value: 170.1671

$^1$H-NMR (500 MHz, CDCl$_3$): δ0.83-0.90 (m, 4H), 0.95 (t, 6H, J=6.2 Hz), 1.06-1.08 (m, 4H), 1.13-1.21 (m, 1H), 1.33 (dd, 1H, J=14.5, 3.3 Hz), 1.40-1.66 (m, 5H), 4.11 (br, 1H)

[Synthesis Example 18] Synthesis of 5-methylmenthyl carbaldehyde (2-isopropyl-5,5-dimethylcyclohexane carbaldehyde) (Exemplary Compound rac-13a)

[Chem. 57]

This reaction was performed under a nitrogen atmosphere. To a 10-L four-necked flask equipped with a condenser were added (methoxymethyl)triphenylphosphonium chloride (1344 g, 3.92 mol, 1.1 eq.), toluene (3000 mL), and (+)-5-methylmenthone ((+)-7) (600 g, 3.57 mol, 1.1 eq.) obtained in Synthesis Example 4. The temperature in the system was increased to 20° C., and potassium t-butoxide (440 g, 3.92 mol, 1.1 eq.) was slowly added thereto over 1.5 hours while maintaining the temperature in the system at 30° C. or lower. After 1 hour, elimination of (+)-5-methylmenthone and production of methyl enol ether (20) were confirmed by GC, and a 35% hydrochloric acid aqueous solution (743 g, 7.13 mol, 2.0 eq.) was added thereto. The temperature was increased to 70° C. over 1.5 hours, and aging was performed for 1 hour at an internal system temperature of 70° C., and complete consumption of methyl enol ether was confirmed by GC. As a post-treatment, tap water was added thereto to wash the oil layer, followed by further washing once with a 5% aqueous sodium bicarbonate solution. Thereafter, tap water and heptane were added thereto, and aging was performed for 1 hour at an internal system temperature of 5° C. or lower. The resulting solution was suction filtered, and the filtrate was transferred to a separating funnel, and the aqueous layer was removed. After the oil layer was concentrated under reduced pressure, Claisen distillation was performed (bath temperature: 120 to 135° C., overhead: 58 to 94° C., 2.2 to 4.7 mmHg), whereby objective 5-methylmenthyl carbaldehyde (13a) (593 g, yield: 93%) was obtained as a yellowish oil.

Methyl Enol Ether (20a)
GCMS: mass: 196.18, actual measurement value: 196.2
$^1$H-NMR (400 MHz, CDCl$_3$): δ0.76-0.82 (m, 3H), 0.85-0.93 (m, 9H), 1.09-1.21 (m, 1H), 1.36-1.46 (m, 2H), 1.47-1.70 (m, 3H), 1.71-1.87 (m, 1H), 2.14-2.33 (m, 1H), 3.49-3.51 (m, 3H), 5.71-5.82 (m, 1H)

5-Methylmenthyl Carbaldehyde (13a)
GCMS: mass: 182.17, actual measurement value: 182.2
$^1$H-NMR (400 MHz, CDCl$_3$): δ0.81 (d, 3H, J=7.2 Hz), 0.87-0.96 (m, 9H), 1.16-1.29 (m, 3H), 1.31-1.37 (m, 1H), 1.41-1.56 (m, 3H), 1.62-1.72 (m, 1H), 2.26-2.42 (m, 1H), 9.46 (d, 1H, J=3.6 Hz)

[Synthesis Example 19] Synthesis of 5-methylmenthyl carboxylic acid (2-isopropyl-5,5-dimethylcyclohexane carboxylic acid) (Exemplary Compound rac-11a)

[Chem. 58]

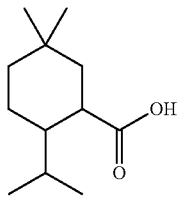

To a 5-L four-necked flask equipped with a condenser and a dropping funnel, 67% nitric acid (223 g, 2.37 mol, 1.5 eq.) was added, and the temperature in the system was increased until reaching 46° C. while stirring. 5-Methylmenthyl carbaldehyde (13a) (28.8 g, 0.158 mol, 0.1 eq.) obtained in Synthesis Example 18 was prepared in the dropping funnel, and then dropped over 30 minutes while maintaining the temperature in the system at 46 to 54° C. Subsequently, a heptane solution (288 mL) of 5-methylmenthyl carbaldehyde (rac-13a) (259 g, 1.42 mol, 0.9 eq.) obtained in Synthesis Example 18 was prepared in the dropping funnel, and then dropped over 4 hours while maintaining the temperature in the system at 46 to 54° C. After completion of the dropping, aging was performed for 2 hours at an internal temperature of 50° C., and a post-treatment was performed. Tap water and toluene were added thereto to effect washing, followed by transferring to a separating funnel, and the aqueous layer was removed. To the oil layer was added an aqueous solution of sodium sulfite (18.9 g, 0.150 mol, 0.095 eq.), followed by stirring at 40° C. to 50° C. for 20 minutes, and a 30% aqueous sulfuric acid solution (26.6 g, 0.079 mol, 0.05 eq.) was added thereto to effect washing, followed by transferring to a separating funnel, and the aqueous layer was removed. To the oil layer were added tap water and a 25% aqueous sodium hydroxide solution (278 g, 1.74 mol, 1.1 eq.), followed by transferring to a separating funnel, and the oil layer was removed. Further, the aqueous layer was washed once with toluene, and toluene and a 30% aqueous sulfuric acid solution (350 g, 0.181 mol, 0.66 eq.) were added thereto to effect washing, followed by transferring to a separating funnel, and the aqueous layer was removed. The oil layer was further washed twice with tap water, and the oil layer was concentrated under reduced pressure, followed by drying, whereby objective 5-methylmenthyl carboxylic acid (rac-11a) (270 g, yield: 89%) was obtained as a yellowish crystal.

[Example 3] Synthesis of Exemplary Compound rac-14a-38 (N-(4-(cyanomethyl)phenyl)-2-isopropyl-5,5-dimethylcyclohexanecarboxamide)

[Chem. 59]

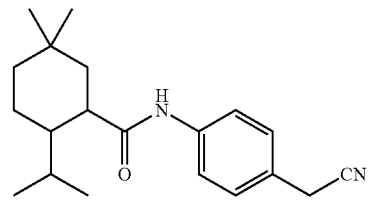

Under a nitrogen atmosphere, to a 100-mL four-necked flask were added 5-methylmenthyl carboxylic acid (rac-11a) (500 mg, 2.52 mmol) obtained in Synthesis Example 7, 8, 9, or 19, thionyl chloride (0.27 mL, 1.50 eq.), and a few drops of dimethylfuran (DMF), followed by stirring at room temperature for 3 hours. The solution in the system was distilled off, and toluene (2 mL) was added thereto. The inside of the system was cooled to 10° C. or lower, and 4-aminobenzyl cyanide (1.00 g, 3.00 eq.) was added slowly thereto. After two and a half hours, the reaction solution was transferred to a separating funnel, and tap water and chloroform were added thereto to effect washing. The oil layer was washed twice with dilute hydrochloric acid, and further washed once with a saturated saline solution, and then dried with anhydrous magnesium sulfate. The obtained solution was concentrated under reduced pressure, followed by recrystallization by using heptane/chloroform, whereby a white crystal (407 mg, yield: 52%) was obtained.

Melting point: 121 to 122° C.
HRMS: mass: 313.2274, actual measurement value: 313.2271 ([M+H]$^+$)
$^1$H-NMR (500 MHz, CDCl$_3$): δ0.86 (d, 3H, J=7.0 Hz), 0.88-1.00 (m, 9H), 1.20-1.31 (m, 3H), 1.39-1.65 (m, 4H), 1.71-1.81 (m, 1H), 2.30 (td, 1H, J=11.8, 3.8 Hz), 3.70 (s, 2H), 7.26 (d, 2H, J=8.2 Hz), 7.32 (br, 1H), 7.56 (d, 1H, J=8.2 Hz)

[Example 4] Synthesis of Exemplary Compound rac-14a-38 (N-(4-(cyanomethyl)phenyl)-2-isopropyl-5,5-dimethylcyclohexanecarboxamide)

[Chem. 60]

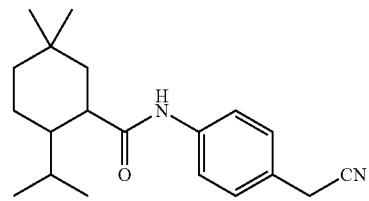 [SMILES: CC(C)C1CCC(C)(C)CC1C(=O)Nc1ccc(CC#N)cc1]

By using the synthesis method described in PTL 16, the same compound was also obtained even using 5-methylmenthyl amide (14a-50) obtained in Example 1, copper iodide, phosphoric acid, and 4-iodobenzyl cyanide (yield: 43%).

[Example 5] Synthesis of Exemplary Compound rac-14a-2 (N-ethyl-2-isopropyl-5,5-dimethylcyclohexanecarboxamide)

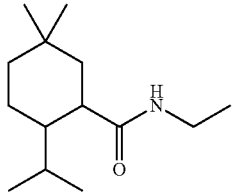 [SMILES: CCNC(=O)C1CC(C)(C)CCC1C(C)C]

[Chem. 61]

Under a nitrogen atmosphere, to a 100-mL four-necked flask were added 5-methylmenthyl carboxylic acid (rac-11a) (500 mg, 2.52 mmol) obtained in Synthesis Example 7, 8, 9, or 19, thionyl chloride (0.27 mL, 1.50 eq.), and a few drops of DMF, followed by stirring at room temperature for 3 hours. The solution in the system was distilled off, and toluene (2 mL) was added thereto. The inside of the system was cooled to 10° C. or lower, and a THF solution of ethylamine (6.3 mL, 2 mol/L, 5.0 eq.) was added slowly thereto. After two and a half hours, the reaction solution was transferred to a separating funnel, and tap water and chloroform were added thereto to effect washing. The oil layer was washed twice with dilute hydrochloric acid, and further washed once with a saturated saline solution, and then dried with anhydrous magnesium sulfate. The obtained solution was concentrated under reduced pressure, followed by recrystallization by using heptane/chloroform, whereby a white crystal (281 mg, yield: 49%) was obtained.

Melting point: 101 to 105° C.

HRMS: mass: 226.2165, actual measurement value: 226.2162 ([M+H]$^+$)

$^1$H-NMR (500 MHz, CDCl$_3$): δ0.80 (d, 3H, J=6.9 Hz), 0.89-0.93 (m, 6H), 1.13 (t, 3H, J=10.1 Hz), 1.15-1.27 (m, 3H), 1.37-1.53 (m, 4H), 1.71 (quid, 1H, J=7.0, 2.5 Hz), 2.08 (td, 1H, J=11.0, 4.8 Hz), 3.23-3.35 (m, 2H), 5.37 (br, 1H)

[Example 6] Synthesis of Exemplary Compound rac-14a-22 (methyl 2-(2-isopropyl-5,5-dimethylcyclohexanecarboxamide) acetate)

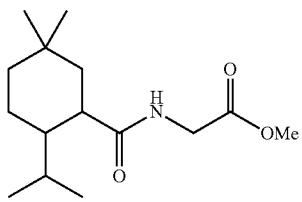

[Chem. 62]

Under a nitrogen atmosphere, to a 100-mL four-necked flask were added 5-methylmenthyl carboxylic acid (rac-11a) (500 mg, 2.52 mmol) obtained in Synthesis Example 7, 8, 9, or 19, thionyl chloride (0.27 mL, 1.50 eq.), and a few drops of DMF, followed by stirring at room temperature for 3 hours. The solution in the system was distilled off, and toluene (2 mL) was added thereto. The inside of the system was cooled to 10° C. or lower, and glycine methyl ester hydrochloride (633 mg, 2.00 eq.) and triethylamine (2 mL) were added slowly thereto. After two and a half hours, the reaction solution was transferred to a separating funnel, and tap water and chloroform were added thereto to effect washing. The oil layer was washed twice with dilute hydrochloric acid, and further washed once with a saturated saline solution, and then dried with anhydrous magnesium sulfate. The obtained solution was concentrated under reduced pressure, followed by recrystallization by using heptane/chloroform, whereby a white crystal (422 mg, yield: 62%) was obtained.

Melting point: 101 to 104° C.

HRMS: mass: 292.1883, actual measurement value: 292.1886 ([M+Na]$^+$)

$^1$H-NMR (500 MHz, CDCl$_3$): δ0.82 (d, 3H, J=6.9 Hz), 0.87-0.97 (m, 9H), 1.08-1.33 (m, 2H), 1.36-2.02 (m, 6H), 2.26 (td, 1H, J=11.7, 4.3 Hz), 3.76 (s, 3H), 4.05 (d, 2H, J=5.3 Hz), 6.16 (br, 1H)

[Example 7] Synthesis of Exemplary Compound rac-14a-33 (2-isopropyl-N-(4-methoxyphenyl)-5,5-dimethylcyclohexanecarboxamide)

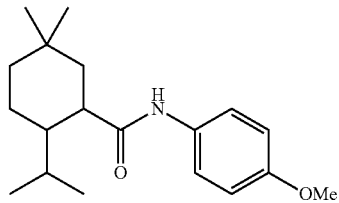 [SMILES: COc1ccc(NC(=O)C2CC(C)(C)CCC2C(C)C)cc1]

[Chem. 63]

Under a nitrogen atmosphere, to a 100-mL four-necked flask were added 5-methylmenthyl carboxylic acid (rac-11a) (400 mg, 2.52 mmol) obtained in Synthesis Example 7, 8, 9, or 19, thionyl chloride (0.22 mL, 1.50 eq.), and a few drops of DMF, followed by stirring at room temperature for 3 hours. The solution in the system was distilled off, and toluene (5 mL) was added thereto. The inside of the system was cooled to 10° C. or lower, and p-anisidine (497 mg, 2.00 eq.) and triethylamine (1.6 mL) were added slowly thereto. After two and a half hours, the reaction solution was transferred to a separating funnel, and tap water and chloroform were added thereto to effect washing. The oil layer was washed twice with dilute hydrochloric acid, and further washed once with a saturated saline solution, and then dried with anhydrous magnesium sulfate. The obtained solution was concentrated under reduced pressure, followed by recrystallization by using heptane/chloroform, whereby a white crystal (445 mg, yield: 73%) was obtained.

Melting point: 115 to 118° C.

HRMS: mass: 303.2238, actual measurement value: 303.2198

$^1$H-NMR (500 MHz, CDCl$_3$): δ0.85 (d, 3H, J=7.0 Hz), 0.91-0.95 (m, 9H), 1.16-1.30 (m, 2H), 1.35-1.62 (m, 5H), 1.76-1.83 (m, 1H), 2.24 (td, 1H, J=11.5, 4.5 Hz), 6.85 (d, 2H, J=9.0 Hz), 7.02 (br, 1H), 7.43 (d, 2H, J=8.5 Hz)

[Example 8] Synthesis of Exemplary Compound rac-14a-23 (ethyl 2-(2-isopropyl-5,5-dimethylcyclohexanecarboxamide) acetate)

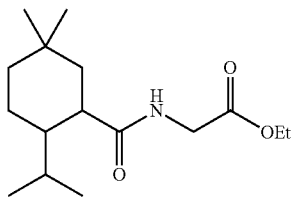

[Chem. 64]

Under a nitrogen atmosphere, to a 100-mL four-necked flask were added 5-methylmenthyl carboxylic acid (rac-11a) (400 mg, 2.52 mmol) obtained in Synthesis Example 7, 8, 9, or 19, thionyl chloride (0.22 mL, 1.50 eq.), and a few drops of DMF, followed by stirring at room temperature for 3 hours. The solution in the system was distilled off, and toluene (5 mL) was added thereto. The inside of the system was cooled to 10° C. or lower, and glycine ethyl ester hydrochloride (563 mg, 2.00 eq.) and triethylamine (1.6 mL) were added slowly thereto. After two and a half hours, the reaction solution was transferred to a separating funnel, and tap water and chloroform were added thereto to effect washing. The oil layer was washed twice with dilute hydrochloric acid, and further washed once with a saturated saline solution, and then dried with anhydrous magnesium sulfate. The obtained solution was concentrated under reduced pressure, followed by recrystallization by using heptane/chloroform, whereby a white crystal (409 mg, yield: 62%) was obtained.

Melting point: 104 to 107° C.

HRMS: mass: 283.2161, actual measurement value: 283.2147

$^1$H-NMR (500 MHz, CDCl$_3$): δ0.82 (d, 3H, J=6.6 Hz), 0.88-0.92 (m, 9H), 1.15-1.27 (m, 2H), 1.29 (t, 3H, J=7.0 Hz), 1.41-1.54 (m, 5H), 1.73 (quid, 1H, J=7.0, 2.5 Hz), 2.23 (td, 1H, J=11.5, 4.0 Hz), 4.03 (d, 2H, J=6.6 Hz), 4.22 (q, 2H, J=7.0 Hz), 5.91 (br, 1H)

[Example 9] Synthesis of Exemplary Compound rac-14a-40 (2-isopropyl-N-(4-methoxy-2-methylphenyl)-5,5-dimethylcyclohexanecarboxamide)

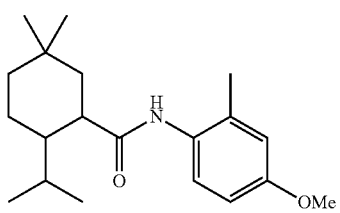 [SMILES: COc1ccc(NC(=O)C2CC(C)(C)CCC2C(C)C)c(C)c1]

[Chem. 65]

Under a nitrogen atmosphere, to a 100-mL four-necked flask were added 5-methylmenthyl carboxylic acid (rac-11a) (600 mg, 3.03 mmol) obtained in Synthesis Example 7, 8, 9, or 19, thionyl chloride (0.33 mL, 1.50 eq.), and a catalytic amount of DMF, followed by stirring at room temperature for 3 hours. The solution in the system was distilled off under reduced pressure, and toluene (2 mL) was added thereto. The inside of the system was cooled to 10° C. or lower in an ice bath, and 2-methyl-4-methoxyaniline (1.25 g, 3.0 eq.) was added slowly thereto. After two and a half hours, completion of the reaction was confirmed by GC-MS, and a post-treatment was performed. The reaction solution was transferred to a separating funnel, and tap water and chloroform were added thereto to effect washing. The oil layer was washed twice with dilute hydrochloric acid, and further washed once with a saturated saline solution, and then dried with anhydrous magnesium sulfate. The resulting solution was concentrated under reduced pressure, and then isolation and purification were performed by column chromatography (heptane/ethyl acetate=4/1), whereby an amorphous solid was obtained (770 mg, yield: 80%).

HRMS: mass: 317.2355 actual measurement value: 317.2370

$^1$H-NMR (500 MHz, CDCl$_3$): δ0.88 (d, 3H, J=6.9 Hz), 0.92-0.98 (m, 9H), 1.20-1.31 (m, 3H), 1.43-1.64 (m, 4H), 1.82-1.91 (m, 1H), 2.22 (s, 3H), 2.31 (td, 1H, J=11.6, 1.2 Hz), 3.77 (s, 3H), 6.71-6.76 (m, 2H), 6.82 (br, 1H), 7.47-7.52 (m, 1H)

[Example 10] Synthesis of Exemplary Compound rac-14a-46 (methyl 4-(2-isopropyl-5,5-dimethylcyclohexanecarboxamide)-3-methylbenzoate)

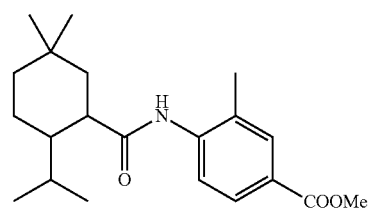 [SMILES: COC(=O)c1ccc(NC(=O)C2CC(C)(C)CCC2C(C)C)c(C)c1]

[Chem. 66]

Under a nitrogen atmosphere, to a 100-mL four-necked flask were added 5-methylmenthyl carboxylic acid (rac-11a) (600 mg, 3.03 mmol) obtained in Synthesis Example 7, 8, 9, or 19, thionyl chloride (0.33 mL, 1.50 eq.), and a catalytic amount of DMF, followed by stirring at room temperature for 3 hours. The solution in the system was distilled off under reduced pressure, and toluene (2 mL) was added thereto. The inside of the system was cooled to 10° C. or lower in an ice bath, and 3-methyl-4-aminobenzoic acid methyl ester (1.50 g, 3.0 eq.) was added slowly thereto. After two and a half hours, completion of the reaction was confirmed by GC-MS, and a post-treatment was performed. The reaction solution was transferred to a separating funnel, and tap water and chloroform were added thereto to effect washing. The oil layer was washed twice with dilute hydrochloric acid, and further washed once with a saturated saline solution, and then dried with anhydrous magnesium sulfate. The resulting solution was concentrated under reduced pressure, and then isolation and purification were performed by column chromatography (heptane/ethyl acetate=4/1), whereby an amorphous solid was obtained (306 mg, yield: 29%).

HRMS: mass: 345.2304 actual measurement value: 345.2298

$^1$H-NMR (500 MHz, CDCl$_3$): δ0.85-0.98 (m, 12H), 1.20-1.33 (m, 3H), 1.45-1.65 (m, 4H), 1.82 (quid, 1H, J=6.6, 2.1 Hz), 2.29-2.40 (m, 4H), 7.05 (br, 1H), 7.86-7.90 (m, 2H), 8.14 (d, 1H, J=8.2 Hz)

[Example 11] Synthesis of Exemplary Compound rac-14a-41 (N-(3-hydroxy-4-methoxyphenyl)-2-isopropyl-5,5-dimethylcyclohexanecarboxamide)

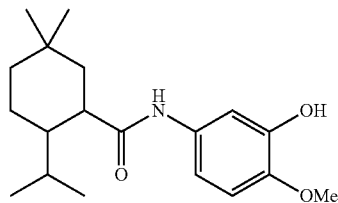 [SMILES: COc1ccc(NC(=O)C2CC(C)(C)CCC2C(C)C)cc1O]

[Chem. 67]

Under a nitrogen atmosphere, to a 100-mL four-necked flask were added 5-methylmenthyl carboxylic acid (rac-11a) (300 mg, 1.51 mmol) obtained in Synthesis Example 7, 8, 9, or 19, thionyl chloride (0.17 mL, 1.50 eq.), and a catalytic amount of DMF, followed by stirring at room temperature for 3 hours. The solution in the system was distilled off under reduced pressure, and toluene (2 mL) was added thereto. The inside of the system was cooled to 10° C. or lower in an ice bath, and 2-amino-5-methoxyphenol (632 mg, 3.0 eq.) was added slowly thereto. After two and a half hours, completion of the reaction was confirmed by GC-MS, and a post-treatment was performed. The reaction solution was transferred to a separating funnel, and tap water and chloroform were added thereto to effect washing. The oil layer was washed twice with dilute hydrochloric acid, and further washed once with a saturated saline solution, and then dried with anhydrous magnesium sulfate. The resulting solution was concentrated under reduced pressure, and then isolation and purification were performed by column chromatography (heptane/ethyl acetate=5/1), whereby an amorphous solid was obtained (446 mg, yield: 92%). This solid was recrystallized by using heptane/chloroform, whereby a white crystal was obtained.

Melting point: 93 to 98° C.

HRMS: mass: 320.2220 actual measurement value: 320.2227 ([M+H]$^+$)

$^1$H-NMR (500 MHz, CDCl$_3$): δ0.85 (d, 3H, J=7.0 Hz), 0.90-1.00 (m, 9H), 1.19-1.30 (m, 3H), 1.41-1.60 (m, 4H), 1.79-1.84 (m, 1H), 2.23 (quid, 1H, J=14.0, 3.1 Hz), 3.87 (s, 3H), 6.79 (d, 2H, J=8.6 Hz), 6.93 (br, 1H), 7.04-7.11 (m, 2H)

[Example 12] Synthesis of Exemplary Compound rac-14a-16 (2-isopropyl-5,5-dimethyl-N-(2-(pyridin-2-yl)ethyl)cyclohexanecarboxamide)

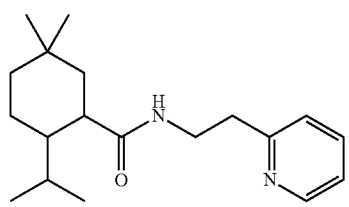 [SMILES: CC(C)C1CCC(C)(C)CC1C(=O)NCCc1ccccn1]

[Chem. 68]

Under a nitrogen atmosphere, to a 100-mL four-necked flask were added 5-methylmenthyl carboxylic acid (rac-11a) (400 mg, 2.02 mmol) obtained in Synthesis Example 7, 8, 9, or 19, thionyl chloride (0.35 mL, 1.50 eq.), and a catalytic amount of DMF, followed by stirring at room temperature for 3 hours. The solution in the system was distilled off under reduced pressure, and toluene (2 mL) was added thereto. The inside of the system was cooled to 10° C. or lower in an ice bath, and 2-(2-aminoethyl)-pyridine (739 mg, 3.0 eq.) was added slowly thereto. After two and a half hours, completion of the reaction was confirmed by GC-MS, and a post-treatment was performed. The reaction solution was transferred to a separating funnel, and tap water and chloroform were added thereto to effect washing. Washing was further performed twice with a saturated saline solution, followed by drying with anhydrous magnesium sulfate. The resulting solution was concentrated under reduced pressure, and then isolation and purification were performed by column chromatography (heptane/ethyl acetate=5/1 to 0/1), whereby an amorphous solid was obtained (342 mg, yield: 52%). This solid was recrystallized by using heptane/chloroform, whereby a white crystal was obtained.

Melting point: 104 to 107° C.

HRMS: mass: 303.2431, actual measurement value: 303.2421 ([M+H]$^+$)

$^1$H-NMR (500 MHz, CDCl$_3$): δ0.68 (d, 3H, J=6.9 Hz), 0.83 (d, 3H, J=7.0 Hz), 0.85 (s, 3H), 0.89 (s, 3H), 1.05-1.27 (m, 3H), 1.35-1.48 (m, 4H), 1.55-1.62 (m, 1H), 2.0-2.10 (m, 1H), 2.99 (t, 2H, J=6.4 Hz), 3.58-3.74 (m, 2H), 6.30 (br, 1H), 7.13-7.18 (m, 2H), 7.61 (td, 1H, J=7.6, 1.8 Hz), 8.52-8.55 (m, 2H)

[Example 13] Synthesis of Exemplary Compound rac-14a-47 (N-(4-(hydroxymethyl)phenyl)-2-isopropyl-5,5-dimethylcyclohexanecarboxamide)

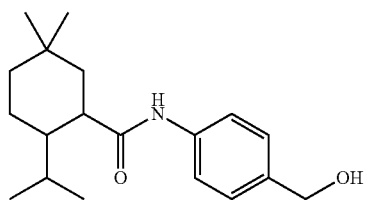

[Chem. 69]

Under a nitrogen atmosphere, to a 100-mL four-necked flask were added 5-methylmenthyl carboxylic acid (rac-11a) (300 mg, 1.51 mmol) obtained in Synthesis Example 7, 8, 9, or 19, thionyl chloride (0.17 mL, 1.50 eq.), and a catalytic amount of DMF, followed by stirring at room temperature for 3 hours. The solution in the system was distilled off under reduced pressure, and toluene (2 mL) was added thereto. The inside of the system was cooled to 10° C. or lower in an ice bath, and 2-aminobenzyl alcohol (559 mg, 3.0 eq.) was added slowly thereto. After two and a half hours, completion of the reaction was confirmed by GC-MS, and a post-treatment was performed. The reaction solution was transferred to a separating funnel while filtering, and tap water and chloroform were added thereto to effect washing. The oil layer was washed twice with dilute hydrochloric acid, and further washed once with a saturated saline solution, and then dried with anhydrous magnesium sulfate. The resulting solution was concentrated under reduced pressure, and recrystallized by using chloroform/ethyl acetate, whereby a yellow crystal was obtained (330 mg, yield: 72%).

Melting point: 165-172° C.

HRMS: mass: 326.2091, actual measurement value: 326.2083 ([M+Na]+)

¹H-NMR (500 MHz, DMSO-D₆): δ0.83 (d, 3H, J=6.9 Hz), 0.85 (d, 3H, J=6.9 Hz), 0.91 (d, 6H, J=7.3 Hz), 1.10-1.22 (m, 2H), 1.32-1.51 (h, 5H), 1.62 (quid, 1H, J=6.8, 2.4 Hz), 2.43-2.52 (m, 1H), 4.42 (s, 2H), 5.06 (br, 1H), 7.21 (d, 2H, J=8.4 Hz), 7.52-7.60 (m, 2H), 9.82 (s, 1H)

[Example 14] Synthesis of Exemplary Compound rac-17a-2 ((S)-(trans-2-isopropyl-5,5-dimethylcyclohexyl)2-hydroxypropanoate)

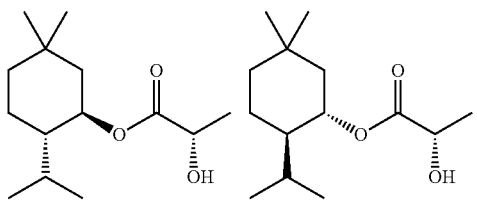

[Chem. 70]

Synthesis was performed according to the synthesis method of PTL 25. Under a nitrogen atmosphere, to a 50-mL Schlenk flask equipped with a Dean-Stark condenser were added racemic-trans-5-methyl menthol (rac-trans-5) (1.50 g, 8.81 mmol) obtained in Synthesis Example 3, (S)-lactic acid (1.35 g, 15.0 mmol, 1.7 eq.), and heptane (25 mL), and stirring was started. A catalytic amount of concentrated sulfuric acid was added to the inside of the system, and the temperature in the system was increased to 100° C., and refluxing and stirring were performed while removing water from the inside of the system. After 4 hours, the progress of the reaction was confirmed by GC-MS, and a post-treatment was performed. The inside of the system was cooled to room temperature, and washing was performed once with a 1 mass % aqueous sodium hydroxide solution, and once with a saturated saline solution. The oil layer was dried with anhydrous magnesium sulfate, and then filtered and concentrated, and thereafter isolation and purification were performed by column chromatography (heptane/ethyl acetate=7/1), whereby an objective colorless oil was obtained (766 mg, yield: 36%).

$[\alpha]^D_{20}$=-5.13 (c=0.5, EtOH)

HRMS: mass: 265.1774 actual measurement value: 265.1768 ([M+Na]+)

¹H-NMR (500 MHz, CDCl₃): δ0.80 (dd, 3H, J=7.0, 3.7 Hz), 0.90 (dd, 3H, J=7.0, 3.7 Hz), 0.93-0.97 (m, 6H), 1.14-1.30 (m, 3H), 1.35-1.43 (m, 4H), 1.58 (br, 2H), 1.68-1.76 (m, 1H), 1.79-1.88 (m, 1H), 2.84 (d, 1H, J=5.4 Hz), 4.18-4.25 (m, 1H), 4.90-4.98 (m, 1H)

[Example 15] Synthesis of Exemplary Compound (1R,2S)-17a-2 ((S)-((1R,2S)-2-isopropyl-5,5-dimethylcyclohexyl)2-hydroxypropanoate)

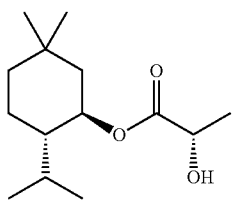 [SMILES: CC(C)[C@@H]1CCC(C)(C)C[C@H]1OC(=O)[C@H](C)O]

[Chem. 71]

By using the method of Example 14, a (-)-form was obtained as a colorless oil (367 mg, yield: 34%) from (-)-trans-5-methyl menthol (750 mg, 4.40 mmol) obtained in Synthesis Example 12.

$[\alpha]^D_{20}$=-62.3 (c=0.2, EtOH)

HRMS: mass: 243.1970 actual measurement value: 243.1960 (FI)

¹¹H-NMR (500 MHz, CDCl₃): δ0.81 (d, 3H, J=6.9 Hz), 0.90 (d, 3H, J=7.0 Hz), 0.93-0.97 (m, 6H), 1.14-1.30 (m, 3H), 1.35-1.43 (m, 4H), 1.58 (br, 2H), 1.71 (dq, 1H, J=12.2, 2.4 Hz), 1.79-1.88 (m, 1H), 2.89 (br, 1H), 4.18-4.25 (br, 1H), 4.95 (td, 1H, J=11.0, 4.6 Hz)

[Example 16] Synthesis of Exemplary Compound (1S,2R)-17a-2 ((S)-((1S,2R)-2-isopropyl-5,5-dimethylcyclohexyl)2-hydroxypropanoate)

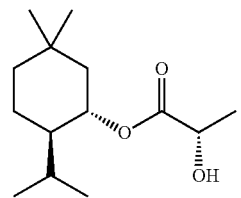 [SMILES: CC(C)[C@H]1CCC(C)(C)C[C@@H]1OC(=O)[C@H](C)O]

[Chem. 72]

By using the method of Example 14, a (+)-form was obtained as a colorless oil (367 mg, yield: 34%) from (+)-trans-5-methyl menthol (750 mg, 4.40 mmol) obtained in Synthesis Example 13.

$[\alpha]^D_{20}$=+41.1 (c=0.4, EtOH)

HRMS: mass: 265.1774 actual measurement value: 265.1777 (ESI, [M+Na]+)

¹H-NMR (500 MHz, CDCl₃): δ0.79 (d, 3H, J=6.9 Hz), 0.91 (d, 3H, J=7.0 Hz), 0.93-0.97 (m, 6H), 1.14-1.30 (m, 3H), 1.35-1.43 (m, 4H), 1.58 (br, 2H), 1.75 (dq, 1H, J=12.2, 2.4 Hz), 1.79-1.88 (m, 1H), 2.84 (d, 1H, 5.4 Hz), 4.18-4.25 (m, 1H), 4.93 (td, 1H, J=11.0, 4.6 Hz)

[Example 17] Synthesis of Exemplary Compound rac-14a-43 (methyl 2-(2-isopropyl-5,5-dimethylcyclohexanecarboxamide) benzoate)

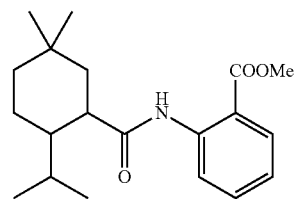

[Chem. 73]

This reaction was performed under a nitrogen atmosphere. To a 100-mL reactor were added 5-methylmenthyl carboxylic acid (rac-11a) (400 mg, 2.02 mmol) obtained in Synthesis Example 7, 8, 9, or 19, thionyl chloride (0.22 mL, 1.50 eq.), and a few drops of DMF, followed by stirring at room temperature for 3 hours. The solution in the system was distilled off, and toluene (2 mL) was added thereto. The inside of the system was cooled to 10° C. or lower in an ice bath, and methyl 2-aminobenzoate (610 mg, 2.0 eq.) was added slowly thereto. After two and a half hours, completion of the reaction was confirmed by GC-MS, and a post-treatment was performed. The reaction solution was transferred to a separating funnel while filtering, and tap water and chloroform were added thereto to effect washing. The oil layer was washed twice with dilute hydrochloric acid, and further washed once with a saturated saline solution, and then dried with anhydrous magnesium sulfate. The resulting solution was concentrated under reduced pressure, and then isolation and purification were performed by column chromatography, whereby an objective amorphous oil was obtained (510 mg, yield: 76%).

HRMS: mass: 332.2220 actual measurement value: 332.2240 ([M+H]$^+$)

$^1$H-NMR (500 MHz, CDCl$_3$): δ0.87 (d, 3H, J=6.9 Hz), 0.92 (d, 1H, J=6.9 Hz), 0.95 (s, 6H), 1.21-1.32 (m, 3H), 1.44-1.67 (m, 4H), 1.78 (quid, 1H, J=7.0, 2.7 Hz), 2.38-2.45 (m, 1H), 3.94 (s, 3H), 7.04-7.05 (m, 1H), 7.51-7.56 (m, 1H), 8.03 (dd, 1H, J=8.0, 1.4 Hz), 8.77 (dd, 1H, J=8.5, 1.0 Hz), 11, 1 (br, 1H)

[Example 18] Synthesis of Exemplary Compound rac-19a-1 (6-isopropyl-9,9-dimethyl-1,4-dioxaspiro[4.5]decan-2-yl)methanol)

[Chem. 74]

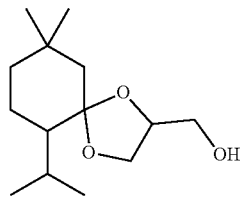

This reaction was performed under a nitrogen atmosphere. To a reaction flask equipped with a Dean-Stark condenser were added 5-methylmenthone (rac-7) (3.00 g, 17.8 mmol) obtained in Synthesis Example 5, glycerol (9.85 g, 7.80 mL, 6.0 eq.), toluene (20 mL), and a few drops of concentrated sulfuric acid, followed by refluxing and stirring. In the condenser, water deposited in the system was observed. After 15 hours, the inside of the system was cooled to room temperature, and the reaction solution was concentrated and then purified by column chromatography (heptane/ethyl acetate), whereby an objective orangish oil (1.96 g, yield: 45%) was obtained.

HRMS: mass: 242.1892, actual measurement value: 242.1881

$^1$H-NMR (500 MHz, CDCl$_3$): δ0.86-1.01 (m, 12H), 1.18-1.88 (m, 8H), 2.01-2.19 (m, 1H), 36.52-3.81 (m, 3H), 3.96-4.30 (m, 2H) (diastereomers mixture)

[Example 19] Synthesis of Exemplary Compound 14a-38i ((−)-trans-N-(4-(cyanomethyl)phenyl)-2-isopropyl-5,5-dimethylcyclohexanecarboxamide)

[Chem. 75]

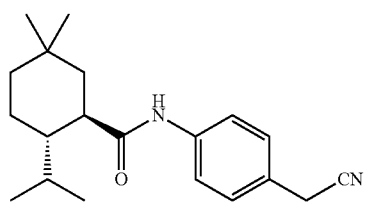 [SMILES: CC(C)[C@@H]1CCC(C)(C)C[C@H]1C(=O)Nc1ccc(CC#N)cc1]

This reaction was performed under a nitrogen atmosphere. To a 100-mL reactor were added (−)-5-methylmenthyl carboxylic acid (1R,2S)-11a (450 mg, 2.27 mmol) obtained in Synthesis Example 15, thionyl chloride (0.25 mL, 1.50 eq.), and a few drops of DMF, followed by stirring at room temperature for 3 hours. The solution in the system was distilled off, and toluene (2 mL) was added thereto. The inside of the system was cooled to 10° C. or lower in an ice bath, and 4-aminobenzcyanide (900 mg, 3.0 eq.) was added slowly thereto. After two and a half hours, completion of the reaction was confirmed by GC-MS, and a post-treatment was performed. The reaction solution was transferred to a separating funnel and tap water and chloroform were added thereto to effect washing. The oil layer was washed twice with dilute hydrochloric acid, and further washed once with a saturated saline solution, and then dried with anhydrous magnesium sulfate. The resulting solution was concentrated under reduced pressure, and then isolation and purification were performed by column chromatography, whereby an amorphous solid was obtained (545 mg, yield: 77%, 80% ee.).

$[α]^D{}_{20}$=−20.6 (c=0.5, EtOH)

HRMS: mass: 317.2202, actual measurement value: 317.2211 (FI)

$^1$H-NMR (500 MHz, CDCl$_3$): δ0.86 (d, 3H, J=7.0 Hz), 0.88-1.00 (m, 9H), 1.20-1.31 (m, 3H), 1.39-1.65 (m, 4H), 1.71-1.81 (m, 1H), 2.30 (td, 1H, J=11.8, 3.8 Hz), 3.70 (s, 2H), 7.26 (d, 2H, J=8.0 Hz), 7.32 (br, 1H), 7.56 (d, 1H, J=8.0 Hz)

[Example 20] Synthesis of Exemplary Compound rac-14a-42 (N-(2-hydroxy-4-methoxyphenyl)-2-isopropyl-5,5-dimethylcyclohexanecarboxamide)

[Chem. 76]

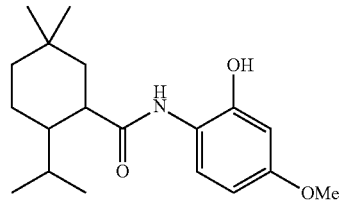 [SMILES: COc1ccc(NC(=O)C2CC(C)(C)CCC2C(C)C)c(O)c1]

This reaction was performed under a nitrogen atmosphere. To a 100-mL reactor were added 5-methylmenthyl carboxylic acid (rac-11a) (350 mg, 1.77 mmol) obtained in Synthesis Example 7, 8, 9, or 19, thionyl chloride (0.19 mL, 1.50 eq.), and a few drops of DMF, followed by stirring at room temperature for 3 hours. The solution in the cold system was distilled off, and toluene (2 mL) was added thereto. The inside of the system was cooled to 10° C. or lower in an ice bath, and 2-amino-5-methoxyphenol (491 mg, 2.0 eq.) was added slowly thereto. Stirring was performed at room temperature for two and a half hours, and thereafter at an internal temperature of 60° C. for 1 hour, and completion of the reaction was confirmed by GC-MS. As a post-treatment, the reaction solution was transferred to a separating funnel, and tap water and chloroform were added thereto to effect washing. The oil layer was washed twice with dilute hydrochloric acid, and further washed once with a saturated saline solution, and then dried with anhydrous magnesium sulfate. To the inside of the system, further silica gel was added, followed by stirring, and the solution was filtered and concentrated, whereby a white solid was obtained (401 mg, 1.255 mmol, yield: 71%). A small amount of this compound was recrystallized by using heptane/chloroform, whereby a white crystal was obtained.

Melting point: 153 to 155° C.

HRMS: mass: 320.2220 actual measurement value: 320.2226 ([M+H]$^+$)

$^1$H-NMR (500 MHz, CDCl$_3$): δ0.87 (d, 3H, J=6.9 Hz), 0.92-0.98 (m, 9H), 1.19-1.31 (m, 3H), 1.45-1.65 (m, 7H), 1.75-1.83 (m, 1H), 2.41 (td, 1H, J=12.0, 3.5 Hz), 6.61 (d, 1H, J=2.9 Hz), 6.70 (dd, 1H, J=8.9, 3.0 Hz), 6.94 (d, 1H, J=8.9 Hz), 8.08 (s, 1H)

[Example 21] Synthesis of Exemplary Compound rac-14a-44 (methyl 3-(2-isopropyl-5,5-dimethylcyclohexanecarboxamide) benzoate)

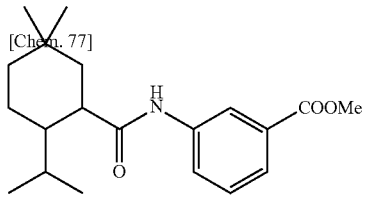 [SMILES: COC(=O)c1cccc(NC(=O)C2CC(C)(C)CCC2C(C)C)c1]

[Chem. 77]

This reaction was performed under a nitrogen atmosphere. To a 100-mL reactor were added 5-methylmenthyl carboxylic acid (rac-11a) (400 mg, 4.03 mmol) obtained in Synthesis Example 7, 8, 9, or 19, thionyl chloride (0.35 mL, 1.50 eq.), and a few drops of DMF, followed by stirring at room temperature for 3 hours. The solution in the system was distilled off, and toluene (2 mL) was added thereto. The inside of the system was cooled to 10° C. or lower in an ice bath, and methyl-m-aminobenzoate (610 mg, 2.0 eq.) was added slowly thereto. Stirring was performed at room temperature for 2 hours, and thereafter at an internal temperature of 50° C. for 1 hour, and completion of the reaction was confirmed by GC-MS. As a post-treatment, the reaction solution was transferred to a separating funnel, and tap water and chloroform were added thereto to effect washing. The oil layer was washed twice with dilute hydrochloric acid, and further washed once with a saturated saline solution, and then dried with anhydrous magnesium sulfate. The resulting solution was concentrated under reduced pressure, and then isolation and purification were performed by column chromatography, whereby an amorphous solid was obtained (529 mg, 1.60 mmol, yield: 79%).

HRMS: mass: 332.2220 actual measurement value: 332.2237 ([M+H]$^+$)

$^1$H-NMR (500 MHz, CDCl$_3$): δ0.83-0.97 (m, 12H), 1.20-1.35 (m, 3H), 1.39-1.67 (m, 4H), 1.76-1.84 (m, 1H), 2.30 (td, 1H, J=11.8, 4.1 Hz), 7.30 (br, 1H), 7.39 (d, 1H, J=7.9 Hz), 7.75-7.80 (m, 1H), 7.87-8.05 (h, 2H)

[Example 22] Synthesis of Exemplary Compound rac-14a-45 (methyl 4-(2-isopropyl-5,5-dimethylcyclohexanecarboxamide) benzoate)

[Chem. 78]

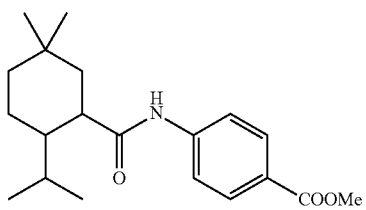 [SMILES: COC(=O)c1ccc(NC(=O)C2CC(C)(C)CCC2C(C)C)cc1]

This reaction was performed under a nitrogen atmosphere. To a 100-mL reactor were added 5-methylmenthyl carboxylic acid (rac-11a) (400 mg, 4.03 mmol) obtained in Synthesis Example 7, 8, 9, or 19, thionyl chloride (0.35 mL, 1.50 eq.), and a few drops of DMF, followed by stirring at room temperature for 3 hours. The solution in the system was distilled off, and toluene (2 mL) was added thereto. The inside of the system was cooled to 10° C. or lower in an ice bath, and methyl-p-aminobenzoate (610 mg, 2.0 eq.) was added slowly thereto. Stirring was performed at room temperature for 2 hours, and thereafter at an internal temperature of 50° C. for 1 hour, and completion of the reaction was confirmed by GC-MS. As a post-treatment, the reaction solution was transferred to a separating funnel, and tap water and chloroform were added thereto to effect washing. The oil layer was washed twice with dilute hydrochloric acid, and further washed once with a saturated saline solution, and then dried with anhydrous magnesium sulfate. The resulting solution was concentrated under reduced pressure, and then isolation and purification were performed by column chromatography, whereby an amorphous solid was obtained (491 mg, 1.48 mmol, yield: 73%).

HRMS: mass: 332.2220 actual measurement value: 332.2232 ([M+H]$^+$)

$^1$H-NMR (500 MHz, CDCl$_3$): δ0.83-0.97 (m, 12H), 1.20-1.35 (m, 3H), 1.44-1.64 (m, 4H), 1.73-1.83 (m, 1H), 2.30 (td, 1H, J=11.9, 3.7 Hz), 7.30 (br, 1H), 7.62 (d, 1H, J=8.7 Hz), 7.99 (dt, 1H, J=9.1, 1.9 Hz)

[Example 23] Sensory Evaluation of Exemplary Compound rac-14a-38

[Chem. 79]

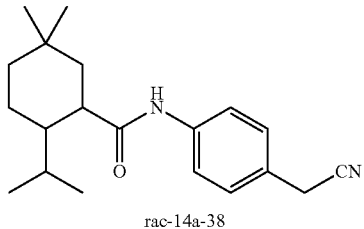

rac-14a-38

Comparative Compound 1

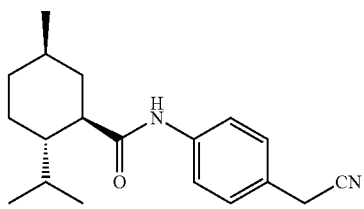

Sensory Evaluation was performed by comparison with Comparative Compound 1 (Evercool 180), which has a strong cool feeling among conventionally known compounds, and has a similar structure. Each of Exemplary Compound rac-14a-38 and Comparative Compound 1 was prepared as a 2 ppm aqueous solution, and the evaluation was performed.

[Sensory Findings]

A cool feeling was exhibited after a lapse of 1 minute to several minutes from when Exemplary Compound rac-14a-38 was put in the mouth. The cool feeling persisted for 30 minutes or more.

The cool feeling characteristic was more natural than that of Comparative Compound 1 (Evercool 180). While Evercool 180 had a menthol-like characteristic, only a cool feeling was felt by rac-14a-38.

The cool feeling characteristic of rac-14a-38 was sharper than that of Comparative Compound 1 (Evercool 180).

[Example 24] Sensory Evaluation of Exemplary Compound rac-14a-23

[Chem. 80]

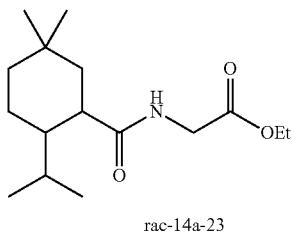

rac-14a-23

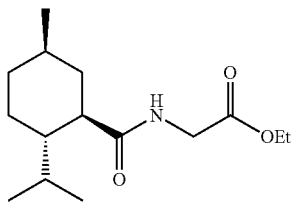

Comparative Compound 2

Sensory Evaluation was performed by comparison with Comparative Compound 2, which is conventionally known, and has a similar structure. Each of Exemplary Compound rac-14a-23 and Comparative Compound 2 was prepared as a 30 ppm aqueous solution, and the evaluation was performed.

[Sensory Findings]

In rac-14a-23, the sharp cool feeling stimulation was stronger than that in Comparative Compound 2. Exhibition of a cool feeling was later than Comparative Compound 2, and the cool feeling intensity peak was comparable to that of Comparative Compound 2. The sharp cool feeling of rac-14a-23 was highly persistent, and there was an impression that the bottom level of the cool feeling was raised throughout the whole time. The persistence was superior to that of Comparative Compound 2.

[Example 25] Sensory Evaluation of Exemplary Compound rac-14a-34

[Chem. 81]

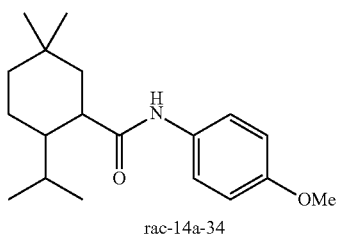

rac-14a-34

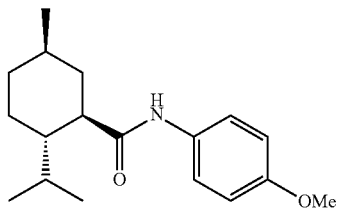

Comparative Compound 3

Sensory Evaluation was performed by comparison with Comparative Compound 3, which is conventionally known, and has a similar structure. Each of Exemplary Compound rac-14a-34 and Comparative Compound 3 was prepared as a 30 ppm aqueous solution, and the evaluation was performed.

[Sensory Findings]

A top umami feeling of rac-14a-34 was comparable to that of Comparative Compound 3, and the start of exhibition of a cool feeling was later than Comparative Compound 3. The cool feeling intensity increased over time. Since the umami persisted, the secretion of saliva continued, which was an interesting characteristic (it was felt that the saliva was secreted from the back of the throat).

[Example 26] Sensory Evaluation of Exemplary Compound rac-14a-40

[Chem. 82]

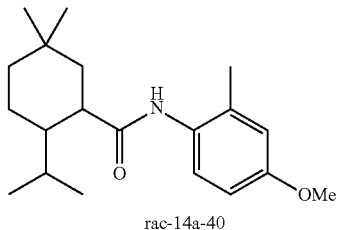

rac-14a-40

Sensory Evaluation was performed by comparison with Comparative Compound 3, which is conventionally known, and has a similar structure. Each of Exemplary Compound rac-14a-40 and Comparative Compound 3 was prepared as a 30 ppm aqueous solution, and the evaluation was performed.

[Sensory Findings]

Top umami and salty tastes of rac-14a-40 were stronger and shaper than those of Comparative Compound 3. Umami and a numbness feeling were exhibited simultaneously, and therefore, there was an impression that it may have a salvation effect.

[Example 27] Sensory Evaluation of Exemplary Compound rac-14a-46

[Chem. 83]

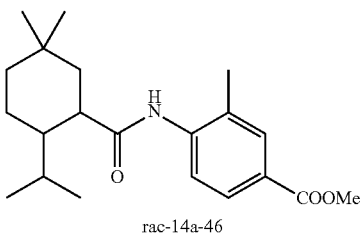

rac-14a-46

Sensory Evaluation was performed by comparison with Comparative Compound 3 which is conventionally known. Each of Exemplary Compound rac-14a-46 and Comparative Compound 3 was prepared as a 30 ppm aqueous solution, and the evaluation was performed.

[Sensory Findings]

rac-14a-46 had a clear and light touch characteristic of an ester, but the start was late, and the cool feeling intensity persisted.

[Example 28] Sensory Evaluation of Exemplary Compound rac-14a-41

[Chem. 84]

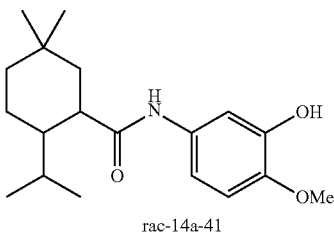

rac-14a-41

Sensory Evaluation was performed by comparison with Comparative Compound 3 which is conventionally known. Each of Exemplary Compound rac-14a-41 and Comparative Compound 3 was prepared as a 30 ppm aqueous solution, and the evaluation was performed.

[Sensory Findings]

It was observed that rac-14a-41 had the start of a cool feeling slightly earlier than Comparative Compound 3. Chemical-like bitterness was somewhat felt as a first taste, but it disappeared after a while, and therefore, it was not a problematic level. The cool feeling intensity was about 1.2 to 1.3 times of that of Comparative Compound 3, which was strong intensity. The cool feeling was accompanied by a clear feeling than a fiery feeling, and a favorable cool feeling was observed. The cool feeling considerably remained in the back of the throat, which proved that it also has persistence.

[Example 29] Sensory Evaluation of Exemplary Compound rac-14a-47

[Chem. 85]

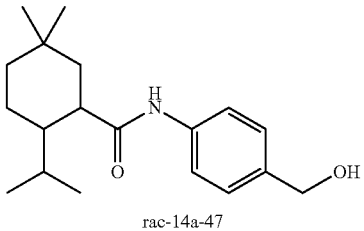

rac-14a-47

Sensory Evaluation was performed by comparison with Comparative Compound 3 which is conventionally known. Each of Exemplary Compound rac-14a-47 and Comparative Compound 3 was prepared as a 30 ppm aqueous solution, and the evaluation was performed.

[Sensory Findings]

rac-14a-47 was characterized in early start of a cool feeling. Umami accompanied in the same manner as Comparative Compound 3, however, stronger umami was felt than that in Comparative Compound 3. The cool feeling intensity was about 1.5 to 2 times of that of Comparative Compound 3, which was very strong, and the cool feeling was accompanied by a fiery feeling (burning feeling). The cool feeling considerably remained in the back of the throat, which proved that it also has persistence.

[Example 30] Evaluation when Scenting Shampoo

[Chem. 86]

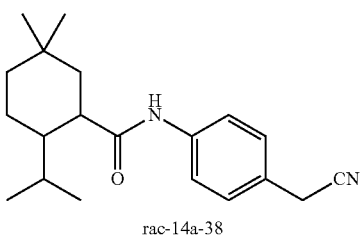

rac-14a-38

Comparative Compound 4

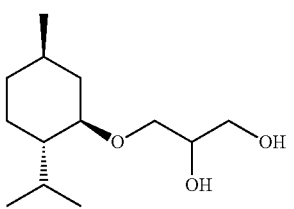

Shampoos (A) to (C) scented with l-menthol, and conventionally known Comparative Compound 4 or Exemplary Compound rac-14a-38, were prepared, and a sensory evaluation was performed. The compositions of the shampoos (A) to (C) are shown below.

(A) body shampoo base 900 g+l-menthol 30 g+dipropylene glycol (DPG) 70 g (B) body shampoo base 900 g+l-menthol 30 g+Comparative Compound 4 10% in DPG 70 g (C) body shampoo base 900 g+l-menthol 30 g+Exemplary Compound rac-14a-38 1% in DPG 70 g The formulation of the body shampoo base is as follows.

TABLE 1

| (Component) | (Blending amount, g) |
|---|---|
| Ald C-12 lauric | 0.1 |
| Ambrettolide | 10 |
| Ambroxan | 7.0 |
| Benzacetate | 3.5 |
| Bergamot oil | 30 |
| Canthoxal | 13 |
| Citronellol | 5.5 |
| Cassis base | 10 |
| α-Damascone | 1.0 |
| γ-Decalactone | 3.0 |
| Dimethylbenz carbinol | 13 |
| Dipropylene glycol | 63.9 |
| Ethyl linalool | 35 |
| Floralozone | 0.6 |
| Florol | 5.0 |
| Grapefruit oil | 40 |
| Galactoride, 50% DPG solution | 55 |
| Hedione | 240 |
| Heliobouquet | 17 |
| 3-cis-hexenyl acetate | 1.5 |
| 3-cis-hexenyl salicylate | 13 |
| 3-cis-hexen-1-ol | 2.5 |
| Californian lemon oil | 110 |
| Lilial | 70 |
| Manzanate | 0.2 |
| γ-Methylionone | 4.0 |
| Methyl pamplemousse | 5.0 |
| Orbitone/Iso-E-super | 100 |
| Phenoxanol | 15 |
| Salicylacetate | 1.0 |
| Veltol plus | 0.2 |
| Verdox | 25 |
| Total | 900 |

[Evaluation Comments]

The formulations of the shampoo (B) and the shampoo (C) have a higher cool feeling effect than that of the shampoo (A), and the shampoo (C) had a cool feeling effect equivalent to or higher than that of the shampoo (B) although the blending amount of the cooling agent is 1/10 that in the shampoo (B).

[Example 31] Evaluation when Scenting Beer-Flavored Beverage

[Chem. 87]

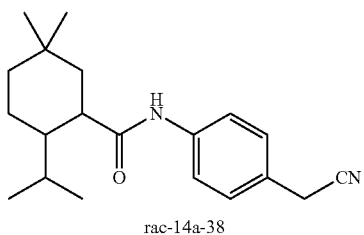

rac-14a-38

-continued

Comparative Compound 4

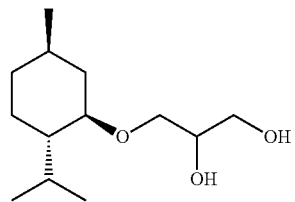

Beer-flavored beverages (D) to (F) scented with 1-menthol, and Exemplary Compound rac-14a-38 or conventionally known Comparative Compound 4, were prepared, and a sensory evaluation was performed. The compositions of the beer-flavored beverages (D) to (F) are shown below.

(D) non-alcoholic beer taste beverage 1000 g+l-menthol 1 mg (1 ppm)

(E) non-alcoholic beer taste beverage 1000 g+l-menthol 1 mg (1 ppm)+Comparative Compound 4 1 mg (1 ppm) added (F) non-alcoholic beer taste beverage 1000 g+l-menthol 1 mg (1 ppm)+Exemplary Compound rac-14a-38 0.1 mg (0.1 ppm) added The formulation of a beer flavor is as follows.

TABLE 2

| (Component) | (Blending amount, g) |
|---|---|
| Ethyl acetate | 50 |
| Isoamyl alcohol | 50 |
| 2-phenylethyl alcohol | 20 |
| Octanoic acid | 8.0 |
| Hexanoic acid | 3.0 |
| Decanoic acid | 0.5 |
| Isoamyl acetate | 2.0 |
| 2-phenylethyl acetate | 2.0 |
| Methionol | 1.0 |
| Ethyl octanoate | 0.5 |
| Ethyl hexanoate | 0.1 |
| Ethyl decanoate | 0.05 |
| 4-vinylguaiacol | 0.2 |
| γ-nonalactone | 0.02 |
| Linalool | 0.01 |
| Sotolone | 0.002 |
| Damascenone | 0.001 |
| Propylene glycol (PG) | 862.617 |
| Total | 1000 |

The formulation of the beer-flavored beverage using the beer flavor having the above formulation is as follows.

TABLE 3

| (Component) | (Blending amount, g) |
|---|---|
| Reduced maltose starch syrup | 23 |
| Malt extract | 5.0 |
| Digestion resistant dextrin | 3.0 |
| Anhydrous citric acid | 0.6 |
| Sodium citrate | 0.3 |
| Caramel color | 0.2 |
| Vitamin C | 0.05 |
| Iso-alpha acid | 0.1 |
| Beer flavor | 1.0 |
| Carbonated water | 966.75 |
| Total | 1000 |

[Evaluation Comments]

The beer-flavored beverage (E) and the beer-flavored beverage (F) have a higher cool feeling effect than that of the beer-flavored beverage (D), and the beer-flavored beverage (F) had a cool feeling effect equivalent to or higher than that of the beer-flavored beverage (E) although the blending amount of the cooling agent is ¹/₁₀ that in the beer-flavored beverage (E). Further, the beer-flavored beverage (F) provided higher quality and more pleasant cool feeling than that of the beer-flavored beverage (E).

[Example 32] Evaluation when Scenting Toothpaste

[Chem. 88]

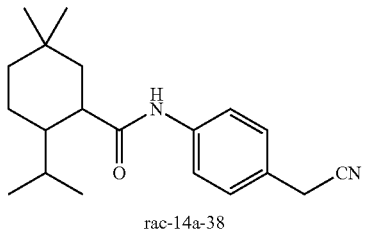

rac-14a-38

Comparative Compound 4

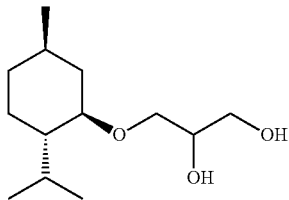

Toothpastes (G) to (I) scented with 1-menthol, and Exemplary Compound rac-14a-38 or conventionally known Comparative Compound 4, were prepared, and a sensory evaluation was performed. The compositions of toothpastes (G) to (I) are shown below.

(G) toothpaste base 990 g+toothpaste flavor base 4 g+1-menthol 4 g+ethyl alcohol (EtOH) 2 g (H) toothpaste base 990 g+toothpaste flavor base 4 g+1-menthol 4 g+Comparative Compound 4 10% in EtOH 2 g (I) toothpaste base 990 g+toothpaste flavor base 4 g+1-menthol 4 g+Exemplary Compound rac-14a-38 1% in EtOH 2 g The formulation of the toothpaste flavor base is as follows.

TABLE 4

| (Component) | (Blending amount, g) |
|---|---|
| Anethole | 0.6 |
| Eucalyptol | 0.2 |
| Lemon oil | 0.1 |
| Mint white oil | 1.0 |
| Peppermint oil | 1.5 |
| Propylene glycol (PG) | 0.6 |
| Total | 4.0 |

Further, the formulation of the toothpaste base is as follows.

TABLE 5

| (Component) | (Blending amount, g) |
|---|---|
| Calcium carbonate | 400.0 |
| Anhydrous silicic acid | 16.5 |
| Sorbitol solution (70%) | 240.0 |
| Sodium lauryl sulfate | 13.0 |
| Carboxymethyl cellulose sodium | 12.5 |
| Carrageenan | 3.0 |
| Sodium benzoate | 4.0 |
| Saccharin sodium | 1.5 |
| Purified water | 259.5 |
| Propylene glycol (PG) | 40.0 |
| Total | 990.0 |

[Evaluation Comments]

The toothpaste (H) and the toothpaste (I) have a higher cool feeling effect than that of the toothpaste (G), and the toothpaste (I) had a cool feeling effect equivalent to or higher than that of the toothpaste (H) although the blending amount of the cooling agent is ¹/₁₀ that in the toothpaste (H). In addition, the cool feeling effect of the toothpaste (I) was felt for 30 minutes or more. Further, at the same time, an effect that the mint feeling of the toothpaste flavor strongly spreads was also felt.

[Example 33] Evaluation of Cool Feeling Intensity

The cool feeling intensity of each compound is shown in Table 6 to Table 8. The measurement of the cool feeling intensity was performed with reference to NPL 6. A concentration $EC_{50}$ at which a cool feeling is felt is shown below as the index of the cool feeling intensity.

TABLE 6

| Compounds evaluated | $EC_{50}$ (μM) |
|---|---|
| 14a-50 | 15.5 |
| rac-14a-38 | 0.24 |
| rac-14a-2 | 2.27 |

TABLE 6-continued

| Compounds evaluated | EC$_{50}$ (µM) |
|---|---|
| rac-14a-34 | 0.055 |
| rac-14a-23 | 0.49 |
| rac-14a-40 | 0.079 |
| rac-14a-46 | 1.50 |

TABLE 7

| Compounds evaluated | EC$_{50}$ (µM) |
|---|---|
| rac-14a-41 | 0.027 |
| rac-14a-47 | 0.048 |

TABLE 7-continued

| Compounds evaluated | EC$_{50}$ (µM) |
|---|---|
| rac-14a-16 | 0.13 |
| rac-17a-2 | 64.7 |
| (1R,2S)-17a-2 | 78.5 |
| (1S,2R)-17a-2 | 24.5 |

TABLE 8

| Compounds evaluated | EC$_{50}$ (µM) |
|---|---|
| (1R,2S)-19a-1 | 32.4 |

TABLE 8-continued

| Compounds evaluated | EC$_{50}$ (µM) |
|---|---|
| 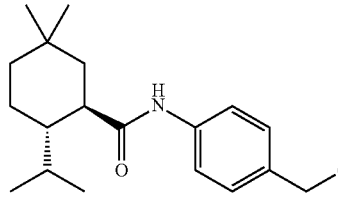 14a-38i | 0.14 |
| 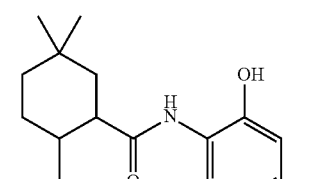 rac-14a-42 | 0.35 |
| 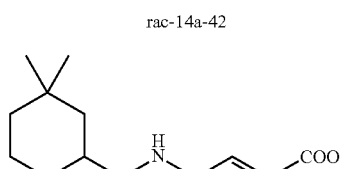 rac-14a-44 | 5.24 |
| 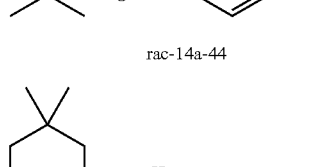 rac-14a-45 | 3.53 |

While the present invention has been described in detail and with reference to specific embodiments thereof, it will be apparent to one skilled in the art that various changes and modifications can be made therein without departing from the spirit and scope of the present invention. The present application is based on a Japanese patent application (No. 2015-062301) filed on Mar. 25, 2015, the content thereof being incorporated herein by reference.

The invention claimed is:

1. A cooling agent composition, comprising a methyl menthol compound which is selected from the following group:

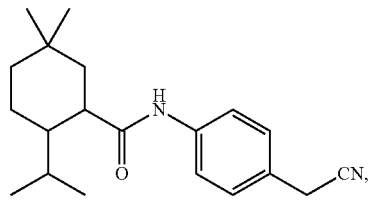

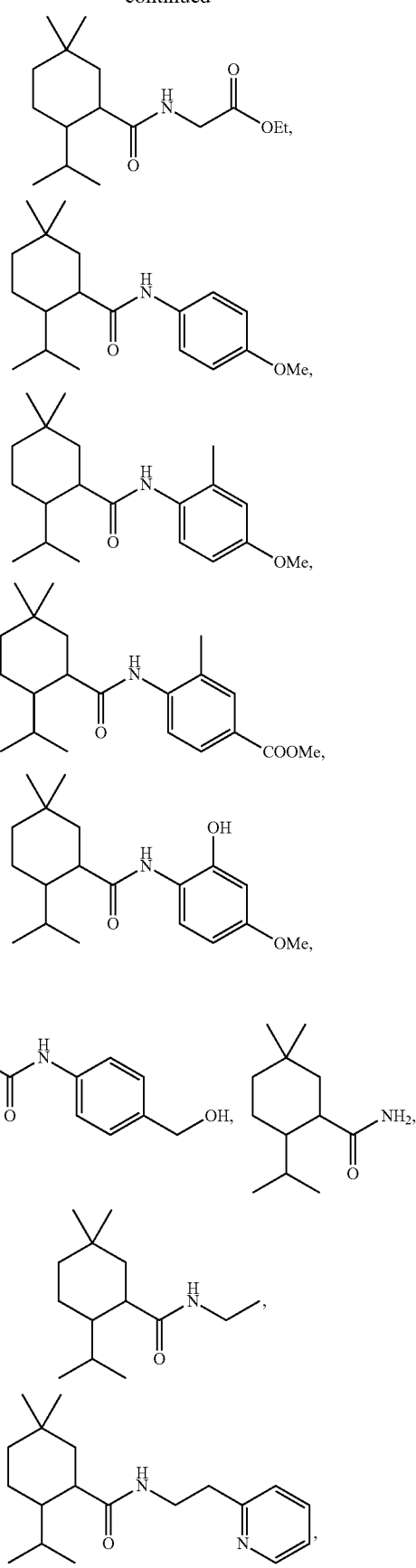

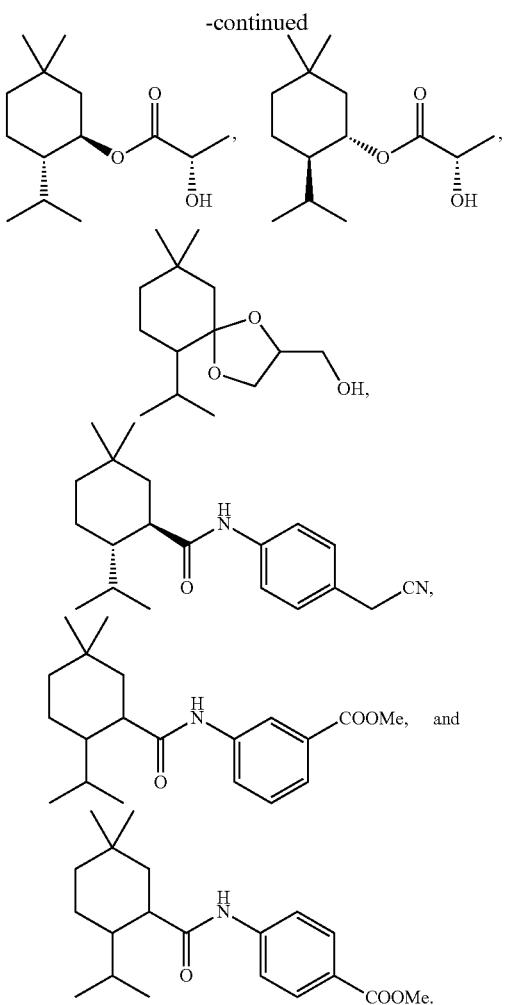

2. The cooling agent composition according to claim 1, further comprising at least one cool feeling substance other than the methyl menthol compound.

3. The cooling agent composition according to claim 2, wherein the cool feeling substance other than the methyl menthol compound is at least one cool feeling substance selected from the group consisting of:
one or more kinds of compounds selected from menthol, menthone, camphor, pulegol, isopulegol, cineole, cubenol, menthyl acetate, pulegyl acetate, isopulegyl acetate, menthyl salicylate, pulegyl salicylate, isopulegyl salicylate, 3-(1-menthoxy)propan-1,2-diol, 2-methyl-3-(1-menthoxy)propan-1,2-diol, 2-(1-menthoxy)ethan-1-ol, 3-(1-menthoxy)propan-1-ol, 4-(1-menthoxy)butan-1-ol, menthyl 3-hydroxybutanoate, menthyl glyoxylate, p-menthane-3,8-diol, 1-(2-hydroxy-4-methylcyclohexyl)ethanone, menthyl lactate, menthone glycerin ketal, menthyl-2-pyrrolidone-5-carboxylate, monomenthyl succinate, alkali metal salts of monomenthyl succinate, alkaline earth metal salts of monomenthyl succinate, monomenthyl glutarate, alkali metal salts of monomenthyl glutarate, alkaline earth metal salts of monomenthyl glutarate, N-[[5-methyl-2-(1-methylethyl)cyclohexyl]carbonyl]glycine, p-menthane-3-carboxylic acid glycerol ester, menthol propylene glycol carbonate, menthol ethylene glycol carbonate, p-menthane-2,3-diol, 2-isopropyl-N,2,3-trimethylbutanamide, N-ethyl-p-menthane-3-carboxamide, ethyl 3-(p-menthane-3-carboxamide)acetate, N-(4-methoxyphenyl)-p-menthanecarboxamide, N-ethyl-2,2-diisopropylbutanamide, N-cyclopropyl-p-menthanecarboxamide, N-(4-cyanomethylphenyl)-p-menthanecarboxamide, N-(2-pyridin-2-yl)-3-p-menthanecarboxamide, N-(2-hydroxyethyl)-2-isopropyl-2,3-dimethylbutanamide, N-(1,1-dimethyl-2-hydroxyethyl)-2,2-diethylbutanamide, cyclopropanecarboxylic acid (2-isopropyl-5-methylcyclohexyl)amide, N-ethyl-2,2-diisopropylbutanamide, N-[4-(2-amino-2-oxoethyl)phenyl]-p-menthanecarboxamide, 2-[(2-p-menthoxy)ethoxy]ethanol, 2,6-diethyl-5-isopropyl-2-methyltetrahydropyran, and trans-4-tert-butylcyclohexanol;
one or more sugar alcohols selected from the group consisting of xylitol, erythritol, dextrose, and sorbitol; and
one or more natural products selected from the group consisting of Japanese mint oil, peppermint oil, spearmint oil, and *eucalyptus* oil.

4. A sensory stimulant composition, comprising the cooling agent composition according to claim 1.

5. The sensory stimulant composition according to claim 4, further comprising at least one warm feeling substance.

6. The sensory stimulant composition according to claim 5, wherein the warm feeling substance is at least one warm feeling substance selected from the group consisting of:
one or more compounds selected from the group consisting of vanillyl methyl ether, vanillyl ethyl ether, vanillyl propyl ether, vanillyl isopropyl ether, vanillyl butyl ether, vanillyl amyl ether, vanillyl isoamyl ether, vanillyl hexyl ether, isovanillyl methyl ether, isovanillyl ethyl ether, isovanillyl propyl ether, isovanillyl isopropyl ether, isovanillyl butyl ether, isovanillyl amyl ether, isovanillyl isoamyl ether, isovanillyl hexyl ether, ethyl vanillyl methyl ether, ethyl vanillyl ethyl ether, ethyl vanillyl propyl ether, ethyl vanillyl isopropyl ether, ethyl vanillyl butyl ether, ethyl vanillyl amyl ether, ethyl vanillyl isoamyl ether, ethyl vanillyl hexyl ether, vanillin propylene glycol acetal, isovanillin propylene glycol acetal, ethyl vanillin propylene glycol acetal, vanillyl butyl ether acetic acid ester, isovanillyl butyl ether acetic acid ester, ethyl vanillyl butyl ether acetic acid ester, 4-(1-menthoxymethyl)-2-(3'-methoxy-4'-hydroxyphenyl)-1,3-dioxolane, 4-(1-menthoxymethyl)-2-(3'-hydroxy-4'-methoxyphenyl)-1,3-dioxolane, 4-(1-menthoxymethyl)-2-(3'-ethoxy-4'-hydroxyphenyl)-1,3-dioxolane, capsaicin, dihydrocapsaicin, nordihydrocapsaicin, homodihydrocapsaicin, homocapsaicin, biscapsanthin, trishomocapsanthin, nornorcapsanthin, norcapsanthin, capsaicinol, vanillyl caprylamide (octylic acid vanillylamide), vanillyl pelargonamide (nonylic acid vanillylamide), vanillyl caproamide (decylic acid vanillylamide), vanillyl undecamide (undecylic acid vanillylamide), N-trans-feruloyltyramine, N-5-(4-hydroxy-3-methoxyphenyl)-2E,4E-pentadienoylpiperidine, N-trans-feruloylpiperidine, N-5-(4-hydroxy-3-methoxyphenyl)-2E-pentenoylpiperidine, N-5-(4-hydroxyphenyl)-2E,4E-pentadienoylpiperidine, piperine, isopiperine, chavicine, isochavicine, piperamine, piperettine, piperolein B, retrofractamide A, pipercide, guineenside, piperiline, piperamide C5:1 (2E), piperamide C7:1 (6E), piperamide C7:2 (2E,6E), piperamide C9:1 (8E), piperamide C9:2 (2E,8E), piperamide C9:3 (2E,4E,8E), fagaramide, sanshool-I, sanshool-II, hydroxysanshool, sanshoamide, gingerol, shogaol, zingerone, methylgingerol, paradol, spilanthol, chavicine, polygodial (tadeonal), isopolygodial, dihydropolygodial, and tadeon; and one or more natural products selected from the group consisting of *capsicum* oil, *capsicum* oleoresin, ginger oleoresin, jambu oleoresin (*Spilanthes oleracea* extract), sansho (*Zanthoxylum piperitum*) extract, sanshoamide, black pepper extract, white pepper extract, and *polygonum* extract.

7. A flavor composition or a fragrance composition, comprising the sensory stimulant composition according to claim 4.

8. A product, which is selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, and comprises the flavor composition or the fragrance composition according to claim 7.

9. A product, which is selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, and comprises the flavor composition or the fragrance composition according to claim 7 in an amount of 0.00001 to 50 mass % based on the total weight of the product.

10. A flavor composition or a fragrance composition, comprising the sensory stimulant composition according to claim 4 in an amount of 0.00001 to 90 mass % based on the total weight of the flavor composition or the fragrance composition.

11. A product, which is selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, and comprises the sensory stimulant composition according to claim 4.

12. A product, which is selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, and comprises the sensory stimulant composition according to claim 4 in an amount of 0.00001 to 50 mass % based on the total weight of the product.

13. A method for producing a product, which is selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, wherein the method comprises blending the sensory stimulant composition according to claim 4.

14. A method for producing a product, which is selected from the group consisting of beverages, foods, fragrances or cosmetics, toiletry products, air care products, daily necessities and household goods, compositions for oral use, hair care products, skin care products, body care products, detergents for clothes, soft finishing agents for clothes, quasi-drugs, and drugs, wherein the method comprises blending the flavor composition or the fragrance composition according to claim 7.

* * * * *